(12) United States Patent
Hildebrandt et al.

(10) Patent No.: US 10,868,255 B2
(45) Date of Patent: Dec. 15, 2020

(54) COMPOUND FOR PHOTOACTIVE ORGANIC ELECTRONIC COMPONENTS AND PHOTOACTIVE ORGANIC ELECTRONIC COMPONENT CONTAINING THE COMPOUND

(71) Applicant: Heliatek GmbH, Dresden (DE)

(72) Inventors: Dirk Hildebrandt, Ulm (DE); Olga Gerdes, Ulm (DE); Roland Fitzner, Ulm (DE); Daniel D'Souza, Dresden (DE); Gunter Mattersteig, Ulm (DE); Andre Weiss, Dresden (DE)

(73) Assignee: HELIATEK GMBH, Dresden (DE)

( * ) Notice: Subject to any disclaimer, the term of this patent is extended or adjusted under 35 U.S.C. 154(b) by 0 days.

(21) Appl. No.: 16/067,640

(22) PCT Filed: Dec. 30, 2016

(86) PCT No.: PCT/EP2016/082900
§ 371 (c)(1),
(2) Date: Jul. 2, 2018

(87) PCT Pub. No.: WO2017/114937
PCT Pub. Date: Jul. 6, 2017

(65) Prior Publication Data
US 2019/0019957 A1    Jan. 17, 2019

(30) Foreign Application Priority Data
Dec. 30, 2015    (DE) ......................... 10 2015 123 005

(51) Int. Cl.
| H01L 51/00 | (2006.01) |
| C07D 407/10 | (2006.01) |
| C07D 409/14 | (2006.01) |
| C07D 495/04 | (2006.01) |
| H01L 51/42 | (2006.01) |
| C07D 493/04 | (2006.01) |

(52) U.S. Cl.
CPC ........ *H01L 51/0065* (2013.01); *C07D 407/10* (2013.01); *C07D 409/14* (2013.01); *C07D 493/04* (2013.01); *C07D 495/04* (2013.01); *H01L 51/005* (2013.01); *H01L 51/0068* (2013.01); *H01L 51/0071* (2013.01); *H01L 51/0072* (2013.01); *H01L 51/0073* (2013.01); *H01L 51/42* (2013.01); *Y02E 10/549* (2013.01)

(58) Field of Classification Search
None
See application file for complete search history.

(56) References Cited

U.S. PATENT DOCUMENTS

| 5,340,833 A | 8/1994 | Bridges et al. |
| 2007/0090371 A1 | 4/2007 | Drechsel et al. |
| 2010/0041635 A1 | 2/2010 | Haddach et al. |
| 2012/0209013 A1 | 8/2012 | Bendikov et al. |
| 2013/0160829 A1 | 6/2013 | Uhrich et al. |

FOREIGN PATENT DOCUMENTS

| DE | 102004014046 A1 | 9/2004 |
| JP | 05326146 A | 12/1993 |
| JP | 0649058 A | 2/1994 |
| JP | 2011526917 A | 10/2011 |
| JP | 2013503152 A | 1/2013 |
| WO | WO 2011161108 A1 | 12/2011 |
| WO | WO 2014062549 A1 | 4/2014 |
| WO | WO 2014128277 A1 | 8/2014 |
| WO | WO 2015044377 A1 | 4/2015 |

OTHER PUBLICATIONS

STN Registry entry for CAS RN 138372-67-5, Entered STN Jan. 17, 1992, Accessed Jun. 23, 2019.*
Sekhar et al., Research on Chemical Intermediates, vol. 42, No. 12, pp. 7947-7962 (May 17, 2016).*
Roland Fitzner et al: "A-D-A-Type Oligothiophenes for Small Molecule Organic Solar Cells: Extending the [pi]-System by Introduction of Ring-Locked Double Bonds", Advanced Functional Materials, Wiley-VCH, Weinheim, vol. 25, No. 12, Mar. 25, 2015 (Mar. 25, 2015), pp. 1845-1856, XP001595297.
Amaresh Mishra et al: "A-D-A-type S, N-Heteropentacenes: Next Generation Molecular Donor Materials for Efficient Vacuum-Processed Organic Solar Cells", Advanced Materials, vol. 26, No. 42, Nov. 1, 2014 (Nov. 1, 2014), pp. 7217-7223, XP55310415.
Roland Fitzner et al: "Dicyanovinyl?Substituted Oligothiophenes: Structure-Property Relationships and Application in Vacuum-Processed Small Molecule Organic Solar Cells", Advanced Functional Materials, Wiley- V C H Verlag GMBH & Co. KGAA, DE, vol. 21, No. 5, Mar. 8, 2011 (Mar. 8, 2011), pp. 897-910, XP001560466.
Yassin A et al: "Evaluation of bis-dicyanovinyl short-chain conjugated systems as donor materials for organic solar cells", Solar Energy Materials and Solar Cells, Elsevier Science Publishers, Amsterdam, NL, vol. 95, No. 2, Feb. 1, 2011 (Feb. 1, 2011), pp. 462-468, XP027576773.
Norio Miyaura, "Metal-Catalyzed Cross-Coupling Reactions of Organoboron Compounds with Organic Halides", Metal-Catalyzed Cross-Coupling Reactions, $2^{nd}$ Edition, Dec. 2004, pp. 41-123.
Terence N. Mitchell, "Organotin Reagents in Cross-Coupling Reactions", Metal-Catalyzed Cross-Coupling Reactions, $2^{nd}$ Edition, Dec. 2004, pp. 125-161.

(Continued)

*Primary Examiner* — Alicia L Otton

(74) *Attorney, Agent, or Firm* — Leydig, Voit & Mayer, Ltd.

(57) ABSTRACT

A compound and method of producing the compound of formula (I) that has high absorption in the short wavelength spectral region of visible light and is capable of being used for an organic electronic component.

26 Claims, 4 Drawing Sheets

(56) References Cited

OTHER PUBLICATIONS

Scott E. Denmark, et al., "Organosilicon Compounds in Cross-Coupling Reactions", Metal-Catalyzed Cross-Coupling Reactions, $2^{nd}$ Edition, Dec. 2004, pp. 163-216.

Paul Knochel, et al., "Carbon-Carbon Bond-Forming Reactions Mediated by Organozinc Reagents", Metal-Catalyzed Cross-Coupling, $2^{nd}$ Edition, Dec. 2004, pp. 619-670.

Paul Knochel, et al., "Carbon-Carbon Bond-Forming Reactions Mediated by Organomagnesium Reagents", Metal-Catalyzed Cross-Coupling Reactions, $2^{nd}$ Edition, Dec. 2004, pp. 671-698.

Ei-ichi Negishi, et al., "Palladium- or Nickel-Catalyzed Cross-Coupling with Organometals Containing Zinc, Aluminium, and Zirconium: The Negishi Coupling", Metal-Catalyzed Cross-Coupling Reactions, $2^{nd}$ Edition, Dec. 2004, pp. 815-889.

\* cited by examiner

COMPOUND FOR PHOTOACTIVE ORGANIC ELECTRONIC COMPONENTS AND PHOTOACTIVE ORGANIC ELECTRONIC COMPONENT CONTAINING THE COMPOUND

CROSS-REFERENCE TO PRIOR APPLICATIONS

This application is a U.S. National Stage Application under 35 U.S.C. § 371 of International Application No. PCT/EP2016/082900 filed on Dec. 30, 2016, and claims benefit to German Patent Application No. DE 10 2015 123 005.4 filed on Dec. 30, 2015 and European Patent Application No. 16181348.0 filed on Jul. 26, 2016. The International Application was published in German on Jul. 6, 2017 as WO 2017/114937 A1 under PCT Article 21(2).

FIELD

The invention relates to compounds suitable, for example, for use in photoactive organic electronic components, and to a photoactive organic electronic component comprising the compounds. The invention additionally relates to a process for preparing compounds of the present invention.

BACKGROUND

Photoactive organic electronic components enable conversion of electromagnetic radiation, for instance in the wavelength range of visible light, to electrical current with exploitation of the photoelectric effect. The conversion requires organic semiconductor materials that exhibit sufficiently good absorption properties.

SUMMARY

An embodiment of the present invention provides a compound of a formula (I):

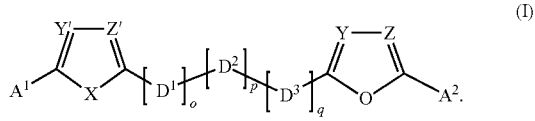

Here, Y, Y', Z and Z' here are each independently selected from: N or $CR^a$.

"Independently selected" in this context also means that $R^a$ can be different in each case for Y, Y', Z and Z'. However, it is also possible, for example, that $R^a$ is the same for two, more than two or all of Y, Y', Z and Z'.

In the compound of this embodiment of the invention, X is selected from: O, S, Se, $Si(R^bR^c)$, $P(R^b)$, $P(O)R^b$.

The $R^a$ to $R^c$ radicals are each independently selected from the group of the following radicals:

H,
halogen,
CN,
$NR^dR^e$ where $R^d$ and $R^e$ are each independently selected
  from the group of the radicals: H and cyclic or open-chain $C_1$-$C_{20}$-alkyl, where individual carbon atoms may be replaced by heteroatoms and where hydrogen atoms in the alkyl radical may be substituted, cyclic or open-chain $C_1$-$C_{20}$-alkyl, where individual carbon atoms may be replaced by heteroatoms,
cyclic or open-chain $C_1$-$C_{20}$—O-alkyl,
cyclic or open-chain $C_1$-$C_{20}$—S-alkyl
cyclic or open-chain $C_2$-$C_{20}$-alkenyl,
cyclic or open-chain $C_2$-$C_{20}$—O-alkenyl,
cyclic or open-chain $C_2$-$C_{20}$—S-alkenyl,
cyclic or open-chain $C_2$-$C_{20}$-alkynyl,
aryl, and
heteroaryl,
where hydrogen atoms in the alkyl, O-alkyl, S-alkyl, alkenyl, O-alkenyl, S-alkenyl, alkynyl, aryl and heteroaryl radicals may each independently be substituted.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1:
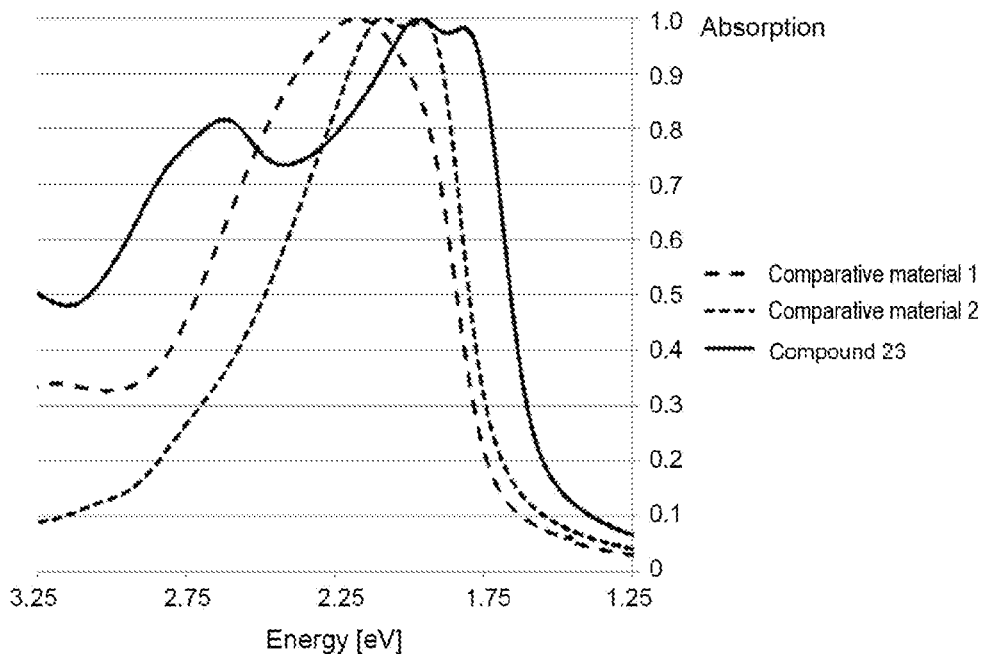
FIG. 1 illustrates a comparison of normalized absorption spectra.

The present invention is directed to organic compounds that exhibit good absorption properties and are suitable, for example, for use in photoactive organic electronic components.

The present invention relates not only to embodiments of compounds of the invention but additionally to the use of the compounds of the invention in photoactive organic electronic components.

The present invention also relates to a photoactive organic electronic component comprising a compound according to the invention.

The invention additionally relates to a compound—as intermediate—for the preparation of the compound of the invention.

The invention further relates to a process for preparing the compound of the invention.

An embodiment of the present invention relates to a compound of the general formula (I):

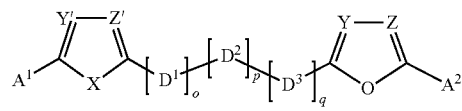

Y, Y', Z and Z' here are each independently selected from: N or $CR^a$.

"Independently selected" in this context also means that $R^a$ can be different in each case for Y, Y', Z and Z'. However, it is also possible, for example, that $R^a$ is the same for two, more than two or all of Y, Y', Z and Z'.

In the compound of the invention, X is selected from: O, S, Se, Si($R^bR^c$), P($R^b$), P(O)$R^b$.

The $R^a$ to $R^e$ radicals are each independently selected from the group of the following radicals:

H, halogen,

CN, $NR^dR^e$ where $R^d$ and $R^e$ are each independently selected from the group of the radicals: H and cyclic or open-chain $C_1$-$C_{20}$-alkyl, where individual carbon atoms may be replaced by heteroatoms and where hydrogen atoms in the alkyl radical may be substituted, cyclic or open-chain $C_1$-$C_{20}$-alkyl, where individual carbon atoms may be replaced by heteroatoms, cyclic or open-chain $C_1$-$C_{20}$—O-alkyl, cyclic or open-chain $C_1$-$C_{20}$—S-alkyl cyclic or open-chain $C_2$-$C_{20}$-alkenyl, cyclic or open-chain $C_2$-$C_{20}$—O-alkenyl, cyclic or open-chain $C_2$-$C_{20}$—S-alkenyl, cyclic or open-chain $C_2$-$C_{20}$-alkynyl, aryl, heteroaryl, where hydrogen atoms in the alkyl, O-alkyl, S-alkyl, alkenyl, O-alkenyl, S-alkenyl, alkynyl, aryl and heteroaryl radicals may each independently be substituted.

Substitution is understood here and hereinafter to mean the replacement of one or more hydrogen atoms by other radicals. For example, hydrogen atoms may be replaced by halogen atoms, for instance fluorine atoms. For example, hydrogen atoms may alternatively be substituted by cyclic or open-chain alkyl radicals, for instance $C_1$-$C_{10}$-, preferably $C_1$-$C_6$-alkyl radicals, especially methyl, ethyl, propyl, butyl, pentyl, hexyl and the like, each of which may be linear or branched, and where the alkyl radicals may be at least partly halogenated, for example fluorinated, preferably perfluorinated.

Halogen in connection with the compound of the invention is understood here and hereinafter to mean in each case F, Cl, Br and I, preferably in each case F.

—CN is a nitrile group.

$NR^dR^e$ is an amine function, which may be a primary, secondary or tertiary amine. $R^d$ and $R^e$ include linear and branched radicals alike. $R^d$ and $R^e$ may also be $C_1$-$C_{20}$-alkyl radicals in which hydrogen atoms are substituted. For example, hydrogen atoms may be replaced by fluorine atoms. $R^d$ and $R^e$ may additionally also be $C_1$-$C_{20}$-alkyl radicals where individual carbon atoms may be replaced by heteroatoms. This means more particularly that non-terminal, non-adjacent carbon atoms may be replaced by atoms such O, S, Se or an NR group where R is H or an alkyl. However, it is preferable that none of the carbon atoms in the $C_1$-$C_{20}$-alkyl radical is replaced by heteroatoms. Preferably, $R^d$ and $R^e$ are selected from H and $C_1$-$C_{10}$-alkyl radicals, especially from H, methyl, ethyl, propyl, butyl and pentyl.

The term "cyclic or open-chain $C_1$-$C_{20}$-alkyl" used for the $R^a$ to $R^c$ radicals in each case includes linear and branched $C_1$-$C_{20}$-alkyl radicals. This may include $C_1$-$C_{20}$-alkyl radicals where individual carbon atoms may be replaced by heteroatoms. This means more particularly that non-terminal, non-adjacent carbon atoms may be replaced by atoms such as O, S, Se or an NR group where R is H or an alkyl. However, it is preferable that none of the carbon atoms in the $C_1$-$C_{20}$-alkyl radical is replaced by heteroatoms. For example, the radicals may be cyclic or open-chain $C_1$-$C_{10}$-alkyl radicals. More particularly, they may be open chain $C_1$-$C_5$-alkyl radicals.

For the cyclic or open-chain $C_1$-$C_{20}$—O-alkyl, cyclic or open-chain $C_1$-$C_{20}$—S-alkyl, cyclic or open-chain $C_2$-$C_{20}$-alkenyl, cyclic or open-chain $C_2$-$C_{20}$—O-alkenyl, cyclic or open-chain $C_2$-$C_{20}$—S-alkenyl and cyclic or open-chain $C_2$-$C_{20}$-alkynyl radicals too, the radicals in each case may be linear or branched.

For the cyclic or open-chain $C_1$-$C_{20}$—O-alkyl and for the cyclic or open-chain $C_2$-$C_{20}$—O-alkenyl, the oxygen in each case is the connection site to the compound of the invention.

Analogously, for the cyclic or open-chain $C_2$-$C_{20}$—S-alkyl and for the cyclic or open-chain $C_2$-$C_{20}$—S-alkenyl, the sulfur in each case is the connection site to the compound of the invention.

Aryl in the case of the present invention is preferably understood to mean a $C_5$-$C_{20}$-aryl, for instance a $C_5$-$C_{12}$-aryl. A heteroaryl in the context of the present invention is understood to mean an aryl, where at least one carbon atom in the aryl in each case is replaced by a heteroatom. The heteroatom may, for example, be O, S, Se, Si, B, N or P.

In the compound of the invention, $A^1$ is an electron-withdrawing radical having at least one C=C double bond. In addition, $A^2$ is an electron-withdrawing radical having at least two conjugated C=C double bonds. For example, $A^1$ has one, two or three C=C double bonds that may be conjugated to one another. For example, $A^2$ has two or three conjugated C=C double bonds. In the case of $A^1$ here, the at least one C=C double bond is preferably not part of an aromatic ring. It is likewise the case for $A^2$ that the at least two conjugated C=C double bonds are preferably not part of an aromatic ring.

The $A^1$ and $A^2$ groups are thus each notable for their electron-withdrawing character and especially act as acceptor groups.

In the compound of the invention, the conjugated $D^1$, $D^2$ and $D^3$ blocks are each independently selected from the group of the following structural units:

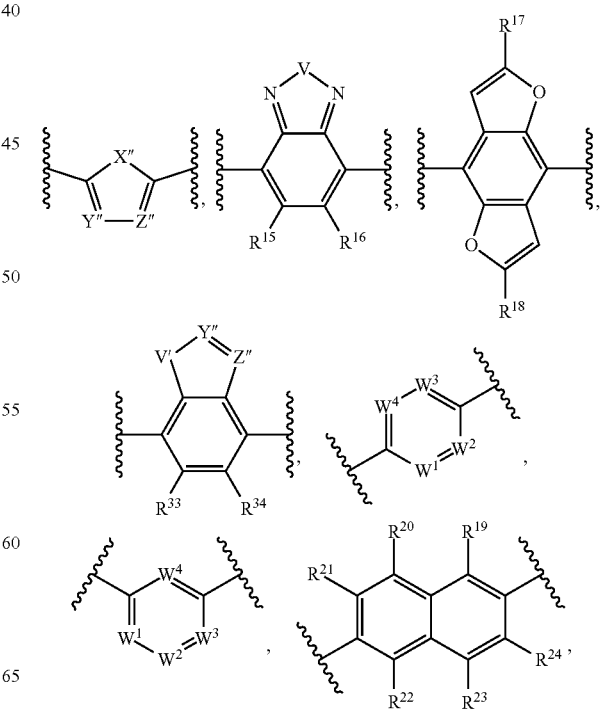

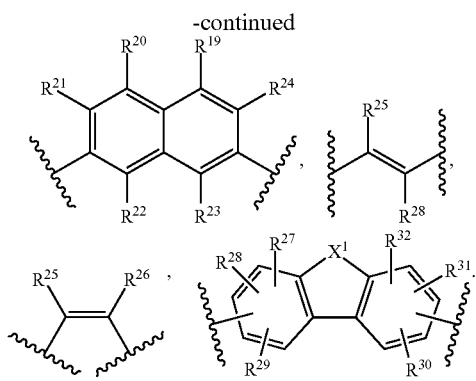

Independently selected means here that the individual conjugated $D^1$, $D^2$ and $D^3$ blocks may each be identical or different structural units from those specified. It is also possible that two or more of the conjugated $D^1$ to $D^3$ blocks can have the same base structure, for example

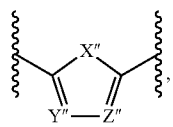

in which case, however, X", Y" and Z" for the different conjugated blocks must not be the same, but must be different. This means that it is possible, for example, that $D^1$ is a furan and $D^2$ a thiophene. It is also possible, for example, that both $D^1$ and $D^2$ are a thiophene, but the two thiophenes have different radicals. The examples just mentioned serve merely for illustration and should not be interpreted in a limiting manner.

The coefficients o and q each independently assume the values of 0 and 1 for the compound of the invention. The coefficient p assumes the values of 0, 1, 2, 3, 4 and 5. However, this is subject to the proviso that at least one of the three coefficients o, p and q must be non-zero. This means that at least one of the three conjugated $D^1$ to $D^3$ blocks must be present.

However, it is also possible, for example, for two or more of the conjugated $D^1$ to $D^3$ blocks to be present.

The structural units mentioned are as follows:
Y" is selected from: N or $CR^g$;
Z" is selected from: N or $CR^h$;
X" is selected from: O, S, Se, $Si(R^iR^j)$, $P(R^i)$, $P(O)R^i$;
V is selected from: O, S, Se or $NR^k$;
V' is selected from: O, S, Se or $NR^k$; preferably $NR^k$,
X1 is selected from: $NR^l$, $CR^lR^m$;
$W^1$ to $W^4$ are independently selected from: N, $CR^n$;
where the $R^g$ to $R^n$ radicals and the $R^{15}$ to $R^{34}$ radicals are each independently selected from the group of the radicals as $R^a$ to $R^c$. In addition, the $R^g$ and $R^h$ radicals may be joined to one another in the form of a ring structure. Moreover, an aryl radical may be fused to said ring structure. It is possible here that the latter aryl radical is substituted.

The ring structure may, for example, be a five-, six- or seven-membered ring. For example, it may be a saturated ring. For example, the ring may have heteroatoms, for instance O or S. Alternatively, it is possible that the ring is a homocyclic ring. For example, the ring may be substituted. For example, the ring may have fluorine atoms or alkyl groups as substituents. The ring may also have at least partly fluorinated alkyl groups as substituents.

The aryl radical which may be fused onto the ring structure may, for example, be a benzene ring having two carbon atoms in common with the ring structure.

The conjugated $D^1$ to $D^3$ blocks together with the two five-membered rings that surround them, together with the two electron-withdrawing $A^1$ and $A^2$ groups, form a significant π electron system.

Whether an organic compound is suitable for use in photoactive organic electronic components depends upon factors including the absorption characteristics of the compound. High absorption is desirable. More particularly, it is advantageous when the compound absorbs within a broad range of the available spectrum of electromagnetic radiation, since photons of a wide variety of different wavelengths can thus be utilized for the generation of electrical power.

Specifically in the region of wavelengths less than 600 nm—especially less than 500 nm—the absorption of many organic compounds conventionally used in photoactive organic electronic components is inadequate. The effect of this is that the photons in this wavelength range cannot be utilized to a sufficient degree.

By contrast, the inventors of the present invention have found that the inventive compounds of the general formula (I) exhibit astonishingly good absorption characteristics within a comparatively broad range of visible light (about 400 to 700 nm). More particularly, a surprisingly high absorption in the short-wave solar spectral range from about 400 to 600 nm was found. Particularly for the wavelength range below 500 nm, distinctly better absorption characteristics were observed than is the case for many compounds conventionally used in photoactive organic electronic components.

The inventors of the present invention have recognized that compounds of the general structure of formula (I) have molecular orbitals having an energy level that enables particularly good absorption properties in the high-energy, i.e. short-wave, region of visible light as well. The compounds are thus of excellent suitability for use in photoactive organic electronic components, for example for components which convert sunlight to electrical power, for instance in photodetectors and light-sensitive transistors, particularly in organic solar cells.

The inventors have additionally found that the compound of the invention having an oxygen atom in the structural element:

of formula (I) generally leads to better optical properties than is the case for compounds that are similar but lack oxygen. It has been found, for example, that the presence of O is preferable over S in this structural element. For example, furan is preferable over thiophene.

The inventors have also found that the effect possessed by said structural element

of formula (I) that has just been described occurs especially in a compound having an $A^2$ group having at least two conjugated C=C double bonds. The common presence of the structural element

together with an electron-withdrawing group $A^2$ having at least two conjugated C=C double bonds—according to the present invention—is a structure motif that has a surprisingly favorable effect on the absorption properties of the compound of the invention.

Moreover, the compounds of the invention generally exhibit good processability and can be deposited by conventional methods in thin organic layers alone or together with further materials. They additionally have adequate thermal, chemical and electrochemical stability to satisfy the demands that are typically made on them in the manufacture and operation of photoactive organic electronic components.

Finally, the compounds are producible with a moderate degree of technical complexity and hence are also comparatively inexpensive.

In a preferred embodiment, exactly one of the three coefficients o, p and q is 1, while the two other coefficients are zero. This means that exactly one of the three conjugated $D^1$ to $D^3$ blocks is present in the compound.

The inventors of the present invention have recognized that even compounds having just one of the three conjugated $D^1$ to $D^3$ blocks together with the two five-membered rings surrounding them and the acceptor groups $A^1$ and $A^2$ exhibit excellent absorption in the short-wave region of the visible spectrum. Compared to compounds having more than one conjugated block, they are additionally more easily preparable since fewer synthesis steps are required. More particularly, they also have a lower molecular weight than analogous compounds having more than one conjugated block and usually have good evaporability for that reason. It has been shown, for example, that many of these compounds can be evaporated under reduced pressure without leaving a residue. For this reason, these compounds generally have good depositability by means of gas phase deposition or other methods that entail prior evaporation or sublimation of the compound. It is thus possible to use the compounds on the industrial scale as well for production of photoactive organic electrical components with a low level of complexity and expense.

In a different embodiment, more than one of the three coefficients o, p and q is non-zero. For example, exactly two of the three coefficients may be 1 or all three coefficients are 1.

It is thus possible, for example, for exactly two of the three conjugated $D^1$ to $D^3$ blocks to be present, or exactly three of the conjugated $D^1$ to $D^3$ blocks. More conjugated blocks are also conceivable (when p>1).

The inventors of the present invention have recognized that the presence of more than one conjugated $D^1$ to $D^3$ block can facilitate processing in the liquid phase. This means that deposition of the compound in organic layers in the liquid phase can be conducted more easily when more than just one conjugated $D^1$ to $D^3$ block is present.

In a preferred embodiment of the invention, the compound has at least one conjugated $D^1$ to $D^3$ block which is not the structural unit:

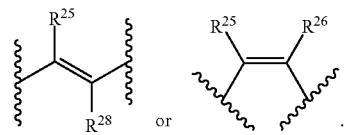

This is favorable for the absorption properties.

One embodiment of the invention relates to the compound of the invention having a molecular weight between about 300 and about 2000 g/mol, especially a molecular weight not less than 330 g/mol and not more than 1200 g/mol.

A preferred embodiment of the invention relates to the compound of the invention where $A^1$ is selected from the group of the following radicals:

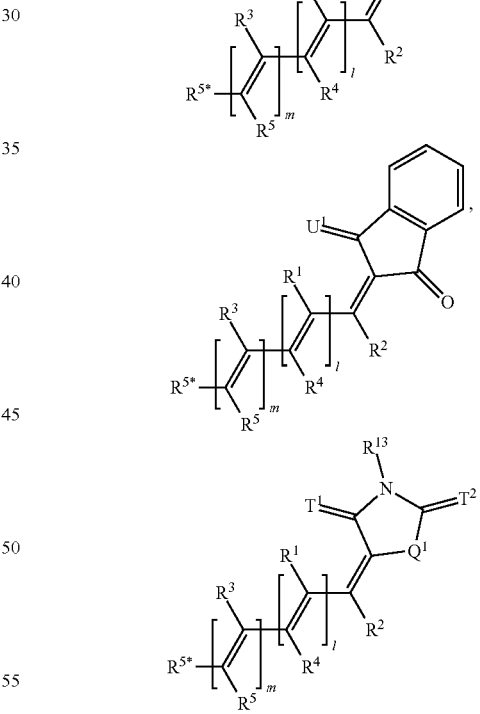

where, in each of these three radicals for $A^1$, either the E isomer or the Z isomer may each independently be present for each C=C double bond in each case. For each C=C double bond, either the E isomer ("E"=entgegen (opposite); i.e. trans configuration) or the Z isomer ("Z"=zusammen (together); i.e. cis configuration) may be present.

This is to be demonstrated hereinafter with reference to the example of the

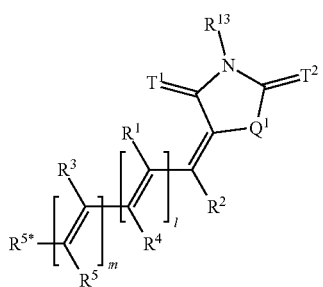

radical. Taking account of all E and Z isomers for the three C=C double bonds results in up to 8 stereoisomers for said radical:

Isomer 1

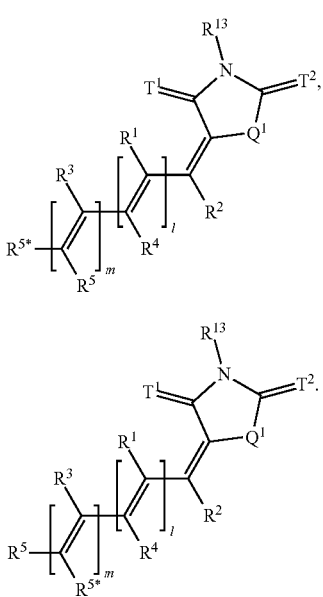

Isomer 2

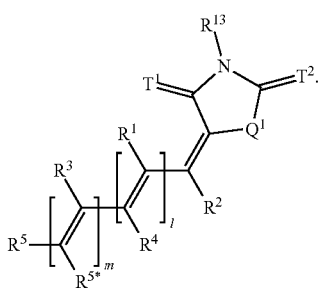

In isomer 1, the radicals on the first double bond, $R^{5*}$ and $R^3$, are arranged cis to one another, while $R^{5*}$ and $R^3$ in isomer 2 are arranged trans to one another (isomer 2 can be obtained from isomer 1 by implementing a notional rotation by 180° about the first of the three C=C double bonds).

Isomer 3

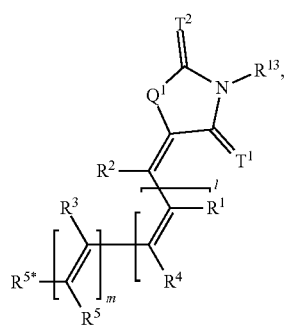

Isomer 4

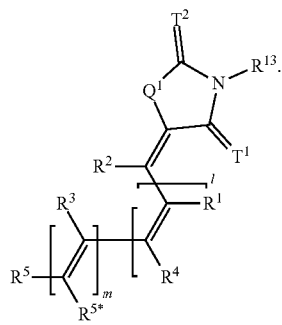

In isomer 1, $R^1$ and $R^4$ are arranged trans to one another, while they are arranged cis to one another in isomer 3 (isomer 3 can be obtained from isomer 1 by implementing a notional rotation by 180° about the second of the three C=C double bonds). In isomer 3, as in isomer 1, $R^{5*}$ and $R^3$ on the first C=C double bond are in cis positions. In isomer 4, $R^{5*}$ and $R^3$, by contrast, are in trans positions (isomer 4 can be obtained from isomer 3 by implementing a notional rotation by 180° about the first of the three C=C double bonds).

Isomer 5

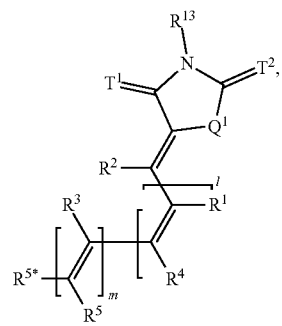

Isomer 6

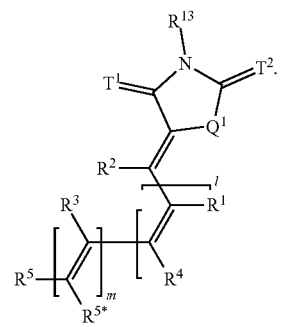

In isomer 3, $Q^1$ and $R^2$ are arranged cis to one another, while they are arranged trans to one another in isomer 5 (isomer 5 can be obtained from isomer 3 by implementing a notional rotation by 180° about the third of the three C=C double bonds). In isomer 5, as in isomer 1, $R^{5*}$ and $R^3$ on the first C=C double bond are in cis positions. In isomer 6, $R^{5*}$ and $R^3$, by contrast, are in trans positions (isomer 6 can be obtained from isomer 5 by implementing a notional rotation by 180° about the first of the three C=C double bonds).

Isomer 7

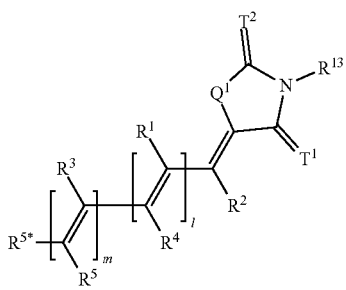

Isomer 8

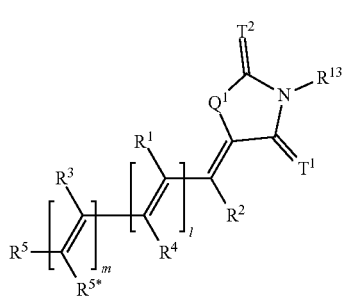

In isomer 1, $Q^1$ and $R^2$ are arranged cis to one another, while they are arranged trans to one another in isomer 7 (isomer 7 can be obtained from isomer 1 by implementing a notional rotation by 180° about the third of the three C=C double bonds). In isomer 7, as in isomer 1, $R^{5*}$ and $R^3$ on the first C=C double bond are in cis positions. In the case of isomer 8, $R^{5*}$ and $R^3$, by contrast, are in trans positions (isomer 8 can be obtained from isomer 7 by implementing a notional rotation by 180° about the first of the three C=C double bonds). In an analogous manner, for the other two specified radicals of $A^1$ and, there may in each case be up to 8 stereoisomers as result from the E-Z isomerism in the up to three C=C double bonds. The stereoisomers are not shown explicitly merely for the sake of conciseness, but have a comparable effect with regard to their electronic properties. However, preference is given to the three radicals shown explicitly for $A^1$.

In this case, the coefficients m and l are each independently 0 or 1. For example, both coefficients may simultaneously be 0 or both may at the same time be 1. Preferably, exactly one of the two coefficients is 1 and the other of the two coefficients is 0.

$A^2$ is selected from the group of the following radicals:

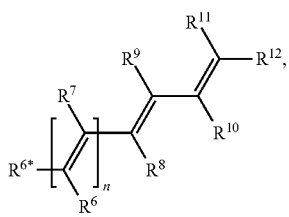

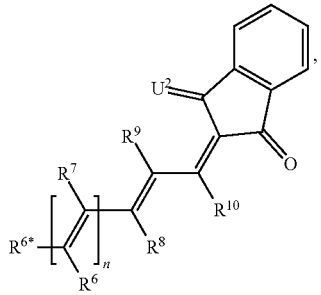

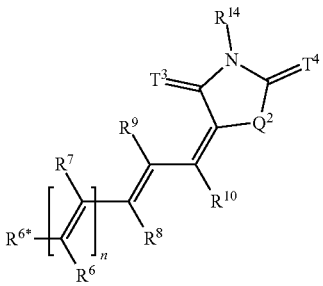

where, in each of these three radicals for $A^2$, either the E isomer or the Z isomer may each independently be present for each C=C double bond in each case.

In an analogous manner to that already shown for A1 above, for the three radicals of A1 shown, there may be up to stereoisomers as result from the E-Z isomerism in the up to 3 C=C double bonds. The stereoisomers are not shown explicitly merely for the sake of conciseness, but have a comparable effect with regard to their electronic properties. However, preference is given to the three radicals shown explicitly for $A^2$.

In this case, the coefficient n in each case is 0 or 1. Preferably, n is zero.

The $R^1$ to $R^{10}$ and $R^{5*}$ and $R^{6*}$ radicals, for the $A^1$ and $A^2$ groups, are each independently selected from the group of the following radicals:

H,
halogen,
CN,
cyclic or open-chain $C_1$-$C_{20}$-alkyl,
cyclic or open-chain $C_2$-$C_{20}$-alkenyl,
cyclic or open-chain $C_1$-$C_{20}$—O-alkyl,
aryl,
heteroaryl,
where hydrogen atoms in the alkyl, alkenyl, O-alkyl, aryl and heteroaryl radicals may each independently be substituted and where it is possible in each case independently for a ring to be formed by the following pairs of radicals together: $R^1$ and $R^3$, $R^2$ and $R^4$, $R^4$ and $R^5$, $R^3$ and $R^{5*}$, $R^7$ and $R^9$, $R^6$ and $R^8$, $R^8$ and $R_{10}$, $R^{6*}$ and $R^7$.

This applies in each case to the three radicals shown above and in the claim for $A^1$ and to the three radicals shown for $A^2$. It will be apparent to the person skilled in the art that a corresponding bridge or ring formation is equally possible in the E and Z isomers that have not been shown explicitly. Corresponding ring formation means here in each case that radicals arranged in cis positions to one another on a C=C double bond of $A^1$ can form a ring with one another. In addition, a radical attached to an atom group of $A^1$ which is attached to a C=C double bond of $A^1$ and is cis to a further radical on the same double bond can form a ring with this further radical. The same applies in each case to $A^2$. In other words: radicals ($R^1$ to $R^{10}$) that are on the same side of the conjugated backbone of one of the $A^1$ or $A^2$ radicals and are in 1,2 positions to one another—on a C=C double bond—or in 1,3 positions—on a C=C—C structural unit, i.e. are spatially adjacent, can form a ring with one another.

The statements made so far with regard to the $A^1$ and $A^2$ radicals are applicable with the proviso that, for $A^1$, exactly one of the $R^{5*}$, $R^5$, $R^4$, $R^3$, $R^2$ and $R^1$ radicals represents a linkage by means of which $A^1$ is bonded to the structural element

of the compound of the general formula (I), and with the further proviso that, for $A^2$, exactly one of the $R^{6*}$, $R^6$, $R^7$, $R^8$, $R^9$ and $R^{10}$ radicals represents a linkages by means of which $A^2$ is bonded to the structural element

of the compound of the general formula (I).

Preferably, exactly one of the $R^{5*}$, $R^5$ and $R^4$ radicals is the linkage which $A^1$ is bonded to the structural element

of the compound of the general formula (I). More particularly, the $R^{5*}$ radical is the linkage .

Preferably, exactly one of the $R^{6*}$, $R^6$ and $R^8$ radicals is the linkage by which $A^2$ is bonded to the structural element

of the compound of the general formula (I). More particularly, the $R^{6*}$ radical is the linkage s.

As specified, for $R^1$ to $R^{10}$ and $R^{5*}$ and $R^{6*}$, hydrogen atoms in the alkyl, alkenyl, O-alkyl, aryl and heteroaryl radicals may each independently be substituted. For example, hydrogen atoms may be replaced by halogen atoms, for example fluorine atoms.

In the case of formation of a ring by pairs of radicals, the ring may be a substituted or unsubstituted five-, six- or seven-membered ring. For example, it may be a cyclopentene, cyclohexene or cycloheptene ring.

The terms halogen, CN, cyclic or open-chain $C_1$-$C_{20}$-alkyl, cyclic or open-chain $C_2$-$C_{20}$-alkenyl, cyclic or open-chain $C_1$-$C_{20}$—O-alkyl, aryl and heteroaryl should each likewise be understood as already elucidated in connection with the $R^a$ to $R^c$ radicals.

The $R^{11}$ and $R^{12}$ radicals for the $A^1$ and $A^2$ groups are each independently selected from the group of the radicals:

H,
CN,
COOR$^f$ where R$^f$ is selected from the group of radicals: H and cyclic or open-chain $C_1$-$C_{20}$-alkyl, where hydrogen atoms in the alkyl may be replaced by fluorine atoms, with the proviso that $R^{11}$ and $R^{12}$ cannot both at the same time be H.

For example, exactly one of the $R^{11}$ or $R^{12}$ radicals may be CN and the other of the two radicals may be H. More particularly, it is also possible that $R^{11}$ and $R^{12}$ are both CN. It is likewise possible, for example, for one of the $R^{11}$ or $R^{12}$ radicals to be COOR$^f$ and for the other of the two radicals to be H or CN. It is also possible for both radicals at the same time to be COOR$^f$.

The $R^{13}$ and $R^{14}$ radicals, for the $A^1$ and $A^2$ groups, are each independently selected from the same group of radicals as $R^d$ and $R^e$.

$U^1$, $U^2$ and $T^1$ to $T^4$, for the $A^1$ and $A^2$ groups, are each independently selected from the group consisting of:
O,
S and
$C(CN)_2$.

For example, $U^1$ and $U^2$ may each be the same. For example, $U^1$ and $U^2$ may each be O or each be S. For example, is also possible for each of $T^1$ to $T^4$ to be the same. For example, $T^1$ to $T^4$ may each be O. For example, $T^1$ to $T^4$ may also each be S.

$Q^1$ and $Q^2$ for the $A^1$ and $A^2$ groups are each independently selected from the group consisting of O and S.

For example, $Q^1$ and $Q^2$ may be the same. For example, $Q^1$ and $Q^2$ may each be O or each be S.

When $A^1$ and $A^2$ are chosen as described in this embodiment, this has a particularly favorable effect on the absorption properties.

A particularly preferred embodiment relates to the compound of the invention where, for $A^1$, the $R^{5*}$ radical represents the linkage by means of which $A^1$ is bonded to the structural element

of the compound of the general formula (I), such that $A^1$ is selected from the group of the following radicals:

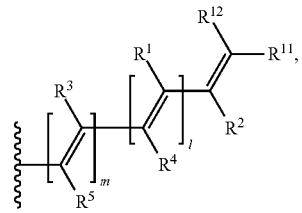

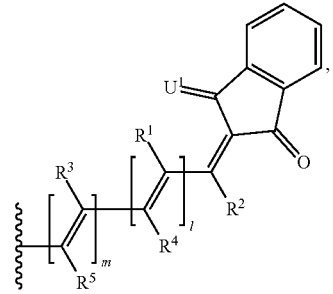

-continued

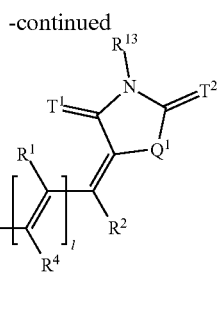

where, in each of these three radicals for $A^1$, for each C=C double bond independently, either the E isomer or the Z isomer may be present.

In addition, in this embodiment, for $A^2$, the $R^{6*}$ radical represents the linkage by means of which $A^2$ is bonded to the structural element

of the compound of the general formula (I), such that $A^2$ is selected from the group of the following radicals:

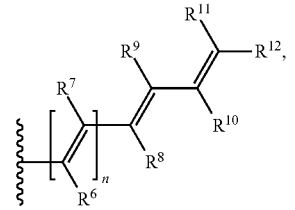

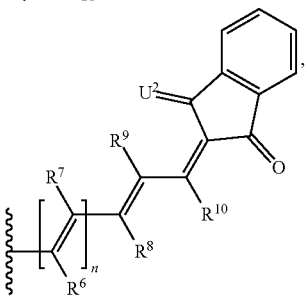

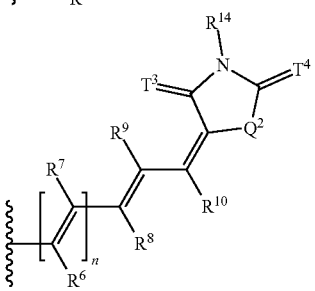

where, in each of these three radicals for $A^2$, for each C=C double bond independently, either the E isomer or the Z isomer may be present.

In a preferred embodiment of the invention, the compound of the formula (I) is symmetric, for example mirror-symmetric. More particularly, the molecule may have a mirror plane at right angles to the longitudinal axis of the molecule. In that case, the synthesis of the compound of the invention can be simplified.

In one embodiment of the compound according to the invention, the two electron-withdrawing groups $A^1$ and $A^2$ are each identical. It has been found that a certain degree of symmetry or virtually symmetric structures often show particularly favorable absorption properties. In many cases, this also facilitates the synthesis of the compound.

A development of the invention has, as $A^1$,

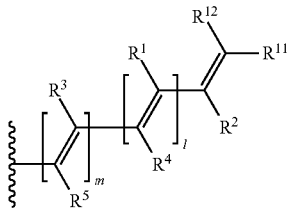

and, as $A^2$,

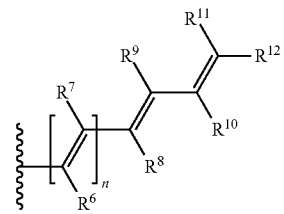

Compounds having these side chains are readily obtainable by means of Knoevenagel condensation. The preparation thereof is technically simple to implement. Moreover, these groups are good acceptors, especially when at least one of the two $R^{11}$ or $R^{12}$ radicals is CN.

A preferred development of the invention relates to the compound of the invention where each of the $R^{11}$ and $R^{12}$ radicals is CN.

By virtue of the total of four nitrile groups in this case, it is possible to achieve a particularly good acceptor effect of the two $A^1$ and $A^2$ groups. The acceptor effect is of significance for the position of the energy levels which essentially determine the absorption properties. With compounds of the form described, it was possible to observe particularly good absorption in the high-energy region of visible light as well, in interplay with the other molecular units of the compound of the invention.

A preferred form of the invention is the compound of the invention where the $R^1$ to $R^{10}$ and $R^{5*}$ and $R^{6*}$ radicals are each independently selected from the group of the following radicals:

H,

F, $C_1$-$C_5$-alkyl, where hydrogens in the alkyl may each independently be replaced by fluorine atoms.

Here too, in accordance with the general structure of the compound of the invention, the proviso is applicable that, for $A^1$, exactly one of the $R^{5*}$, $R^5$, $R^4$, $R^3$, $R^2$ and $R^1$ radicals represents a linkage by means of which $A^1$ is bonded to the structural element

of the compound of the general formula (I). In addition, correspondingly, the proviso is applicable that, for $A^2$, exactly one of the $R^{6*}$, $R^6$, $R^7$, $R^8$, $R^9$ and $R^{10}$ radicals represents a linkage by means of which $A^2$ is bonded to the structural element

of the compound of the general formula (I).

Preferably, the attachment of $A^1$ is again by means of $R^{5*}$, $R^5$ and $R^4$, especially $R^{5*}$. Likewise preferably, the attachment of $A^2$ is by means of $R^{6*}$, $R^6$ and $R^8$, especially $R^{6*}$.

In this embodiment too, in accordance with the general structure of the compound of the invention, the following pairs of radicals: $R^1$ and $R^3$, $R^2$ and $R^4$, $R^4$ and $R^5$, $R^3$ and $R^{5*}$, $R^7$ and $R^9$, $R^6$ and $R^8$, $R^8$ and $R^{10}$, $R^{6*}$ and $R^7$ may form a ring with one another. The ring may especially be a five-, six- or seven-membered ring. For example, it may be a cyclopentene, cyclohexene or cycloheptene.

The $C_1$-$C_5$-alkyl may in each case also be linear or branched. The alkyl radical may also be partly or fully fluorinated, preferably perfluorinated, but may also be free of fluorine atoms.

The compound of the invention does not require any long-chain $R^1$ to $R^{10}$ and $R^{5*}$ and $R^{6*}$ radicals. Instead, the inventors have observed that the desired high absorption can also be achieved with the radicals described here. This can be advantageous when the compound is to be evaporable for the purpose of processing without thermal breakdown. Moreover, compounds having the radicals mentioned, which are of comparatively small size, are preparable with higher atom efficiency and usually also more easily synthesizable than compounds with larger $R^1$ to $R^{10}$ and $R^{5*}$ and $R^{6*}$ radicals.

In one embodiment of the present invention, the compound of the invention has $R^1$ to $R^{10}$ and $R^{5*}$ and $R^{6*}$ radicals, at least one of which is a fluorine atom or a fluorinated alkyl. Preferably, at least two or even more of the $R^1$ to $R^{10}$ radicals are fluorine atoms or fluorinated alkyl radicals. The introduction of electron-withdrawing fluorine can affect the position of the energy levels of the molecular orbitals.

In another development, at least four of the $R^1$ to $R^{10}$ and $R^{5*}$ and $R^{6*}$ radicals are hydrogen atoms, preferably at least six. In this case, the electron-withdrawing $A^1$ and $A^2$ groups are generally preparable in a particularly simple manner.

A particularly preferred embodiment of the compound of the invention has an $A^1$ selected from the group of the following radicals:

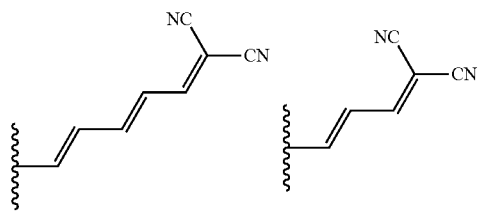

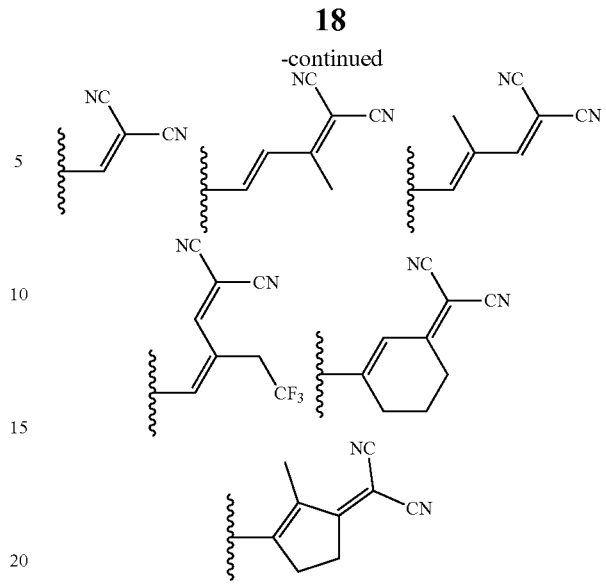

These groups for $A^1$ are excellent acceptors, have a good electron-withdrawing effect, are preparable without any great complexity and have been found to be useful for the preparation of compounds having particularly good absorption properties.

A likewise particularly preferred embodiment of the compound of the invention has an $A^2$ selected from the group of the following radicals:

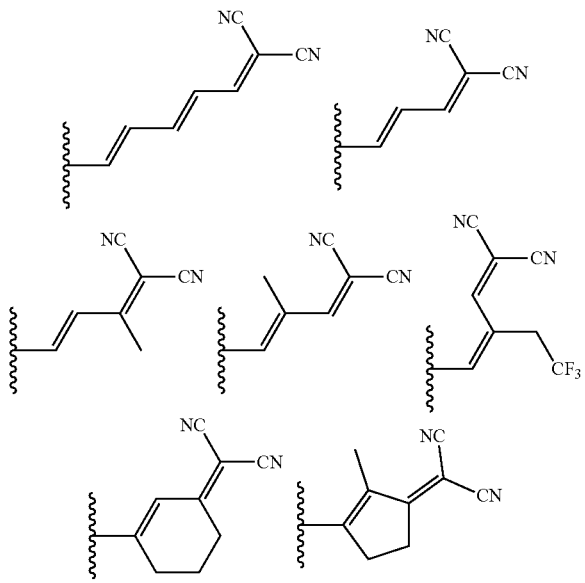

These groups for $A^2$ are excellent acceptors, have a good electron-withdrawing effect, are preparable without any great complexity and have been found to be useful for the preparation of compounds having particularly good absorption properties.

A particularly preferred embodiment of the invention relates to the compound of the invention where X is oxygen (O). In this case, each of the five-membered rings which surround the middle conjugated $D^1$ to $D^3$ blocks has an oxygen atom in the ring. For example, the two five-membered rings may be furans.

By virtue of the fact that oxygen is chosen for X, there is an increase in the symmetry of the compound. The symmetry of compounds often plays an important role in electron transitions. The inventors of the present invention have recognized that the compounds with X=O exhibit particularly good absorption properties. The structural element comprising X may, for example, be a furan.

For example, it has been found that the use of two furans for the outer five-membered rings leads to higher absorption than is the case with thiophenes.

A preferred embodiment of the present invention relates to the compound of the invention with X=oxygen, with m=n=0, with o=q=0 and with p selected from: 1, 2, 3, 4 and 5, having the general formula:

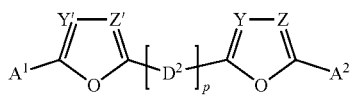

Compounds of this kind are obtainable with a low level of technical complexity and have particularly good absorption properties. They are of good suitability for use, for example, in photoactive organic components.

A particularly preferred embodiment of the present invention relates to the compound of the invention where X is oxygen and where the coefficients m, n, o and q are each zero. In addition, p is selected from 1, 2, 3, 4 and 5. A compound of this kind has the following general formula:

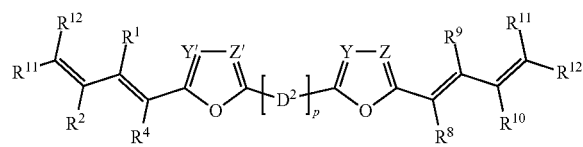

A compound of this formula has two acceptors $A^1$ and $A^2$ that are similar or identical in terms of their basic structure, and two five-membered rings, each of which has an oxygen atom in the ring structure. Preferably, the two five-membered rings are furans, where the furans may also be substituted. Compounds of the formula described do not just have good synthetic obtainability and good suitability for the production of layers for photoactive organic electronic components, but also exhibit particularly good absorption properties, particularly for the wavelength range between 400 and 600 nm. Specifically for wavelengths below 500 nm, much higher absorptions are generally possible than with most conventional compounds. For example, with these compounds, stronger absorption is achievable than with comparable compounds in which the $D^2$-surrounding five-membered rings are thiophenes. The improved absorption can be utilized for the attainment of higher sensitivities of photodetectors or of light-sensitive field-effect transistors and especially for the achievement of a higher efficiency of organic solar cells. All these applications require organic compounds which, like the compound of the invention, can absorb and thus make it possible to utilize sunlight of different wavelength.

In a preferred embodiment of the two embodiments of the compound of the invention just mentioned, p=1. This is favorable, for example, if the compound is to be evaporable. When p=1, there are also fewer reaction steps required.

One development of the invention relates to the compound of the invention where Y, Y', Z and Z' are each independently selected from: N or $CR^a$ where $R^a$ is selected from the group of the following radicals:

H
F,
$C_2$-$C_5$-alkenyl,
$C_2$-$C_5$—O-alkenyl,
$C_2$-$C_5$—S-alkenyl,
$C_2$-$C_5$-alkynyl,
phenyl,
where hydrogen atoms in the alkyl, O-alkyl, S-alkyl, alkenyl, O-alkenyl, S-alkenyl, alkynyl and phenyl radicals may each independently be substituted, especially replaced by fluorine atoms.

The alkyl, O-alkyl, S-alkyl, alkenyl, O-alkenyl, S-alkenyl, alkynyl radicals may each also be linear or branched.

$R^a$ for each of the different placeholders Y, Y', Z and Z' may be chosen differently.

Further preferably, Y, Y', Z, Z' are each independently selected from: N, CH, C—F, C—$CH_3$, C—$CF_3$, C—$C_2H_5$, C—$C_3H_8$, C—$OCH_3$, C—$OC_2H_5$, C—$SCH_3$, C—$SC_2H_5$. Compounds having these radicals that are not very sterically demanding on the two five-membered rings often allow a technically less complex synthesis.

In one embodiment, at least one of the positions Y, Y', Z and Z' is N. The inventors have found that the presence of N at one of the Y, Y', Z and Z' positions leads controlled lowering of the highest molecular orbital occupied by electrons (HOMO). This allows the absorption spectrum of the compound of the invention to be shifted toward shorter wavelengths. When two or more of the Y, Y', Z and Z' positions are occupied by N, the effect is enhanced. Accordingly, it may also be preferable that exactly 2, 3 or even 4 of the Y, Y', Z and Z' positions are occupied by N.

Most preferably, Y, Y', Z, Z' are each CH. In this case, the two five-membered rings that surround the conjugated $D^1$ to $D^3$ blocks are each furan rings. This increases the symmetry of the molecule, which is a possible reason for the particularly favorable absorption properties of these compounds, without being bound by theory.

Another embodiment of the invention relates to the compound of the invention where the compound has at least one conjugated $D^1$ to $D^3$ block having at least one substituent, where the substituent is a fluorine atom or a fluoroalkyl. The inventors of the present invention have found that the fluorine substituents generally lead to a certain lowering of energy of the HOMO of the compound of the invention for each substituent. The extent of the effect depends on the size of the orbital coefficient of the HOMO on the respective carbon atom to which the fluorine substituent binds in the compound of the invention. This generally leads to a shift in the absorption spectrum toward shorter wavelengths. Finally, the inventors have also found that fluorine substituents can form S—F interactions with sulfur atoms of adjacent S-containing rings, which can promote higher coplanarity of the compound of the invention. This frequently improves the charge transport properties of the compound. This can also have a favorable effect on the absorption.

Another embodiment of the invention relates to the compound of the invention where the compound has at least one conjugated $D^1$ to $D^3$ block having at least one $C_1$-$C_{20}$-alkyl alkyl substituent, preferably $C_1$-$C_{10}$-alkyl, especially $C_1$-$C_5$-alkyl. The inventors of the present invention have found that alkyl substituents have an electron-donating effect to a minor degree. They can lead to a slight rise in the HOMO of the compound of the invention, the extent of the effect depending on the size of the orbital coefficient of the HOMO on the particular carbon atom to which the alkyl substituent binds in the compound of the invention.

Another embodiment of the invention relates to the compound of the invention where the compound has at least one conjugated $D^1$ to $D^3$ block having at least one O-alkyl substituent $C_1$-$C_{20}$—O-alkyl, preferably $C_1$-$C_{10}$—O-alkyl, especially $C_1$-$C_5$—O-alkyl. O-Alkyl substituents, i.e. alkoxy groups, feature a much more marked electron-donating effect much stronger than that of alkyl substituents. O-Alkyls thus lead to a rise in the HOMO. The introduction of O-alkyl substituents can enable a shift in the absorption spectrum toward longer wavelengths. Moreover, O-alkyl groups are less sterically demanding than alkyl groups and can contribute, via S—O or O—H interactions, to stiffening of the molecular structure of the compound of the invention.

Another embodiment of the invention relates to a compound of the invention where at least one of the conjugated $D^1$ to $D^3$ blocks that must be present in the compound has the general formula

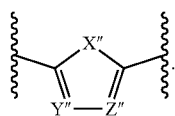

In this case, the compound has a total of at least three aromatic five-membered rings as part of a conjugated π-electron system. This combination has been found to be particularly favorable for the absorption properties in experiments.

In one embodiment, at least one of the Y" and Z" positions is N. The inventors have found that the presence of N at one of the Y" and Z" positions leads controlled lowering of the highest molecular orbital occupied by electrons (HOMO). The effects are comparable here with the effects described above for N at one of the Y, Y', Z and Z' positions.

It is particularly preferable in another embodiment when at least one of the conjugated $D^1$ to $D^3$ blocks that must be present in the compound has the general formula

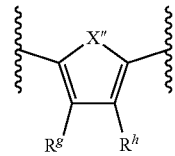

where the $R^g$ and $R^h$ radicals are independently selected from the group of the following radicals:

H
F,
$C_1$-$C_5$-alkyl, where individual carbon atoms may be replaced by heteroatoms,
$C_1$-$C_5$—O-alkyl,
$C_1$-$C_5$—S-alkyl,
where hydrogen atoms in the alkyl, O-alkyl and S-alkyl radicals may each independently be substituted by fluorine,
where the $R^g$ and $R^h$ radicals may be joined to one another in the form of a ring structure, and
where an aryl radical may be fused to the ring structure. The latter aryl radical may also be substituted, for example fluorinated.

The alkyl, O-alkyl and S-alkyl radicals may each also be linear or branched.

The ring structure may, for example, be a five-, six- or seven-membered ring which, as well as carbon atoms, may also have oxygen or sulfur atoms. The ring may thus be heterocyclic or homocyclic. The ring is preferably saturated. For example, the ring may be substituted. For example, the ring may have fluorine atoms or alkyl groups as substituents. The ring may also have at least partly fluorinated alkyl groups as substituents. The fluorination can achieve an electron-withdrawing effect.

In a preferred embodiment of the embodiment just mentioned, $R^g$ and $R^h$ are each independently selected from the group of the radicals, H, F, methyl, methoxy, ethyl, ethyloxy, propyl, propyloxy, where hydrogen atoms in each of methyl, methoxy, ethyl, ethyloxy, propyl and propyloxy may be substituted by fluorine.

Particular preference is given to compounds of the invention where X"=S. Preference is thus given to compounds of the invention having, for at least one of the three conjugated $D^1$ to $D^3$ blocks, a five-membered ring of the general formula

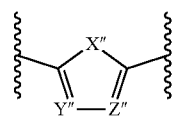

where X" is sulfur.

It is most preferable when the ring is a substituted or unsubstituted thiophene ring, i.e. when no further heteroatoms are present in the five-membered ring aside from sulfur.

The use of a five-membered ring including sulfur as one of the conjugated blocks for $D^1$ to $D^3$ for achievement of high absorption values at short wavelengths of visible light has been found to be particularly favorable experimentally.

A further particular embodiment of the invention relates to the compound of the invention where X is oxygen and where there is exactly one conjugated block of $D^1$ to $D^3$, i.e. exactly one of the coefficients o, p and q is 1, while the two others are each zero, in which the conjugated block is

where X" is sulfur. In this case, the compound is a compound of the following general formula:

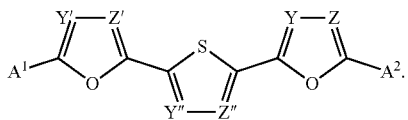

A combination of two outer five-membered rings each with an oxygen and a middle five-membered ring with sulfur in conjunction with the two acceptors $A^1$ and $A^2$ has been found to be a particularly suitable structural element in order to achieve the favorable absorption properties in the form of a readily obtainable and hence inexpensive compound.

A further embodiment relates to the compound of the invention where there is at least one of the conjugated $D^1$ to $D^3$ blocks in the compound and it has the general formula

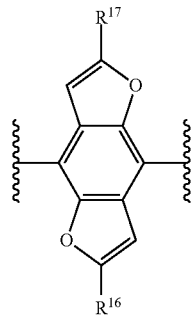

where $R^{17}$ and $R^{18}$ are independently selected from the group of the following radicals:
H,
F,
$C_1$-$C_5$-alkyl,
$C_1$-$C_5$—O-alkyl,
$C_1$-$C_5$—S-alkyl,
where hydrogen atoms in the alkyl, O-alkyl and S-alkyl radicals may each independently be replaced by fluorine atoms. The alkyl, O-alkyl and S-alkyl radicals here may each also be linear or branched.

The inventors of the present invention have observed that this structural element is of excellent suitability as one of the conjugated $D^1$ to $D^3$ blocks in order to obtain compounds having the desired high absorption properties.

Further preferably, $R^{17}$ and $R^{18}$ are each hydrogen, methyl, ethyl, methoxy, ethoxy. Most preferably, $R^{17}$ and $R^{18}$ are each hydrogen.

A development relates to the compound of the invention where there is at least one of the conjugated $D^1$ to $D^3$ blocks in the compound and it has the general formula

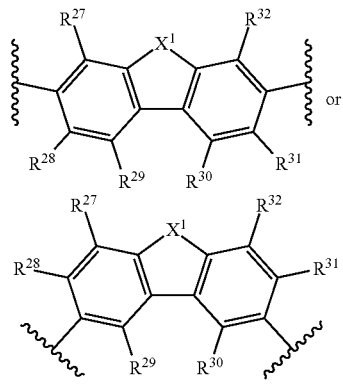

where $X^1$ is selected from: $NR^l$, $CR^l R^m$,
where $R^l$ and $R^m$ are each independently selected from the group of the radicals:
H,
open-chain $C_1$-$C_5$-alkyl,
$C_5$-$C_{12}$-aryl
$C_5$-$C_{12}$-heteroaryl
where hydrogen atoms in the open-chain $C_1$-$C_5$-alkyl may at least partly be replaced by fluorine atoms, and where hydrogen atoms in the $C_5$-$C_{12}$-aryl and the $C_5$-$C_{12}$-heteroaryl may be substituted, for example by fluorine atoms, and
where the open-chain $C_1$-$C_5$-alkyl may be linear or branched, and
where $R^{27}$ to $R^{32}$ are independently selected from the group of the following radicals:
H,
F,
$C_1$-$C_5$-alkyl,
$C_1$-$C_5$—O-alkyl,
$C_1$-$C_5$—S-alkyl,
where hydrogen atoms in the alkyl, O-alkyl and S-alkyl radicals may each independently be replaced by fluorine atoms and where the radicals may each independently be linear or branched.

For example, the $C_5$-$C_{12}$-aryl is the $R^l$ radical and $R^m$ is a phenyl which may in turn be substituted.

A further embodiment relates to the compound of the invention where there is at least one of the conjugated $D^1$ to $D^3$ blocks in the compound and it has the general formula

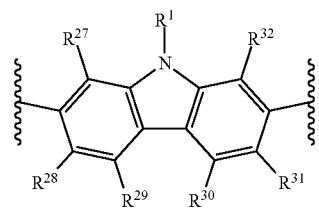

where $R^1$ is H or an open-chain $C_1$-$C_5$-alkyl or phenyl, and
where $R^{27}$ to $R^{32}$ are independently selected from the group of the following radicals:
H,
F,
$C_1$-$C_5$-alkyl,
$C_1$-$C_5$—O-alkyl,
$C_1$-$C_5$—S-alkyl,
where hydrogen atoms in the alkyl, O-alkyl and S-alkyl radicals may each independently be replaced by fluorine atoms. The alkyl, O-alkyl and S-alkyl radicals may each also independently be linear or branched.

The inventors of the present invention have observed that this structural element is of excellent suitability as one of the conjugated $D^1$ to $D^3$ blocks in order to obtain compounds having the desired high absorption properties. Just like fluorene, carbazole tends to lead to a short-wave shift in absorption and to a lowered HOMO compared to the use of a thiophene or furan as conjugated block. Carbazole is a stronger donor than fluorene, and so the HOMO of carbazole derivatives is usually higher than that of analogous fluorenes.

Preferably, $R^1$ is H, methyl, ethyl, propyl or butyl.

It is further preferable when $R^{27}$ to $R^{32}$ are each selected from the group comprising: H, F, methyl, ethyl, methoxy, ethoxy. For example, it is also possible for all $R^{27}$ to $R^{32}$ radicals to each be hydrogen.

A preferred development relates to the compound of the invention where there is at least one of the conjugated $D^1$ to $D^3$ blocks in the compound and it has the general formula

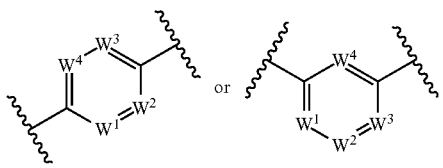

where $W^1$ to $W^4$ are independently selected from: N and $CR^n$, where $R^n$ is selected from the group of the following radicals:
H,
F,
$C_1$-$C_5$-alkyl,
$C_1$-$C_5$—O-alkyl,
$C_1$-$C_5$—S-alkyl, where hydrogen atoms in the alkyl, O-alkyl and S-alkyl radicals may each independently be replaced by fluorine atoms. The alkyl, O-alkyl and S-alkyl radicals may each also independently be linear or branched.

The inventors of the present invention have observed that this structural element is of excellent suitability as one of the conjugated $D^1$ to $D^3$ blocks in order to obtain compounds having the desired high absorption properties. Incorporation generally leads to a short-wave shift in absorption and lowered HOMO compared to the use of a thiophene or furan as conjugated block.

It is further preferable when $R^n$, for $W^1$ to $W^4$, is in each case independently selected from H, methyl, methoxy, ethyl, ethoxy, propyl, propyloxy.

A further development relates to the compound of the invention where there is at least one of the conjugated $D^1$ to $D^3$ blocks in the compound and it has the general formula

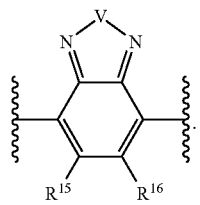

$R^{15}$ and $R^{16}$ here are preferably selected from the group of the following radicals:
H,
F,
$C_1$-$C_5$-alkyl,
$C_1$-$C_5$—O-alkyl,
$C_1$-$C_5$—S-alkyl, where hydrogen atoms in the alkyl, O-alkyl and S-alkyl radicals may each independently be replaced by fluorine atoms. The alkyl, O-alkyl and S-alkyl radicals may each also independently be linear or branched.

For example, $R^{15}$ and $R^{16}$ may be H, F, methyl, ethyl, methoxy and ethoxy.

The inventors of the present invention have recognized that this structural element is likewise suitable as one of the conjugated $D^1$ to $D^3$ blocks in order to obtain compounds having good absorption properties. Incorporation of this structural element generally leads to improved co-planarity with respect to the neighboring structural units. A shift in the absorption spectrum toward longer wavelengths can thus be brought about in a controlled manner.

In a preferred embodiment of the embodiment just mentioned, V is sulfur or $NR^k$ where $R^k$ is selected from the group of H and $C_1$-$C_5$-alkyl.

A preferred development of the invention relates to the compound of the invention where there is at least one of the conjugated $D^1$ to $D^3$ blocks in the compound and it has the general formula

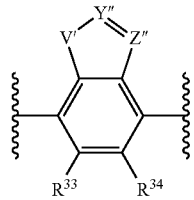

where $R^{33}$ to $R^{34}$ are each independently selected from the group of the following radicals:
H,
F,
$C_1$-$C_5$-alkyl,
$C_1$-$C_5$—O-alkyl,
$C_1$-$C_5$—S-alkyl, where hydrogen atoms in the alkyl, O-alkyl and S-alkyl radicals may each independently be replaced by fluorine atoms, and where V' is selected from: O, S, Se or $NR^k$;
where Y" is selected from: N or $CR^g$;
where Z" is selected from: N or $CR^h$;
where $R^k$ is selected from the group of the radicals:
H,
open-chain $C_1$-$C_5$-alkyl,
$C_5$-$C_{12}$-aryl
$C_5$-$C_{12}$-heteroaryl where hydrogen atoms in the open-chain $C_1$-$C_5$-alkyl may at least partly be replaced by fluorine atoms and where hydrogen atoms in the $C_5$-$C_{12}$-aryl and the $C_5$-$C_{12}$-heteroaryl may at least partly be substituted, where $R^g$ and $R^h$ are selected independently like $R^a$.

The inventors of the present invention were able to observe that compounds of this kind have particularly high absorption and are of surprisingly good suitability for use in photoactive organic components.

In a preferred embodiment of the development just mentioned, the $R^{33}$ to $R^{34}$ radicals are each independently selected from the group of: H, F, methyl, ethyl, methoxy and ethoxy, where methyl, ethyl, methoxy and ethoxy may each be at least partly fluorinated. For example, $R^{33}$ to $R^{34}$ are each hydrogen.

In a preferred embodiment, $R^k$ is hydrogen.

A preferred development relates to the compound of the invention where there is at least one of the conjugated $D^1$ to $D^3$ blocks in the compound and it has the general formula

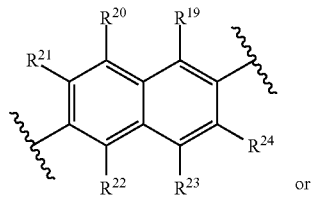

or

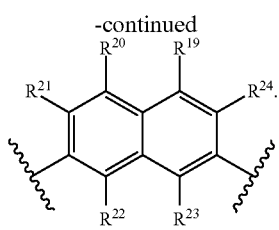

$R^{19}$ to $R^{24}$ here are preferably selected from the group of the following radicals:

H,
F,
$C_1$-$C_5$-alkyl,
$C_1$-$C_5$—O-alkyl,
$C_1$-$C_5$—S-alkyl,
where hydrogen atoms in the alkyl, O-alkyl and S-alkyl radicals may each independently be replaced by fluorine atoms. The alkyl, O-alkyl and S-alkyl radicals may in each case also independently be linear or branched.

For example, $R^{19}$ to $R^{24}$ may be H, F, methyl, ethyl, methoxy, ethoxy, propyl and propyloxy.

The inventors of the present invention have recognized that this structural element is likewise suitable as one of the conjugated $D^1$ to $D^3$ blocks in order to obtain compounds having good absorption properties. Naphthalene generally leads to absorption at shorter wavelengths and to a lowered HOMO compared to the use of a thiophene or furan as conjugated block.

A further embodiment of the invention relates to the compound of the invention where there is at least one of the conjugated $D^1$ to $D^3$ blocks in the compound and has the general formula

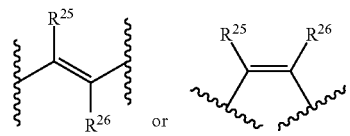

$R^{25}$ and $R^{26}$ may each independently preferably be selected from the group of the following radicals:

H,
F,
$C_1$-$C_5$-alkyl,
$C_1$-$C_5$—O-alkyl,
$C_1$-$C_5$—S-alkyl,
where hydrogen atoms in the alkyl, O-alkyl and S-alkyl radicals may each independently be replaced by fluorine atoms. The alkyl, O-alkyl and S-alkyl radicals may each also independently be linear or branched.

For example, $R^{25}$ and $R^{26}$ may be H, F, methyl, ethyl, methoxy and ethoxy. Particular preference is given to H, F and methyl.

In another embodiment, at least one of the conjugated $D^1$ to $D^3$ blocks is only a structural unit of the general formula

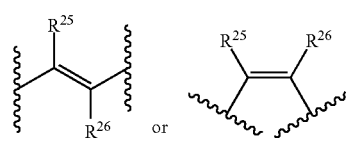

if there is at least one further donor $D^1$ to $D^3$ which is not a conjugated block of the structural unit

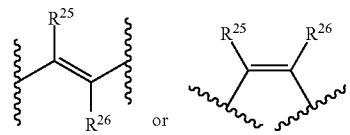

A particularly preferred embodiment of the present invention relates to the compound of the invention where the conjugated $D^1$ to $D^3$ blocks are each independently selected from the group of the following structural units:

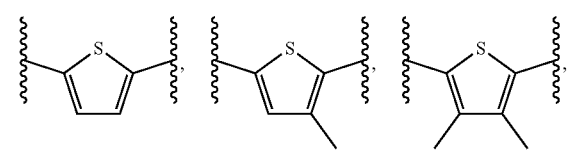

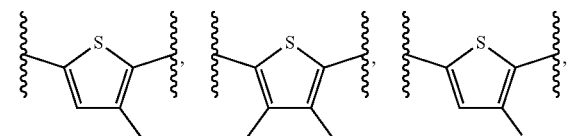

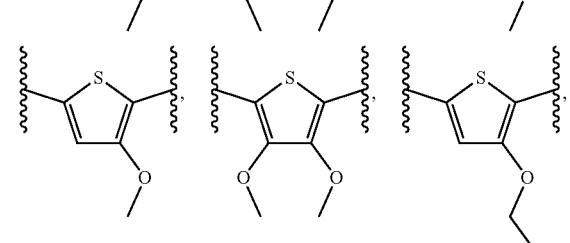

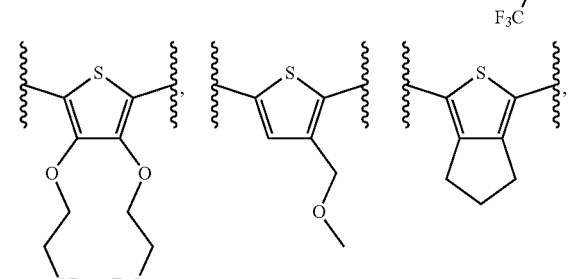

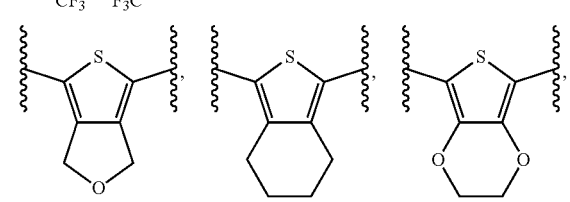

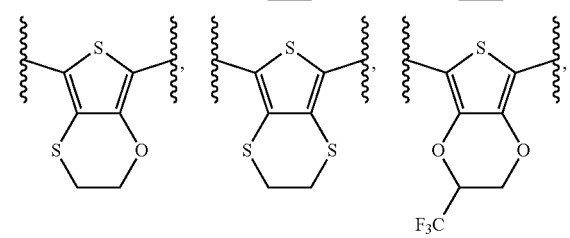

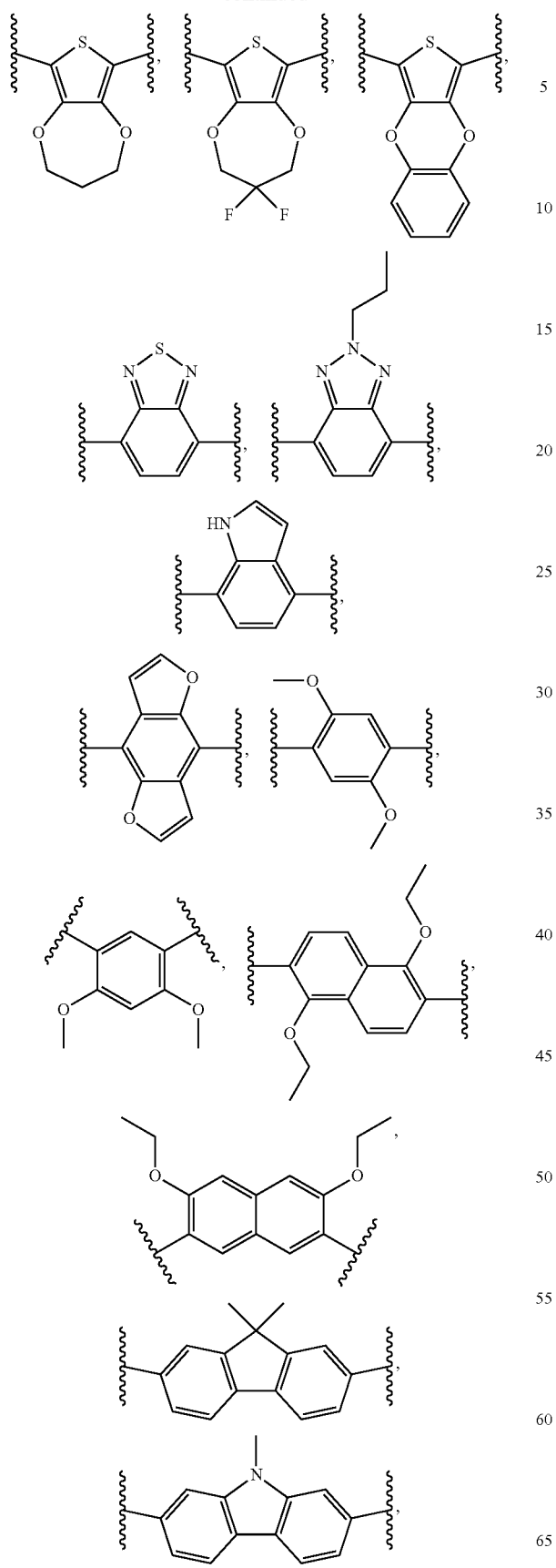
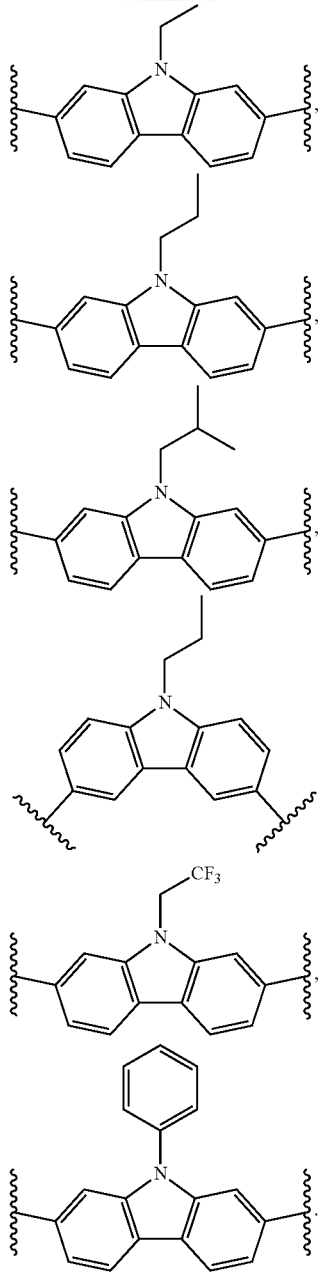

The inventors of the present invention have observed that compounds having one of these conjugated blocks for $D^1$ to $D^3$ have unexpectedly high absorption in the short-wave range, particularly for wavelengths less than 500 nm, which generally distinctly exceed the absorption of conventional compounds.

The present invention relates not only to the compound of the invention but additionally to the use of the compound of the invention in a photoactive organic electronic component.

Photoactive organic electronic components convert electromagnetic radiation to electrical energy. This principle is applied in various kinds of photoactive organic electronic component. The use of compounds of the invention that exhibit particularly high absorption over the entire wavelength range of visible light and additionally utilize short-wave visible light (about 400 to 600 nm) more effectively than conventional organic compounds, merely owing to their excellent absorption properties, are already of excellent suitability for use in photoactive organic electronic components. High-energy photons can also be absorbed and hence trigger electron transitions. Since the compounds of the invention can better absorb higher-energy photons, they utilize the short-wave spectrum of visible light more efficiently. With the use of the compound of the invention, it is thus possible to improve the efficiency and sensitivity of photoactive organic electronic components.

For instance, in the case of photodetectors that utilize the compounds of the invention, better sensitivity may be enabled than in the case of comparable photodetectors with conventional organic compounds that do not exhibit the favorable absorption properties of the compound of the invention. For example, the compounds of the invention, as well as photodetectors, can also be used for light-sensitive field-effect transistors. Use in the field of photo-conductors for printing and copying machines is also conceivable.

Analogously, it is also possible in other photoactive organic electronic components to enhance sensitivity or efficiency through the use of the compounds of the invention.

It is most preferable here to use the compound of the invention in a photoactive organic electronic component which is an organic solar cell. The efficient utilization of visible light with short wavelengths as well with the compounds of the invention makes it possible to produce organic solar cells with a higher efficiency than solar cells based on the basis of organic compounds that do not feature these favorable absorption properties.

Moreover, the compounds of the invention also have adequate charge carrier transport properties that make them suitable for use in photoactive organic electronic components in general and for organic solar cells in particular.

The present invention also relates to a photoactive organic electronic component comprising the compound of the invention.

As just described, the inventors of the present invention have found that the compounds of the invention, owing to their absorption properties, are of excellent suitability for use in photoactive organic electronic components.

In a preferred embodiment, the photoactive organic electronic component has a photoactive layer, for example a light-sensitive layer comprising the compound of the invention.

In a further embodiment, the photoactive organic electronic component has at least two electrodes between which the photoactive layer is disposed.

In a further embodiment, the component has further layers, especially charge transport layers, for instance electron transport layers and hole transport layers.

In a further embodiment, the component has a substrate. More particularly, one of the electrodes of the component may be mounted on the substrate.

In a further embodiment, the photoactive organic electronic component comprises organic solar cells, photodetectors, solution-processed solar cells, xerographic layers, photoconductors for printing or copying machines.

In a particularly preferred embodiment, the photoactive organic electronic component is an organic solar cell. Solar cells comprising the compound of the invention enable particularly efficient utilization of the short-wave spectrum of visible light.

In a development of the organic solar cell just described, the organic solar cell has a photoactive region having at least one organic donor material in contact with at least one organic acceptor material, wherein the donor material and the acceptor material form a donor-acceptor heterojunction, specifically also what is called a bulk heterojunction (BHJ), and wherein the photoactive region comprises at least one compound of the formula I.

For example, the compound of the invention can be used a standard setup of organic solar cells as described in the literature.

A setup already known from the literature for a standard organic solar cell consists, for example, in pin or nip diodes [Martin Pfeiffer, "Controlled doping of organic vacuum deposited dye layers: basics and applications", PhD thesis TU-Dresden, 1999 and WO 2011 161 108]: a pin solar cell consists here of a carrier/substrate with an adjoining, usually transparent base contact, p layer(s), i layer(s), n layer(s) and a top contact. A nip solar cell consists of a carrier/substrate with an adjoining, usually transparent base contact, n layer(s), i layer(s), p layer(s) and a top contact.

Means here that n or p doping leads to an increase in the density of free electrons/holes in the thermal equilibrium state. Thus, layers of this kind should be regarded primarily as transport layers. It is also possible that n or p layers are at least partly nominally undoped and have preferably electron-conducting or hole-conducting properties only by virtue of the material properties (for example different mobility) or owing to different impurities (for example remaining residues from the synthesis or the layer production) or through environmental influences (for example adjoining layers, inward diffusion of metals or other organic materials, gas doping from the surrounding atmosphere). In this context, layers of this kind should preferably be regarded as transport layers.

The excitons arrive via diffusion at an interface of this kind, where electrons and holes are separated from one another. The material that accepts the electrons is referred to as acceptor, and the material that absorbs the holes as donor.

The term "i layer" characterizes an undoped or intrinsic layer. One or more i layers may consist of one material (planar heterojunctions, PHJs) or of a mixture of two or more materials, called bulk hetero junctions (BHJs), which have an interpenetrating network.

Also known from the literature are organic pin tandem cells and pin multiple cells DE 10 2004 014 046. In this regard, WO 2011 161 108 A1 discloses a proposal for implementation in the form of a photoactive component with an electrode and a counterelectrode, wherein at least one organic layer system is disposed between the electrodes, and also with at least two photoactive layer systems and at least two different transport layer systems of the same charge carrier type between the photoactive layer systems, characterized in that one transport layer system is matched in terms of energy to one of the two photoactive layer systems and the other transport layer system is transparent.

The layers of the invention may especially be used as absorber material in said types of photoactive organic electronic components or in similar, commonly known photoactive organic electronic components in the respective absorber layer.

In a further embodiment, the photoactive organic electronic component is a single cell, a tandem cell, triple cell, quadruple cell or another multiple cell. "Tandem cell" in the present application is understood to mean that two functional cells are stacked one on top of another in spatial terms and are connected in series, where one or more interlayers may be arranged between the cells. A multiple cell or multi junction cell is likewise understood to mean that more than two functional cells are stacked one on top of another in spatial terms and are connected in series, where an interlayer may be arranged between the cells.

Preferably, the component consists of a combination of nip, ni, ip, pnip, pni, pip, nipn, nin, ipn, pnipn, pnin or pipn structures which of the multiple independent combinations containing at least one i layer are stacked one on top of another.

In a further development, the photoactive organic electronic component of the invention is a component including at least one layer comprising the compound of the invention, wherein the compound of the invention and/or said layer is deposited by means of vacuum processing, gas phase deposition or solution processing.

The invention additionally relates to a compound for the preparation of the compound of the invention, having the following general formula:

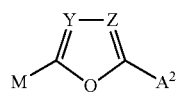

where Y, Z and $A^2$ are as defined in any of the preceding claims and where M is selected from one of the following functional groups:

—SnR*$_3$,—B(OR*)$_2$,—Zn-Hal*,—Mg-Hal*, where R* is a $C_1$-$C_{10}$-alkyl and where the Hal* group is a halogen. Halogen means F, Cl, Br and I, preferably Cl, Br and I.

The compound is an important starting material for the preparation of the inventive compound as claimed in claim 1.

The invention further relates to a process for preparing the compound of the invention. The process comprises, as a process step, a coupling reaction in which the compound of the general formula just described

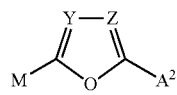

reacts with a further compound of the following general formula

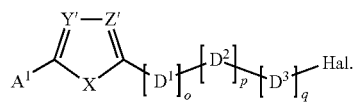

$A^1$, Y', Z', X, $D^1$ to $D^3$ and o, p and q are defined for the further compound as described for the compound of the invention. The Hal group is additionally a halogen. This may be F, Cl, Br and I, preferably Cl, Br and I, especially Br and I.

In a further embodiment of the process of the invention, the process comprises a coupling reaction in which two equivalents of the described compound having the general formula

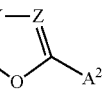

react with a further compound of the general formula

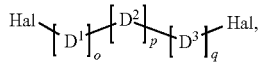

by means of which it is possible, by a simplified route, to prepare mirror-symmetric compounds of the invention in which X=O, Y=Y', Z=Z' and $A^1$=$A^2$.

The inventors of the present invention have found that the compounds of the invention are obtainable by means of coupling reactions in good yields and selectivities with acceptable experimental work.

In a preferred embodiment of the process of the invention, Pd-based catalysts are used in the coupling reaction. An example of particularly good suitability is Pd(PPh$_3$)$_4$.

Preferably, the coupling reaction in the process of the invention is a reaction selected from the group of the following coupling reactions: Stille coupling, Negishi coupling and Suzuki coupling. These coupling reactions have been found to be particularly suitable for the synthesis of the compounds of the invention.

The synthesis of the compounds of the invention is to be elucidated hereinafter in general and more particularly with reference to a number of specific examples. Advantageously, the compounds of the invention can be made available by a simple building block system easily and in good yields.

The schematic diagram below is a simplified representation of a synthesis route for compounds of the invention. The letter k here identifies a compound of the invention:

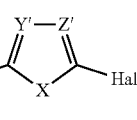

a

↓ e.g. Aldol, Wittig

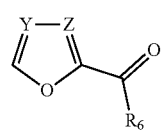

a'

↓ e.g. Aldol, Wittig

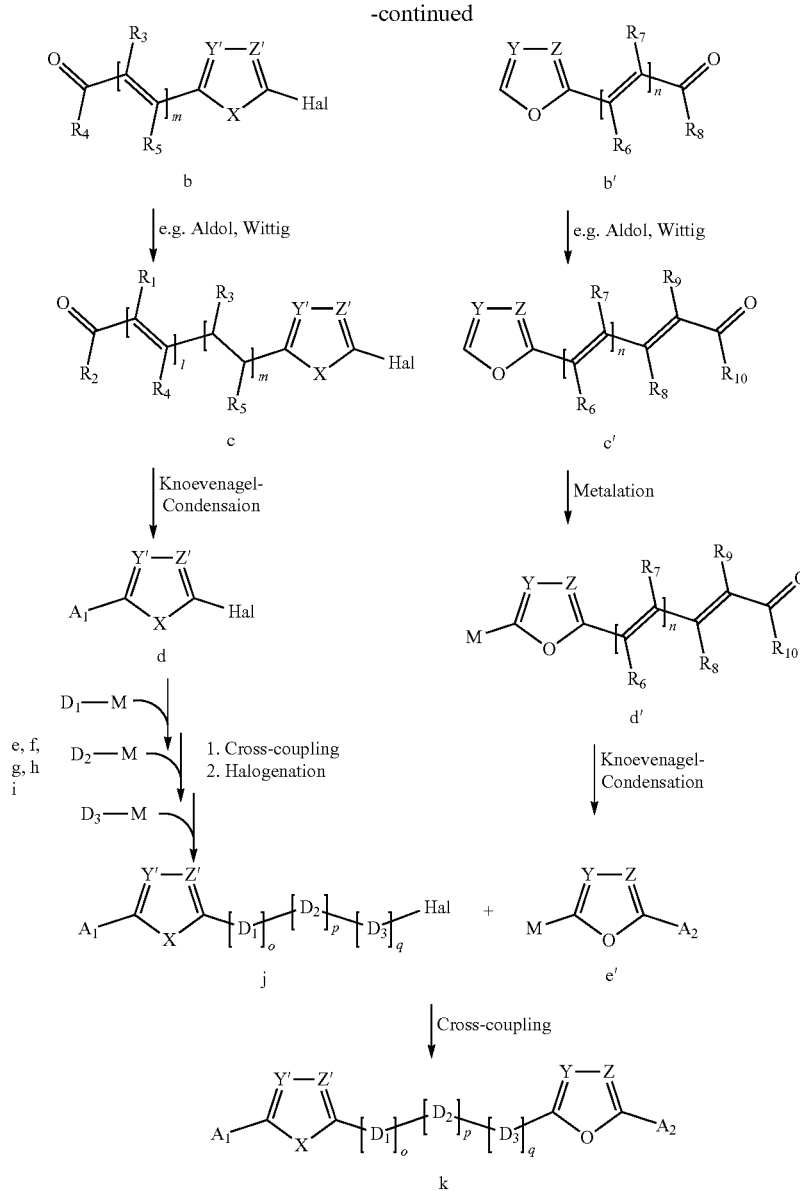

M may be selected here, for example, from one of the following functional groups:

—SnR*$_3$, —B(OR*)$_2$, —Zn-Hal*, —Mg-Hal*, where R* is a $C_1$-$C_{10}$-alkyl and where the Hal* group is a halogen (F, Cl, Br, I). The abbreviation Hal also represents a halogen selected from F, Cl, Br, I.

Compound a is commercially available, or can be prepared from commercially available synthons by the person skilled in the art by means of known methods (halogenation, acetylation or carbonylation). The conversion to b can be effected, for example, by an aldol reaction or Wittig reaction or other typical reactions for the generation of a double bond from a carbonyl function. The direct preparation of b from non-halogenated (hetero-)aromatic components, for example by Heck reaction, is also possible. For preparation of compound c, this step can be repeated as often as desired. Compound d can be prepared, for example, by a Knoevenagel condensation with a compound bearing a methylene unit.

In a series of cross-coupling reactions repeatable as often as desired, for example Suzuki, Negishi or Stille couplings and variants thereof, with subsequent introduction of a halogen atom (especially Cl, Br or I), the structural units $D^1$ to $D^3$ are incorporated into the structure of the compound. In this way, the intermediates e-j are obtained. Rather than the use of the metalated structural units $D^1$ to $D^3$, the use of non-metalated units $D^1$ to $D^3$, or of differently activated units $D^1$ to $D^3$, is likewise conceivable.

Compound a' is commercially available, or can be prepared from commercially available synthons by methods known to those skilled in the art for acetylation or carbonylation. The conversion to b' can be effected, for example, by aldol reaction or Wittig reaction or other typical syntheses for generation of a double bond from a carbonyl function. For preparation of compound c', this step can be repeated as often as desired. The direct preparation of b' or c' from an unsubstituted (hetero-)aromatic, for example by Heck reaction, or reaction with unsaturated dialkylaminosubstituted carbonyls is also possible. The coupling of d' can be effected by metalation of compound c'. In this reaction, the carbonyl function can be intermediately protected. Compound e' can be prepared, for example, by Knoevenagel condensation with a compound bearing a methylene unit. By a typical cross-coupling reaction, for example Suzuki, Negishi or Stille coupling and the variants thereof, a component of the j type can be reacted with a component of the e' type to give the claimed compounds of the k type.

In the presence of a mirror plane at right angles to the longitudinal axis of the molecule, the synthesis can be correspondingly simplified owing to the symmetric molecular structure.

In principle, in all C—C coupling reactions, the reversal of the metal and halogen functionalities is conceivable, as is the use of different functional groups on either side, for example, but without limitation, sulfonates, triflates and carboxylic acids, or non-activated species called C—H-activated species. In general, but not exclusively, the C—C cross-coupling reactions are effected with use of a catalyst.

Among other compounds, corresponding bromide compounds and stannyl compounds have been synthesized from their precursor molecules and then converted to compounds of the invention. Three different routes are to be illustrated by way of example hereinafter.

Coupling by means of a
a. double inverse Stille coupling,
b. double Stille coupling or
c. single Stille coupling.

Also analogously suitable are further coupling reactions known from the literature, for example the Heck reaction or Kumada coupling. Suzuki, Negishi or Stille, Kumada or Hiyama and further coupling reactions are described, inter alia, in "Metal-Catalyzed Cross-Coupling Reactions, 2nd, Completely Revised and Enlarged Edition" (Wiley VCH, ISBN: 978-3-527-30518-6) (Suzuki: pages 41-123, Negishi: pages 619-670, Stille: pages 125-161, Kumada: pages 671-698, Hiyama: pages 163-216, further coupling reactions: pages 815-889).

Detailed hereinafter are the corresponding general procedures (GP1 to GP3) for versions a, b and c:

a) General Procedure (GP1)

1 mmol of dibromo compound (reactant 1) and 2.5 mmol of 2-[(E)-3-(5-trimethylstannanylfuran-2-yl)allylidene]malononitrile B4 (reactant 2) were dissolved in 4 mL of appropriate solvent (tab. 1) and the solution was degassed. Then 0.05 mmol of Pd catalyst was added and the reaction mixture was heated overnight. The reaction mixture was brought to room temperature, and solids that precipitated out were filtered off and washed with methanol. The crude product was recrystallized from appropriate solvent (tab. 1).

TABLE 1

| | | | Reaction conditions | | |
|---|---|---|---|---|---|
| No. | Reactant 1 | Reactant 2 | Reaction conditions | Yield (%) | Recrystallized from |
| 1 | A11 | B4 | Pd(PPh$_3$)$_4$/DMF (N,N-dimethylformamide)/80° C. | 75 | toluene |
| 2 | A21 | B4 | Pd$_2$dba$_3$/P(t-Bu)$_3$•HBF$_4$/toluene/110° C. | 55 | chlorobenzene |
| 3 | A20 | B4 | Pd(PPh$_3$)$_4$/chlorobenzene/136° C. | 38 | chlorobenzene |
| 4 | A9 | B4 | Pd(PPh$_3$)$_4$/dioxane/80° C. | 34 | chlorobenzene |
| 5 | A12 | B4 | Pd(PPh$_3$)$_4$/dioxane/80° C. | 71 | chlorobenzene |
| 8 | A6 | B4 | Pd(PPh$_3$)$_4$/dioxane/80° C. | 41 | chlorobenzene |

TABLE 1-continued

| | | | Reaction conditions | | |
|---|---|---|---|---|---|
| No. | Reactant 1 | Reactant 2 | Reaction conditions | Yield (%) | Recrystallized from |
| 10 | A7 | B4 | Pd(PPh$_3$)$_4$/dioxane/80° C. | 52 | chlorobenzene |
| 12 | A3 | B4 | Pd(PPh$_3$)$_4$/DMF/80° C. | 21 | toluene |
| 20 | A24 | B4 | Pd(PPh$_3$)$_4$/DMF/80° C. | 18 | chlorobenzene |
| 18 | A23 | B4 | Pd(PPh$_3$)$_4$/DMF/80° C. | 23 | toluene |
| 19 | A5 | B4 | Pd(PPh$_3$)$_4$/DMF/80° C. | 10 | toluene |
| 25 | A22 | B4 | Pd(PPh$_3$)$_4$/toluene/110° C. | 57 | chlorobenzene |
| 27 | A2 | B4 | Pd(PPh$_3$)$_4$/dioxane/80° C. | 27 | chlorobenzene |
| 28 | A10 | B4 | P(PPh$_3$)$_4$/dioxane/80° C. | 35 | chlorobenzene |
| 29 | A18 | B4 | Pd(PPh$_3$)$_4$/dioxane/80° C. | 66 | chlorobenzene |
| 31 | A26 | B4 | Pd-PEPPSI-IPent/CsF/dioxane/80° C. | 13 | chlorobenzene |
| 30 | A25 | B4 | Pd$_2$dba$_3$/P(t-Bu)$_3$/dioxane/80° C. | 64 | chlorobenzene |
| 33 | A28 | B4 | Pd2dba3/P(t-Bu)3/dioxane/80° C. | 52 | chlorobenzene |
| 35 | A30 | B4 | Pd2dba3/P(t-Bu)3/dioxane/80° C. | 49 | chlorobenzene |
| 36 | A31 | B4 | Pd2dba3/P(t-Bu)3/dioxane/80° C. | 16 | chlorobenzene |
| 38 | A35 | B4 | Pd2dba3/P(t-Bu)3/dioxane/80° C. | 48 | chlorobenzene |
| 39 | A34 | B4 | Pd2dba3/P(t-Bu)3/dioxane/80° C. | 68 | chlorobenzene |
| 40 | A36 | B4 | Pd2dba3/P(t-Bu)3/dioxane/80° C. | 14 | chlorobenzene |
| 41 | A37 | B4 | Pd2dba3/P(t-Bu)3/dioxane/80° C. | 61 | chlorobenzene |
| 42 | A33 | B4 | Pd2dba3/P(t-Bu)3/dioxane/80° C. | 47 | chlorobenzene |
| 47 | A39 | B4 | Pd(t-Bu)3/dioxane/80° C. | 70 | chlorobenzene | b) General Procedure (GP2)

1 mmol of distannyl compound (reactant 1) and 2.5 mmol of bromofuran-2-ylallylidenemalononitrile B2, or B6, or B10, or B12, or B14, or B16 (reactant 2) were dissolved in 4 mL of appropriate solvent (tab. 2), and the solution was degassed. Subsequently, 0.05 mmol of Pd catalyst was added and the reaction mixture was heated overnight. The reaction mixture was brought to room temperature, and solids that precipitated out were filtered off and washed with methanol. The crude product was recrystallized from appropriate solvent (tab. 2).

TABLE 2

| | | | Reaction conditions | | |
|---|---|---|---|---|---|
| No. | Reactant 1 | Reactant 2 | Reaction conditions | Yield (%) | Recrystallized from |
| 6 | A4 | B16 | Pd(PPh$_3$)$_4$/DMF/80° C. | 42 | chlorobenzene |
| 7 | A1 | B16 | Pd(PPh$_3$)$_4$/DMF/80° C. | 46 | chlorobenzene |
| 9 | A8 | B2 | Pd(PPh$_3$)$_4$/DMF/80° C. | 42 | chlorobenzene |
| 11 | A14 | B2 | Pd(PPh$_3$)$_4$/DMF/80° C. | 46 | chlorobenzene |
| 13 | A4 | B14 | Pd(PPh$_3$)$_4$/DMF/80° C. | 42 | chlorobenzene |
| 14 | A19 | B2 | Pd(PPh$_3$)$_4$/DMF/80° C. | 55 | chlorobenzene |
| 15 | A1 | B14 | Pd(PPh$_3$)$_4$/DMF/80° C. | 36 | chlorobenzene |
| 16 | A1 | B6 | Pd(PPh$_3$)$_4$/DMF/80° C. | 52 | chlorobenzene |
| 17 | A13 | B2 | Pd(PPh$_3$)$_4$/DMF/80° C. | 32 | chlorobenzene |
| 22 | A1 | B10 | Pd(PPh$_3$)$_4$/DMF/80° C. | 41 | chlorobenzene |
| 23 | A1 | B2 | Pd(PPh3)4/DMF/80° C. | 37 | chlorobenzene |
| 24 | A4 | B2 | Pd(PPh$_3$)$_4$/DMF/80° C. | 34 | chlorobenzene |
| 26 | A1 | B12 | Pd(PPh$_3$)$_4$/DMF/80° C. | 9 | chlorobenzene |
| 32 | A27 | B2 | Pd(PPh3)$_4$/1,4-dioxane/100° C. | 38 | toluene |
| 37 | A32 | B6 | Pd(PPh$_3$)$_4$/1,4-dioxane/80° C. | 14 | tetrahydrofuran | c) General Procedure (GP3)

In an argon-inertized Schlenk vessel, 1 mmol of halogen compound (reactant 1) and 1.2 mmol of 2-[3-(5-trimethylstannanyl-furan-2-yl)-allylidene]malononitrile B4 (reactant 2) were dissolved in 3 mL of solvent (tab. 3). The solution was degassed, then 0.05 mmol of Pd catalyst was added and the reaction mixture was heated while stirring overnight. The reaction mixture was cooled down to room temperature, and the resultant precipitate was filtered off and washed with methanol. The crude product was recrystallized from the respective solvent (tab. 3).

TABLE 3

| | | | Reaction conditions | | |
|---|---|---|---|---|---|
| No. | Reactant 3 | Reactant 2 | Reaction conditions | Yield (%) | Recrystallized from |
| 21 | C2 | B4 | Pd(PPh$_3$)$_4$, tetrahydrofuran, 65° C. | 24 | chlorobenzene |
| 34 | C8 | B4 | Pd(PPh$_3$)$_4$, 1,4-dioxane, 100° C. | 14 | chlorobenzene |
| 40 | C6 | B4 | Pd2dba3/P(t-Bu)3/ dioxane/80° C. | 72 | chlorobenzene |

Alternatively, compounds of the invention can also be effected via other known alkyl coupling reactions, for example Suzuki or Negishi reaction.

Synthesis of the Reactants

The reactants 1 (A), reactants 2 (B) and reactant 3 (C) are synthesized by the following methods:

Synthesis of the Reactants A

It is possible to prepare the corresponding stannyl compounds from the appropriately substituted or unsubstituted thiophenes, for example with tert-BuLi and trimethyltin chloride. For instance, tin(IV) halides, in the case of reaction with organometallic compounds, such as Grignard reagents, react to give the corresponding tin organyls. Organotin halides are usually obtained from tetraorganotin compounds by electrophilic substitution.

The bromides can be prepared by many reactions known from the literature (for example with potassium bromate and hydrogen bromide); analogously, reaction by a method proceeding from the corresponding trimethylsilyl compound with N-bromosuccinimide is also conceivable.

5,7-Bis(trimethylstannyl)-2,3-dihydrothieno[3,4-b][1,4]dioxin (A1)

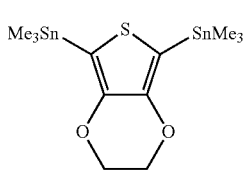

Compound A1 was synthesized in accordance with J. Mater. Chem. 1999, 2189.

4,6-Dibromo-1H,3H-thieno[3,4-c]furan (A2)

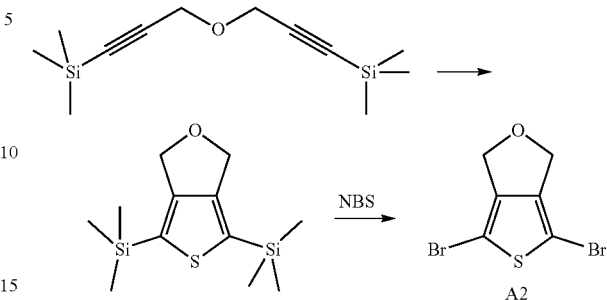

4,6-Bis(trimethylsilanyl)-1H,3H-thieno[3,4-c]furan 1.92 g (8.27 mmol) of bis(3-trimethylsilyl-2-propynyl) ether and 5.70 g (19.8 mmol) of titanium(IV) isopropoxide were dissolved in 110 mL of diethyl ether under an argon atmosphere at −70° C. 19.8 mL (39.7 mmol) of a 2M isopropylmagnesium chloride solution in diethyl ether were added dropwise. After stirring at −70° C. for 15 min, the mixture was warmed to −50° C. and stirred for a further 3.5 h. 2.12 g (66.2 mmol) of sulfur were added in portions and then the reaction mixture was warmed to RT (room temperature) within 16 h. A 1N HCl solution (90 mL) was added and the aqueous phase was extracted three times with hexane. The combined organic phases were washed with sat. Na$_2$CO$_3$ solution and sat. NaCl solution. They were dried over Na$_2$SO$_4$ and filtered, and the solvents were removed under reduced pressure. The crude product was purified by chromatography (SiO$_2$, R$_f$(DCM (dichloromethane))=0.88), and 1.87 g of product (84%) were obtained as a brown oil. $^1$H NMR (CDCl$_3$): 4.83 ppm (s, 4H), 0.28 (s, 18H).

4,6-Dibromo-1H,3H-thieno[3,4-c]furan (A2)

1.87 g (6.92 mmol) of 4,6-bis(trimethylsilanyl)-1H,3H-thieno[3,4-c]-furan were dissolved in 18 mL of DMF at 0° C. under an argon atmosphere. 2.77 g (15.2 mmol) of NBS (N-bromosuccinimide) dissolved 16 mL of DMF were added and the mixture was stirred at 0° C. for 1 h. It was warmed to RT and stirred for a further 16 h. 50 mL of water were added to the reaction mixture, which was extracted twice with MTBE (methyl tert-butyl ether). The combined organic phases were washed with 5% LiCl solution and sat. NaCl solution. They were dried over Na$_2$SO$_4$ and filtered, and the solvents were removed under reduced pressure. The residue was purified by chromatography (SiO$_2$, PE:DCM (2:1), R$_f$=0.54), and 703 mg of product A2 (36%) were obtained as a yellow oil. $^1$H NMR (CDCl$_3$): 4.75 ppm (s, 4H).

2,5-Dibromo-3-thiomethylthiophene (A3)

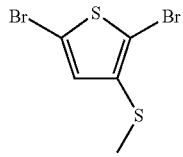

Compound A3 was prepared according to M. Lanzi et al. Reactive & Functional Polymers 2014 (83) 33-41.

2,5-Bis(trimethylstannyl)-3-methoxythiophene (A4)

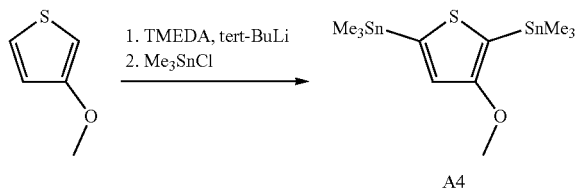

To a solution of 3-methoxythiophene (342 mg, 3.00 mmol) and N,N,N',N'-tetramethylethylenediamine (1.05 g, 9.00 mmol) in hexane (50 mL) was added dropwise, at −78° C. under an argon atmosphere, tert-butyllithium solution (1.48 M in hexane, 6.10 mL, 9.00 mmol). The reaction mixture was stirred at −65° C. for 10 min, warmed to room temperature and stirred for a further 4.5 h. Subsequently, the reaction solution was cooled down to −65° C., trimethyltin chloride solution (1M in tetrahydrofuran, 9 mL, 9.00 mmol) was added, and the mixture was warmed to room temperature in a cooling bath overnight, poured onto water (40 mL) and extracted with hexane (3×30 mL). The combined organic phases were washed with saturated ammonium chloride solution (2×30 mL), hydrochloric acid (1M, 4×30 mL) and water (30 mL), dried over sodium sulfate and filtered. The removal of the solvent under reduced pressure gave crude 3-methoxy-2,5-bis-(trimethylstannanyl)thiophene (1.18 g, 2.58 mmol, 86%) as a colorless viscous oil, which was used in the next reaction step without further purification. $^1$H NMR (CDCl$_3$): 7.04 ppm (s, 1H), 3.83 (s, 3H), 0.35 (s, 9H), 0.33 (s, 9H).

2,5-Dibromo-3-(3,3,3-trifluoropropoxy)thiophene (A5)

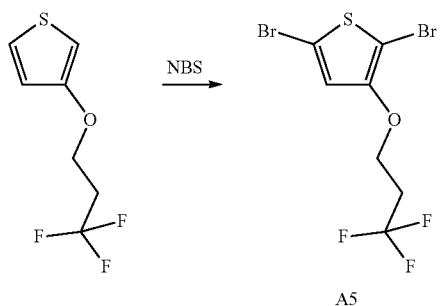

432 mg (2.20 mmol) of 3-(3,3,3-trifluoropropoxy)thiophene (synthesis analogous to A18a) were dissolved in 5 mL of dry DMF at 0° C. under argon. 1.03 g (5.72 mmol) of NBS were added in small portions and the mixture was stirred at 0° C. for 1 h. Once the cooling bath had been removed, the reaction mixture was stirred at room temperature for 24 h. The reaction mixture was admixed with water and extracted twice with 20 mL of MTBE. The organic phase was dried over sodium sulfate. The solvents were removed on a rotary evaporator and the residue was chromatographed using silica gel in ethyl acetate/petroleum ether 1/9. This gave 319 mg of A5. EI-MS, m/z 353.89 [M]. $^1$H NMR (CDCl$_3$) ppm: 6.77 (s, 1H), 4.22 (t, 2H), 2.61 (m, 2H).

2,5-Dibromo-3,4-dimethylthiophene (A6)

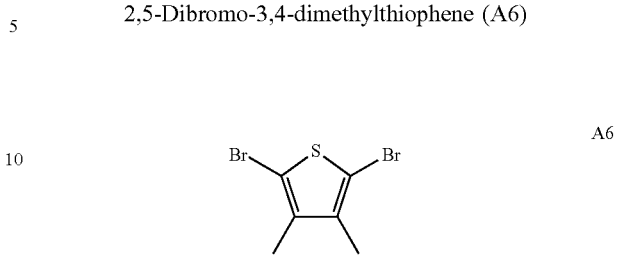

Compound A6 was prepared according to Yasuyuki Kiya, Jay C. Henderson, Geoffrey R. Hutchison, Héctor D. Abruña J. Mater. Chem. 2007, 17, 4366-4376.

2,5-Dibromo-3-methylthiophene (A7)

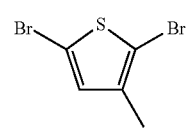

A7 is commercially available.

3-Ethyl-2,5-bis(trimethylstannyl)thiophene (A8)

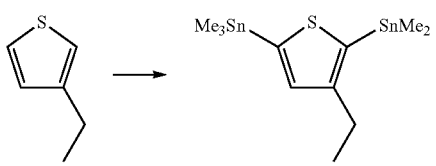

To a solution of 224 mg (2.00 mmol) of 3-ethylthiophene in 10 mL of dry n-hexane and 0.85 mL of TMEDA (N,N,N,N-tetramethylethylene-diamine) were added dropwise 5.0 mL (8.00 mmol) of 1.6 M n-butyllithium in n-hexane at −78° C. After stirring at −78° C. for 10 min., the cooling bath was removed and the reaction mixture was stirred at R.T. for 20 h. The suspension was cooled down again to −78° C. and 8.0 mL (8.00 mmol) of a 1.0M trimethylstannyl chloride solution in THF (tetrahydrofuran) were added dropwise. The reaction mixture was stirred at −78° C. for 1 h and then at R.T. for 3 h. After addition of 50 mL of n-hexane, hydrolysis was effected with water. The organic phase was washed three times with 50 mL of water and dried over sodium sulfate. After the solvents had been removed, the residue was dried under reduced pressure. The crude product (869 mg, 99%) was used in the next stage without further purification steps. $^1$H NMR (CDCl$_3$): 7.21 ppm (s, 1H), 2.71 (q, 2H), 1.24 (t, 3H), 0.37 (s, 9H), 0.35 (s, 9H).

1,3-Dibromo-4,5,6,7-tetrahydrobenzo[c]thiophene (A9)

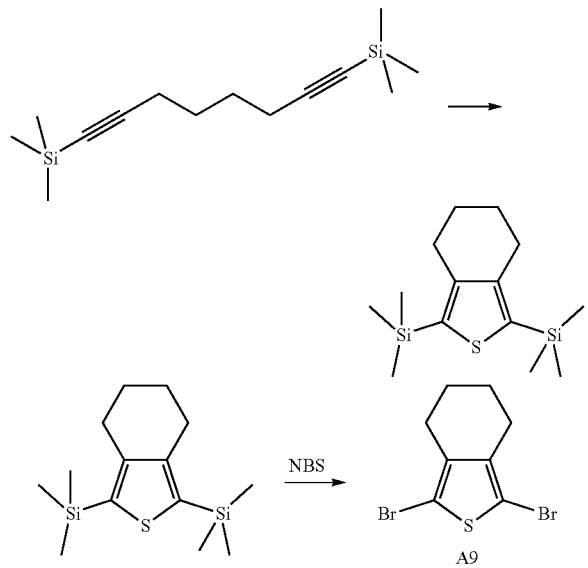

1,3-Bis(trimethylsilanyl)-4,5,6,7-tetrahydrobenzo[c]thiophene 7.13 g (28.5 mmol) of 1,8-bis(trimethylsilanyl)octa-1,7-diyne and 19.6 g (68.4 mmol) of titanium(IV) isopropoxide were dissolved in 380 mL of diethyl ether under an argon atmosphere at −70° C. 68.4 mL (137 mmol) of a 2M isopropylmagnesium chloride solution in diethyl ether were added dropwise. After stirring at −70° C. for 15 min, the mixture was warmed to −50° C. and stirred for a further 3.5 h. 7.31 g (228 mmol) of sulfur were added in portions and then the reaction mixture was warmed to RT within 16 h. A 1N HCl solution (300 mL) was added and the aqueous phase was extracted three times with hexane. The combined organic phases were washed with sat. $Na_2CO_3$ solution and sat. NaCl solution. They were dried over $Na_2SO_4$ and filtered, and the solvents were removed under reduced pressure. The residue was purified by chromatography ($SiO_2$, PE, $R_f$=0.74), and 5.20 g (18.4 mmol) of product (65%) were obtained as a pale yellow oil. $^1$H NMR ($CDCl_3$): 2.80 ppm (m, 4H), 1.76 (m, 4H), 0.31 (s, 18H).

1,3-Dibromo-4,5,6,7-tetrahydrobenzo[c]thiophene (A9)

4.35 g (15.4 mmol) of 1,3-bis(trimethylsilanyl)-4,5,6,7-tetrahydro-benzo[c]thiophene were dissolved in 40 mL of DMF at 0° C. under an argon atmosphere. 6.09 g (33.9 mmol) of NBS dissolved 37 mL of DMF were added and the mixture was stirred at 0° C. for 1 h. The mixture was warmed to RT and stirred for a further 16 h. 200 mL of water were added to the reaction mixture, which was extracted twice with MTBE. The combined organic phases were washed with 2N NaOH solution, 5% LiCl solution and sat. NaCl solution. They were dried over $Na_2SO_4$ and filtered, and the solvents were removed under reduced pressure. The residue was purified by chromatography ($SiO_2$, PE, $R_f$=0.73), and 4.31 g of product A9 (79%) were obtained as a pale yellow oil. $^1$H NMR ($CDCl_3$): 2.50 ppm (m, 4H), 1.72 (m, 4H).

1,3-Dibromo-5,6-dihydro-4H-cyclopenta[c]thiophene (A10)

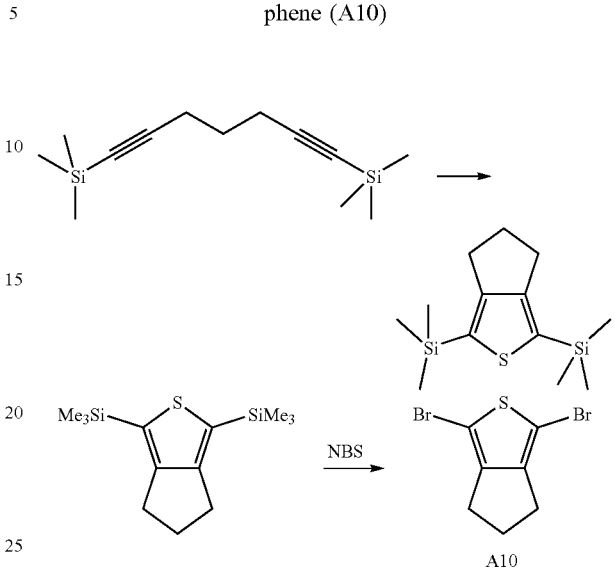

1,3-Bis(trimethylsilanyl)-5,6-dihydro-4H-cyclopenta[c]thiophene (A10a)

2.37 g (10.0 mmol) of 1,7-bis(trimethylsilanyl)hepta-1,6-diyne and 6.91 g (24.0 mmol) of titanium(IV) isopropoxide were dissolved in 130 mL of diethyl ether under an argon atmosphere at −70° C. 24.0 mL (48.0 mmol) of a 2M isopropylmagnesium chloride solution in diethyl ether were added dropwise. After stirring at −70° C. for 15 min, the mixture was warmed to −50° C. and stirred for a further 3.5 h. 2.57 g (80.0 mmol) of sulfur were added in portions and then the reaction mixture was warmed to RT within 16 h. A 1N HCl solution (105 mL) was added and the aqueous phase was extracted three times with hexane. The combined organic phases were washed with sat. $Na_2CO_3$ solution and sat. NaCl solution. They were dried over $Na_2SO_4$ and filtered, and the solvents were removed under reduced pressure. The crude product was purified by chromatography ($SiO_2$, $R_f$(PE)=0.63), and 2.38 g of product (89%) were obtained as a pale yellow oil. $^1$H NMR ($CDCl_3$): 2.69 ppm (t, 4H), 2.43 (m, 2H), 0.30 (s, 18H).

1,3-Dibromo-5,6-dihydro-4H-cyclopenta[c]thiophene (A10)

2.38 g (8.88 mmol) of 1,3-bis(trimethylsilanyl)-5,6-dihydro-4H-cyclopenta[c]thiophene were dissolved in 22 mL of DMF at 0° C. under an argon atmosphere. 3.19 g (17.8 mmol) of NBS dissolved 20 mL of DMF were added and the mixture was stirred at 0° C. for 1 h. It was warmed to RT and stirred for a further 16 h. 50 mL of water were added to the reaction mixture, which was extracted twice with MTBE. The combined organic phases were washed with 5% LiCl solution and sat. NaCl solution. They were dried over $Na_2SO_4$ and filtered, and the solvents were removed under reduced pressure. The residue was purified by chromatography ($SiO_2$, PE, $R_f$=0.54), and 1.25 g of product A10 (50%) were obtained as a colorless oil. $^1$H NMR ($CDCl_3$): 2.62 ppm (t, 4H), 2.37 (m, 2H).

2,5-Dibromo-3,4-bis(3,3,3-trifluoropropoxy)thiophene (A11)

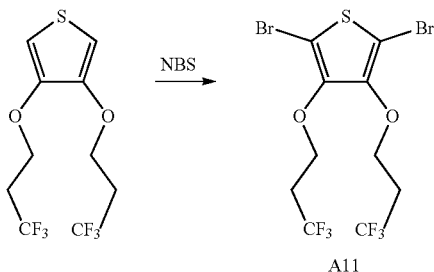

2.75 g (8.9 mmol) of 3,4-bis(3,3,3-trifluoropropoxy)thiophene (synthesis analogous to A18a) were dissolved in 33 mL of dry DMF and cooled down to 0° C. 3.21 g (17.8 mmol) of NBS were added in small portions and the reaction mixture was stirred at room temperature overnight. Subsequently, the reaction mixture was added to 100 mL of ice-water. The aqueous phase was extracted three times with 100 mL of DCM. The organic phase was washed three times with 100 mL of sat. NaCl and dried over sodium sulfate. The solvents were removed on a rotary evaporator and the residue was purified via chromatography (SiO$_2$, DCM/petroleum ether 1/9). This gave 2.20 g of A11. EI-MS, m/z 465.82 [M].

2,5-Dibromothiophene (A12)

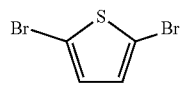

A12 is commercially available.

3,4-Dimethoxy-2,5-bis(trimethylstannanyl)thiophene (A13)

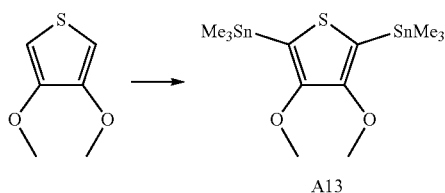

To a solution of 288 mg (2.00 mmol) of 3,4-dimethoxythiophene in 10 mL of dry n-hexane and 0.85 mL of TMEDA were added dropwise, at −78° C., 4.05 mL (6.08 mmol) of a 1.5 M tert-butyllithium solution in n-pentane. The mixture was stirred at −78° C. for 10 min and at R.T. for a further 3.5 h. The resultant suspension was cooled down again to −78° C., and 6.0 mL (6.00 mmol) of a 1.0 M trimethylstannyl chloride solution in THF were added dropwise. The reaction mixture was stirred at −78° C. for 1 h and at R.T. for a further 16 h. Subsequently, 50 mL of n-hexane were added and hydrolysis was effected with water. The organic phase was removed, washed three times with 50 mL of water and dried over sodium sulfate. After the removal of the solvents, the residue was dried under reduced pressure (681 mg, 72%). $^1$H NMR (acetone-d6): 3.77 ppm (s, 6H), 0.34 (s, 18H).

3,4-Diethyl-2,5-bis(trimethylstannyl)thiophene (A14)

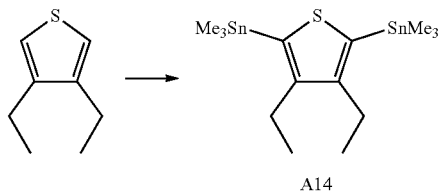

To a solution of 280 mg (2.00 mmol) of 3,4-diethylthiophene in 10 mL of dry n-hexane and 0.85 mL of TMEDA were added dropwise, at −78° C., 2.4 mL (6.00 mmol) of a 2.5 M n-butyllithium solution in n-hexane. The mixture was stirred at −78° C. for 10 min and at R.T. for a further 20 h. The resultant suspension was cooled down again to −78° C., and 6.0 mL (6.00 mmol) of a 1.0 M trimethylstannyl chloride solution in THF were added dropwise. The reaction mixture was stirred at −78° C. for 1 h and at R.T. for a further 3 h. Subsequently, 50 mL of n-hexane were added and hydrolysis was effected with water. The organic phase was removed, washed three times with 50 mL of water and dried over sodium sulfate. After the removal of the solvents, the residue was dried under reduced pressure (887 mg, 95%). $^1$H NMR (CDCl$_3$): 2.66 ppm (q, 4H), 1.17 (t, 6H), 0.36 (s, 18H).

6,8-Dibromo-3,3-difluoro-3,4-dihydro-2H-thieno[3,4-b][1,4]dioxepine (A18)

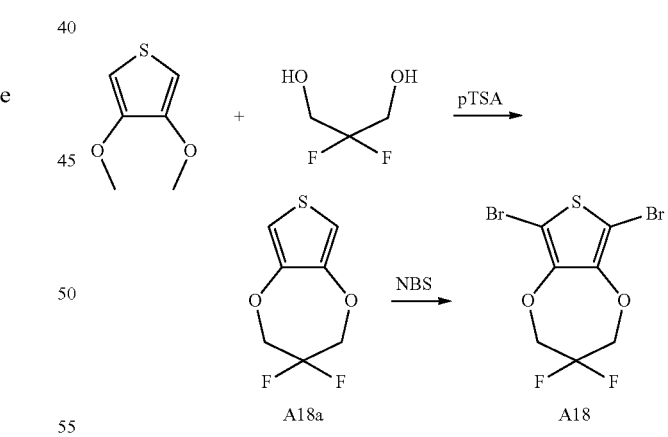

3,3-Difluoro-3,4-dihydro-2H-thieno[3,4-b][1,4]dioxepine (A18a)

In a Soxhlet apparatus, the extraction thimble was charged with molecular sieve (4 Å) and, under an argon atmosphere, 105 mg (0.55 mmol) of p-toluenesulfonic acid monohydrate in 52 mL toluene were heated under reflux for 1 h. The mixture was allowed to cool down to RT, and 787 mg (5.46 mmol) of 3,4-dimethoxythiophene and 1.28 g (10.9 mmol) of 2,2-difluoropropane-1,3-diol were added, and the mixture was heated under reflux for 16 h. Water (50 mL) was added to the reaction mixture, and the aqueous phase was extracted once with toluene. The combined organic phases were washed with sat. NaCl solution. They were dried over $Na_2SO_4$ and filtered, and the solvents were removed under reduced pressure. The crude product was purified by chromatography using silica gel, and 237 mg of product (23%) were obtained as a colorless oil. $^1$H NMR ($CDCl_3$): 6.58 ppm (s, 2H), 4.30 (t, 4H).

6,8-Dibromo-3,3-difluoro-3,4-dihydro-2H-thieno[3,4-b][1,4]dioxepine (A18)

236 mg (1.23 mmol) of 3,3-difluoro-3,4-dihydro-2H-thieno[3,4-b][1,4]-dioxepine were dissolved in 15 mL of DMF at 0° C. under an argon atmosphere. 442 mg (2.46 mmol) of NBS were added at 0° C. The mixture was warmed to RT and stirred for a further 16 h. 30 mL of 5% LiCl solution were added to the reaction mixture, which was extracted three times with DCM. The combined organic phases were washed with 5% LiCl solution and sat. NaCl solution. They were dried over $Na_2SO_4$ and filtered, and the solvents were removed under reduced pressure. The residue was purified by chromatography using silica gel, and 300 mg of product A18 (70%) were obtained as a colorless oil. $^1$H NMR ($CDCl_3$): 4.38 ppm (t, 4H).

6,8-Bis(trimethylstannyl)-3,4-dihydro-2H-thieno[3,4-b][1,4]dioxepine (A19)

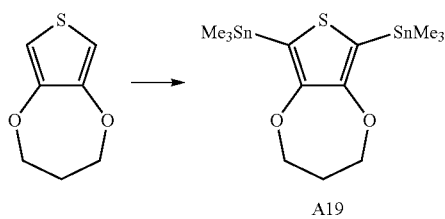

A19

To a solution of 312 mg (2.00 mmol) of 3,4-dihydro-2H-thieno[3,4-b]-[1,4]dioxepine in 10 mL of n-hexane and 0.85 mL of TMEDA were added dropwise 5.33 mL (8.00 mmol) of 1.5 M tert-butyllithium solution in n-pentane at −78° C. The mixture was stirred at −78° C. for 10 min and then at RT for 3.5 h. The suspension was cooled to −78° C. and 8.0 mL (8.00 mmol) of 1.0M trimethylstannyl chloride solution in THF were added. The reaction mixture was brought to RT overnight, diluted with 20 mL of n-hexane and washed with 1N HCl solution and water. The organic phase was dried over $Na_2SO_4$ and filtered, and the solvents were distilled off under reduced pressure. The residue A19 (548 mg, 57%) was used in the next stage without further purification. $^1$H NMR ($CDCl_3$): 3.99 ppm (m, 4H), 2.15 (m, 2H), 0.32 (s, 18H).

1,4-Dibromo-2,5-dimethoxybenzene (A20)

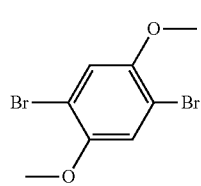

A20 is commercially available.

1,3-Dibromo-4,9-dioxa-2-thiacyclopenta[b]naphthalene (A21)

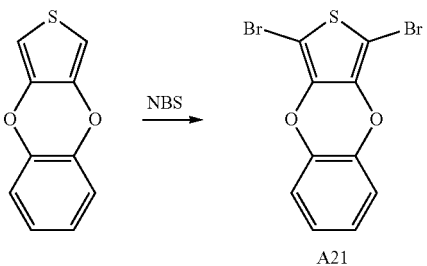

368 mg (1.93 mmol) of 4,9-dioxa-2-thiacyclopenta[b]naphthalene (Roquet, J. Mater. Chem. 2004, 14, 1396-1400) were dissolved in 10 mL of DMF at 0° C. under an argon atmosphere. 696 mg (3.87 mmol) of NBS were added and the mixture was stirred at 0° C. for 1 h. The mixture was warmed to RT and stirred for a further 16 h. 30 mL of water were added to the reaction mixture, which was extracted three times with DCM. The combined organic phases were washed with sat. $Na_2S_2O_3$ solution and sat. NaCl solution. They were dried over $Na_2SO_4$ and filtered, and the solvents were removed under reduced pressure. The residue was recrystallized from methanol, and 523 mg of product A21 (78%) were obtained as a colorless solid. $^1$H NMR ($CDCl_3$): 6.98-7.05 ppm (m, 4H).

1,3-Dibromo-5,6-dihydro-4-oxa-2,7-dithiaindene (A22)

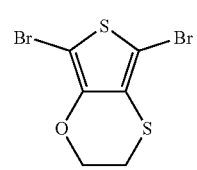

Compound A22 was synthesized in accordance with compound A24.

5,7-Dibromo-2-trifluoromethyl-2,3-dihydrothieno[3,4-b][1,4]dioxin (A23)

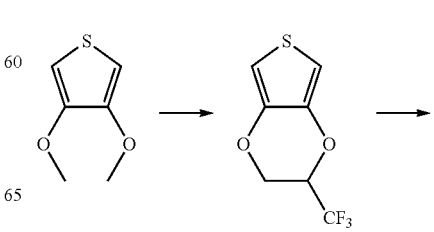

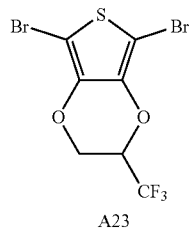

A23

2-Trifluoromethyl-2,3-dihydrothieno[3,4-b][1,4]dioxin

In a Soxhlet apparatus, the extraction thimble was charged with molecular sieve (4 Å) and, under an argon atmosphere, 74 mg (0.39 mmol) of p-toluenesulfonic acid monohydrate in 36 mL of toluene were heated under reflux for 1 h. The mixture was allowed to cool down to RT, and 555 mg (3.85 mmol) of 3,4-dimethoxythiophene and 1.00 g (7.70 mmol) of 3,3,3-trifluoropropane-1,2-diol were added and the mixture was heated under reflux for 16 h. Water (50 mL) was added to the reaction mixture and the aqueous phase was extracted once with toluene. The combined organic phases were washed with sat. NaCl solution. They were dried over Na$_2$SO$_4$ and filtered, and the solvents were removed under reduced pressure. The crude product was purified by chromatography using silica gel, and 322 mg of product (40%) were obtained as a colorless solid. GC-MS (EI, 75 eV) m/z 209.9 (M$^+$, 100%).

5,7-Dibromo-2-trifluoromethyl-2,3-dihydrothieno[3,4-b][1,4]dioxin (A23)

322 mg (1.53 mmol) of 2-trifluoromethyl-2,3-dihydrothieno[3,4-b]-[1,4]dioxin were dissolved in 15 mL of THF at −10° C. under an argon atmosphere. 597 mg (3.32 mmol) of NBS were added and the mixture was stirred at −7° C. for 1 h. It was warmed to RT and stirred for a further 4 h. 50 mL of water were added to the reaction mixture, which was extracted three times with MTBE. The combined organic phases were washed with 2M NaOH solution and sat. NaCl solution. They were dried over Na$_2$SO$_4$ and filtered, and the solvents were removed under reduced pressure. The residue was purified by chromatography using silica gel, and 375 mg of product A23 (67%) were obtained as a pale yellow solid. $^1$H NMR (acetone-d6): 5.15-5.21 ppm (m, 1H), 4.57-4.61 (m, 2H).

5,7-Dibromo-2,3-dihydrothieno[3,4-b][1,4]dithiin (A24)

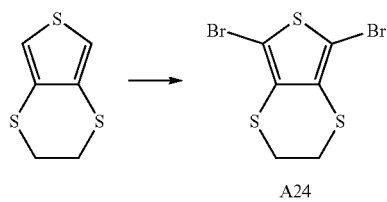

A24

1.12 g (6.41 mmol) 2,3-dihydro-thieno[3,4-b][1,4]dithiin (Wijsboom, Angew. Chem. Int. Ed. 2009 (48), 30, 5443-5447) were dissolved in 16 mL of DMF at 0° C. under an argon atmosphere. 2.36 g (13.1 mmol) of NBS were dissolved in 15 mL of DMF and added dropwise at 0° C. The mixture was warmed to RT and stirred for a further 4 h. 100 mL of 5% LiCl solution were added to the reaction mixture, which was extracted four times with MTBE. The combined organic phases were washed with 5% LiCl solution and sat. NaCl solution. They were dried over Na$_2$SO$_4$ and filtered, and the solvents were removed under reduced pressure. The residue was purified by chromatography using silica gel, and 1.80 g of product A24 (85%) were obtained as a colorless oil. GC-MS (EI, 75 eV) m/z 331.8 (M$^+$, 100%).

2,7-Dibromo-9-propyl-9H-carbazole (A25)

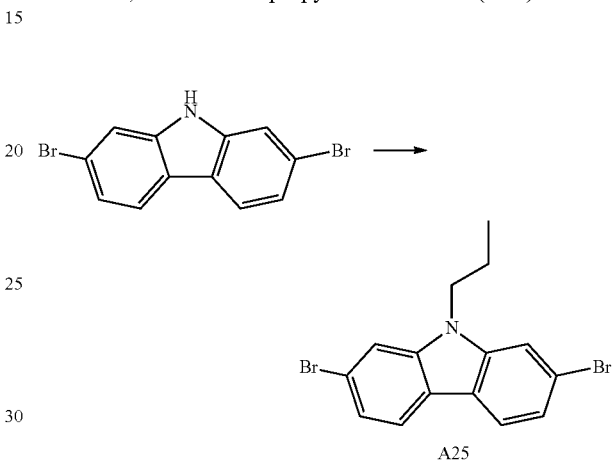

A25

To a solution of potassium hydroxide (812 mg, 12.3 mmol) in dry dimethyl sulfoxide (25 mL) was added 2,7-dibromo-9H-carbazole (2.5 g, 7.69 mmol), and the mixture was stirred at room temperature for 15 min. Propyl bromide (1.43 g, 11.5 mmol) was added to the reaction mixture, which was stirred at room temperature for 16 h, then poured onto water (200 mL) and extracted with diethyl ether (3×100 mL). The combined organic phases were dried over sodium sulfate and filtered, and the solvent was removed under reduced pressure. Purification by column chromatography (silica gel, petroleum ether) gave 2,7-dibromo-9-propyl-9H-carbazole (2.80 g, 7.63 mmol, 99%) as a colorless crystalline solid. $^1$H NMR (CDCl$_3$): 7.89 ppm (2, 2H), 7.54 (d, 2H), 7.34 (dd, 2H), 4.17 (t, 2H), 1.89 (sext, 2H), 0.99 (t, 3H).

4,8-Dibromobenzo[1,2b;4,5-b']difuran (A26)

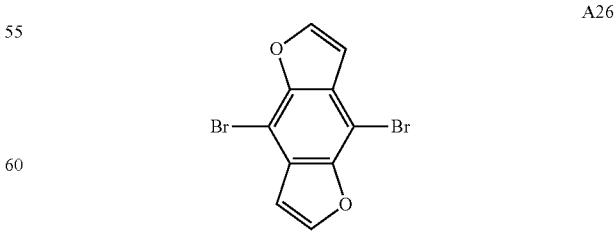

A26

A26 was synthesized in accordance with the method known from literature (Bian, J. Material. Chem. A 2015, 3, 1920).

3-Ethyl-5,5'-bis(trimethylstannanyl)[2,2']bithiophenyl (A27)

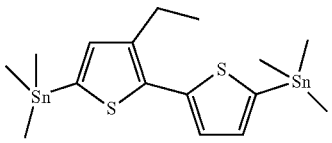

The compound was prepared in accordance with A19. ¹H NMR (CDCl₃): 7.14 (d, 1H), 7.06 (d, 1H), 6.95 (s, 1H), 2.74 (q, 2H), 1.19 (t, 3H), 0.37 (m, 18H).

2,7-Dibromo-9,9-dimethyl-9H-fluorene (A28)

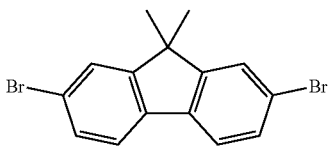 [SMILES: CC1(C)c2cc(Br)ccc2-c2ccc(Br)cc21]

Compound A28 is commercially available.

2-Bromo-3-methoxythiophene (A29)

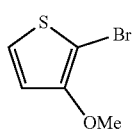

A29

The synthesis of A29 was in accordance with the literature method of Canesi, Eleonora V. et al., Journal of the American Chemical Society, 134(46), 19070-19083; 2012

2,7-Dibromo-9-methyl-9H-carbazole (A30)

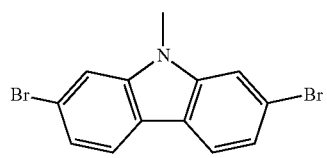 [SMILES: Cn1c2cc(Br)ccc2c2ccc(Br)cc21]

To an initially charged solution of potassium hydroxide (317 mg, 4.80 mmol) in dry dimethyl sulfoxide (12 mL) was added 2,7-dibromo-9H-carbazole (975 mg, 3.00 mmol), and the mixture was stirred at room temperature for 15 min. Subsequently, methyl iodide (426 mg, 0.456 mL, 3.00 mmol) was added dropwise and the mixture was stirred at room temperature for a further 16 h. The reaction mixture was poured onto water (100 mL) and extracted with diethyl ether (3×50 mL). The combined organic phases were dried over sodium sulfate and filtered off, and the solvent was removed under reduced pressure. Column chromatography (silica gel, petroleum ether) gave 2,7-dibromo-9-methyl-9H-carbazole (902 mg, 2.66 mmol, 89%) as a colorless crystalline solid. ¹H NMR (CDCl₃): 7.89 ppm (dd, 2H), 7.55 (d, 2H), 7.35 (dd, 2H), 3.79 (s, 3H).

2,7-Dibromo-9-ethyl-9H-carbazole (A31)

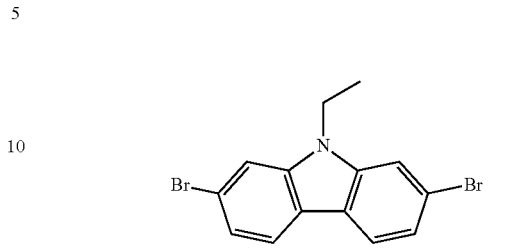

To an initially charged solution of potassium hydroxide (330 mg, 4.93 mmol) in dry dimethyl sulfoxide (11 mL) was added 2,7-dibromo-9H-carbazole (1.00 g, 3.08 mmol), and the mixture was stirred at room temperature for 15 min. Subsequently, ethyl bromide (503 mg, 0.345 mL, 4.62 mmol) was added dropwise and the mixture was stirred at room temperature for a further 16 h. The reaction mixture was poured onto water (80 mL) and extracted with diethyl ether (2×100 mL). The combined organic phases were dried over sodium sulfate and filtered off, and the solvent was removed under reduced pressure. Column chromatography (silica gel, petroleum ether) gave 2,7-dibromo-9-ethyl-9H-carbazole (890 mg, 2.52 mmol, 82%) as a colorless crystalline solid. ¹H NMR (CDCl₃): 7.90 ppm (d, 2H), 7.55 (d, 2H), 7.35 (dd, 2H), 4.28 (q, 2H), 1.43 (t, 3H). GC-MS (EI) m/z 352.81 (M⁺, 100%).

9-Propyl-2,7-bis(trimethylstannanyl)-9H-carbazole (A32)

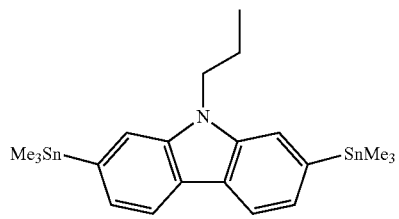

To an initial charge of 2,7-dibromo-9-propyl-9H-carbazole (1.00 g, 2.72 mmol) under argon in dry tetrahydrofuran (50 mL) at −78° C. was added dropwise, within 15 min, tert-butyllithium (1.5 M in pentane, 3.63 mL), and the mixture was stirred at −78° C. for a further 1.5 h. Thereafter, trimethylstannyl chloride (1 M in tetrahydrofuran, 5.72 mL) was added to the reaction mixture, which was warmed to room temperature in the cooling bath while stirring overnight. Subsequently, the reaction mixture was poured onto water (200 mL) and extracted with diethyl ether (3×100 mL). The combined organic phases were washed with saturated NaCl solution (3×100 mL), dried over sodium sulfate and filtered off, and the solvent was removed under reduced pressure. Recrystallization from methanol/ethanol (2:1) gave 9-propyl-2,7-bis(trimethylstannanyl)-9H-carbazole (780 mg, 1.46 mmol, 54%) as a colorless crystalline solid. ¹H NMR (acetone-D₆): 8.11 ppm (dd, 2H), 7.72-7.73 (m, 2H), 7.32 (dd, 2H), 4.44 (t, 2H), 1.87-1.97 (m, 2H), 0.94 (t, 3H), 0.35 (s, 18H).

3,6-Dibromo-9-propyl-9H-carbazole (A33)

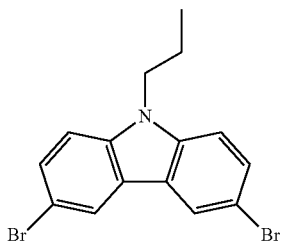 [SMILES: CCCn1c2ccc(Br)cc2c2cc(Br)ccc21]

To an initially charged solution of potassium hydroxide (315 mg, 4.77 mmol) in dry dimethyl sulfoxide (11 mL) was added 3,6-dibromo-9H-carbazole (1.00 g, 2.98 mmol), and the mixture was stirred at room temperature for 15 min. Subsequently, ethyl bromide (503 mg, 0.345 mL, 4.62 mmol) was added dropwise and the mixture was stirred at room temperature for a further 16 h. The reaction mixture was poured onto water (80 mL) and extracted with diethyl ether (2×100 mL). The combined organic phases were dried over sodium sulfate and filtered off, and the solvent was removed under reduced pressure. Column chromatography (silica gel, petroleum ether) gave 2,7-dibromo-9-ethyl-9H-carbazole (790 mg, 2.15 mmol, 72%) as a colorless crystalline solid. $^1$H NMR (acetone-D$_6$): 8.37-8.39 ppm (m, 2H), 7.58-7.60 (m, 4H), 4.41 (t, 2H), 1.90 (m, 2H), 0.93 (t, 3H). GC-MS (EI) m/z 367.00 (M$^+$, 83%).

2,7-Dibromo-9-isobutyl-9H-carbazole (A34)

The synthesis of A34 is analogous to the synthesis of A31.

1,5-Dibromo-2,4-dimethoxybenzene (A35)

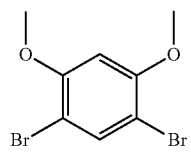

Compound A35 is commercially available.

4,7-Dibromobenzo[1,2,5]triazole (A37)

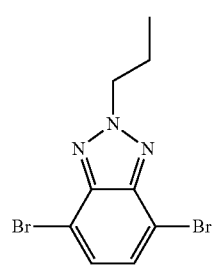

Compound A37 is commercially available.

5,6-Dihydro-4H-cyclopenta[c]thiophene (A38a)

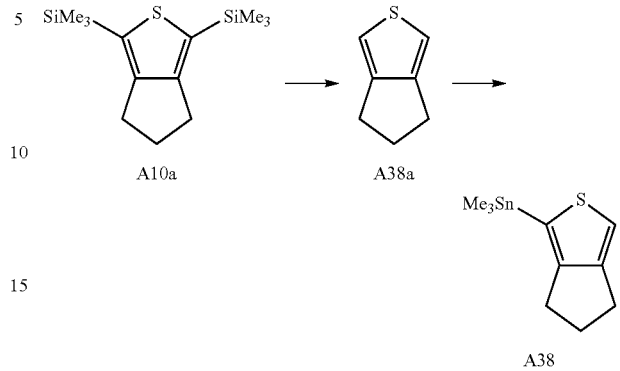

8.00 g (29.8 mmol) of 1,3-bis(trimethylsilanyl)-5,6-dihydro-4H-cyclopenta[c]thiophene (A10a) were dissolved in 150 mL of THF under an argon atmosphere. 89.4 mL (89.4 mmol, 1.0 M in THF) of tetrabutylammonium fluoride solution were added and the mixture was stirred for 3 h. 50 mL of sat. Na$_2$CO$_3$ solution were added to the reaction mixture, which was extracted three times with n-hexane. The combined organic phases were washed with sat. Na$_2$CO$_3$ solution, water and sat. NaCl solution. They were dried over Na$_2$SO$_4$ and filtered, and the solvents were removed under reduced pressure. The residue was purified by fractional distillation (7 mbar, 50° C.-55° C.), and 2.89 g of 5,6-dihydro-4H-cyclopenta[c]thiophene product (78%) were obtained as a colorless oil. 1H NMR (CDCl3): 6.76 ppm (s, 2H), 2.67 (t, 4H), 2.37 (m, 2H).

2-Trimethylstannyl-5,6-dihydro-4H-cyclopenta[c]thiophene (A38)

2.66 g (21.4 mmol) of 5,6-dihydro-4H-cyclopenta[c]thiophene were dissolved in 75 mL of THF and cooled to −78° C. 9.0 mL (22.5 mmol) of 2.5 M n-butyllithium solution in hexane were added dropwise and stirred at −78° C. for 2 h. 22.5 mL (22.5 mmol) of a 1.0 M trimethylstannyl chloride solution in THF were added and the mixture was warmed to room temperature overnight. Hydrolysis was effected with 15 mL of water, and the aqueous phase was extracted three times with n-hexane. The combined org. phases were washed with sat. NaCl solution and dried over Na$_2$SO$_4$. After filtration, the solvents were distilled off under reduced pressure and the residue was used in the next stage without further purification. This gave 5.40 g of product A38 (88%) as a yellow oil. 1H NMR (CDCl3): 7.04 ppm (m, 2H), 2.63-2.72 (m, 4H), 2.36-2.43 (m, 2H), 0.34 (s, 9H).

4,7-Dibromo-1H-indole (A39)

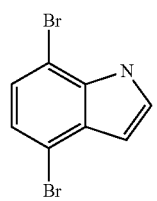 [SMILES: Brc1ccc(Br)c2[nH]ccc12]

The synthesis of A39 is by the literature method: Dobbs, Adrian P.; Voyle, Martyn; Whittall, Neil, Synlett, 1999, 10, 1594-1596.

Synthesis of the Reactants 2 (B)

Terminal acceptor groups can be synthesized, for example, by known methods, for example Gattermann, Gattermann-Koch, Houben-Hoesch, Vilsmeier/Vilsmeier-Haack, Friedel-Crafts acylation or after lithiation, by a reaction with an acid derivative or carbonylating reagent.

Further acceptor groups are achievable by trans-functionalization of the above-described carbonyl function C(O)R, for example by Knoevenagel condensation, as shown for reactant B4.

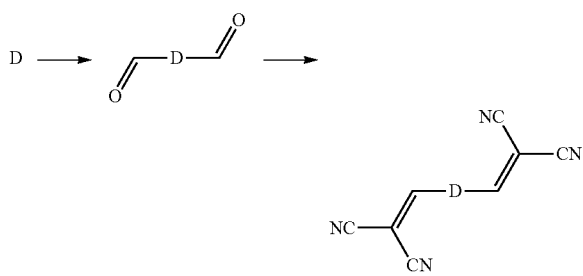

Acceptor end groups can be introduced, for example, with BuLi and tetracyanoethylene (Cai et al, J. Phys. Chem. B 2006, 110, 14590).

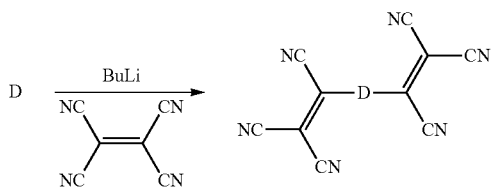

Alternatively, the reaction can also be conducted without BuLi in DMF (Pappenfus et. al, Org. Lett. 2008, 10, 8, 1553).
B1, B5, B9, B11

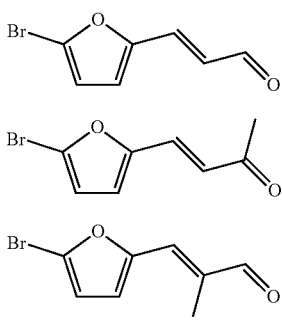

The synthesis of B1, B5, B9 and B11 is in accordance with the literature of I. I. Popov, Z. N. Nazarova, A. P. Chumak, Chem. Heterocycl. Compd., 1978, 14, (3), 253-255.

50 mmol of 5-bromo-2-furfural (reactant 1) were suspended in 100 mL of 6% NaOH solution. Carbonyl compound (reactant 2) in 15 mL of water was added dropwise to the reaction mixture at 0° C. Stirring was continued at 0° C. for 1 h. The precipitate was filtered off, washed with water and dried. The crude product was purified by chromatography using silica gel.

TABLE 4

| | Synthesis | | |
|---|---|---|---|
| Name | Reactant 2 | Yield, % | $^1$H NMR |
| B1 | acetaldehyde | 74 | acetone-d6: 9.64 ppm (d, 1H), 7.44 (d, 1H), 7.04 (d, 1H), 6.73 (d, 1H), 6.47 (dd, 1H). |
| B5 | acetone | 55 | CDCl$_3$: 7.17 ppm (d, 1H), 6.63 (d, 1H), 6.61 (d, 1H), 6.43 (d, 1H), 2.32 (s, 3H). |
| B9 | propionaldehyde | 98 | acetone-d6: 9.52 ppm (s, 1H), 7.18 (s, 1H), 7.00 (s, 1H), 6.75 (s, 1H), 2.03 (d, 3H). |
| B11 | 4,4,4-trifluorobutanal | 46 | acetone-d6: 9.60 ppm (s, 1H), 7.53 (s, 1H), 7.19 (s, 1H), 6.82 (s, 1H), 3.65 (q, 2H). |

(E)-3-(5-Bromofuran-2-yl)allylidene]malononitrile (B2)

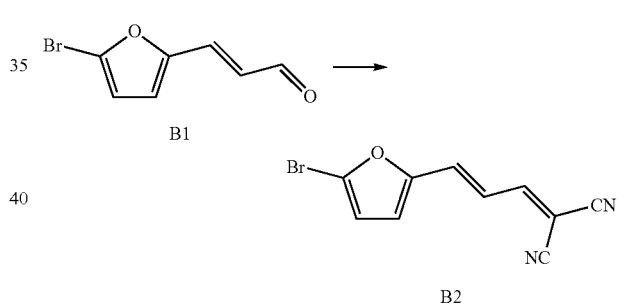

36.7 mmol of (E)-3-(5-bromofuran-2-yl)propenal and 44.0 mmol of malonitrile were dissolved in 50 mL of ethanol. 3.7 mmol of β-alanine were added thereto and the reaction mixture was stirred at room temperature for 24 h. The precipitated solids were briefly heated to boiling and then cooled in an ice bath. The crystallized solids were filtered off and washed with a little ethanol. After drying in a desiccator, 3.49 g of [(E)-3-(5-bromofuran-2-yl)allylidene]-malononitrile B2 (38% yield) were isolated. EI m/z: 250[M], 169, 141, 114.

(E)-3-(5-Trimethylstannylfuran-2-yl)propenal (B3)

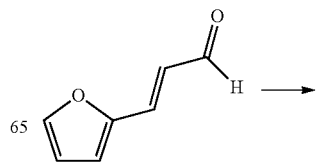

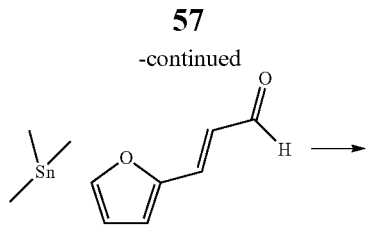

B3

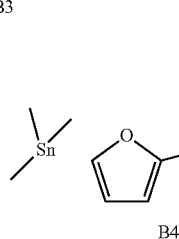

B4

To a solution of 3.06 g (29.9 mmol) of 1-methylpiperazine in 82 mL of anhydrous THF were added dropwise, under an argon atmosphere at −78° C., 12 mL (30 mmol) of n-butyllithium solution (2.5M in hexane). After stirring for 15 min, 3.15 g (25.0 mmol) of trans-3-(2-furyl)-acrolein were added dropwise. After stirring for a further 15 min, 3.95 g (33.7 mmol) of N,N,N',N'-tetramethylethylenediamine were added dropwise. After stirring for 15 min, 13.4 mL (33.5 mmol) of n-butyllithium solution (2.5M in hexane) were added dropwise. The reaction mixture was stirred at −20° C. for 3 h and then cooled down again to −78° C. At this temperature, 29.9 mL (29.9 mmol) of a 1M solution of trimethyltin chloride in THF were added and the mixture was then stirred at R.T. for 16 h. Subsequently, 100 mL of water were added, the organic phase was removed, the aqueous phase was extracted three times with MTBE and the combined organic phases were washed with 80 mL each of a 1M hydrochloric acid, saturated ammonium chloride solution and brine. After drying over sodium sulfate, the solvents were distilled off and the residue was purified by chromatography (SiO$_2$, petroleum ether/MTBE 5/1). Yield 5.52 g (76%). $^1$H NMR (400 MHz) in acetone-d6: 0.38 (s, 9H), 6.48 (dd, 1H), 6.84 (d, 1H), 6.97 (d, 1H), 7.51 (d, 1H), 9.63 (d, 1H).

2-[(E)-3-(5-Trimethylstannanylfuran-2-yl)allylidene]malononitrile (B4)

Under an argon atmosphere, 9.52 g (33.4 mmol) of B3 and 2.23 g (33.4 mmol) of malonitrile were dissolved in 19 mL of ethanol. 152 mg (1.67 mmol) of beta-alanine were added and the mixture was stirred at R.T. for 4 h. Subsequently, the mixture was heated to reflux temperature and gradually cooled down to 0° C. while stirring. The precipitate was filtered off, washed with 2 mL of ethanol and dried under reduced pressure: 9.10 g (82%) of orange crystalline solids. $^1$H NMR (400 MHz) in acetone-d6: 0.41 (s, 9H), 6.90 (d, 1H), 7.07 (m, 2H), 7.46 (d, 1H), 8.01 (d, 1H)

2-[(E)-3-(5-Bromofuran-2-yl)-1-methylallylidene]malononitrile (B6)

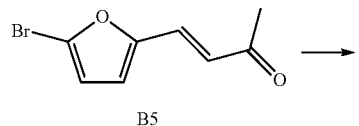

B5

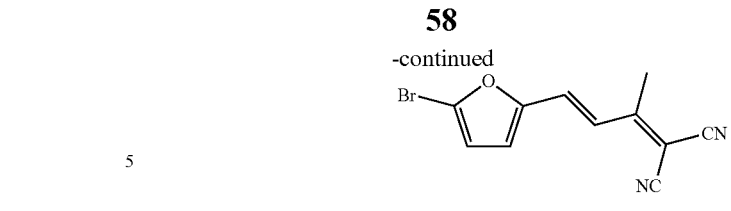

B6

1.61 g (7.47 mmol) of (E)-4-(5-bromofuran-2-yl)but-3-en-2-one (B5) and 2.47 g (37.4 mmol) of malononitrile were dissolved in 60 mL of 1,2-dichloroethane under an argon atmosphere. 4.29 g (14.9 mmol) of titanium(IV) isopropoxide were added and the reaction mixture was heated to 110° C. for 20 h. The mixture was allowed to cool to RT, and 100 mL of 1N HCl solution were added. The mixture was stirred at RT for 1 h, then the phases were separated and the aqueous phase was extracted with DCM. The combined organic phases were washed with 1N HCl solution and sat. NaHCO$_3$ solution, dried over Na$_2$SO$_4$ and filtered. The solvents were distilled off under reduced pressure and the residue chromatographically using silica gel (R$_F$ (PE:DCM (1:2))=0.30). This gave 1.08 g of product B6 (55%) as an orange solid. $^1$H NMR (acetone-d6): 7.46 ppm (d, 1H), 7.17 (d, 1H), 7.03 (d, 1H), 6.76 (d, 1H), 2.48 (s, 3H).

5-Trimethylstannylfuran-2-carbaldehyde (B7)

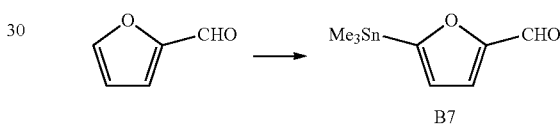

B7

To a solution of 6.13 g (60.0 mmol) of 1-methylpiperazine in 160 mL of anhydrous THF under an argon atmosphere at −78° C. were added dropwise 22.4 mL (56.0 mmol) of n-butyllithium solution (2.5 M in hexane). After stirring for 15 min, 4.85 g (50.0 mmol) of 2-furaldehyde were added dropwise. After stirring for a further 15 min, 7.92 g (67.5 mmol) of N,N,N',N'-tetramethylethylenediamine were added dropwise. After stirring for 15 min, 24.0 mL (60.0 mmol) of n-butyllithium solution (2.5 M in hexane) were added dropwise. The reaction mixture was stirred at −20° C. for 3 h and then cooled down again to −78° C. At this temperature, 60.0 mL (60.0 mmol) of a 1.0 M solution of trimethyltin chloride in THF were added and the mixture was then stirred at RT for 16 h. Subsequently, 100 mL of water were added, the organic phase was removed, the aqueous phase was extracted three times with MTBE and the combined organic phases were washed with 80 mL each of a 1 M hydrochloric acid and sat. sodium chloride solution. After drying over sodium sulfate, the solvents were distilled off and the residue was purified by chromatography (SiO$_2$, PE/MTBE 4/1). Yield 8.69 g (67%) as a yellow oil. 1H NMR (400 MHz) in acetone-d6: 9.67 ppm (s, 1H), 7.39 (d, 1H), 6.90 (d, 1H), 0.40 (s, 9H).

(E)-4-(5-Trimethylstannylfuran-2-yl)-but-3-en-2-one (B8)

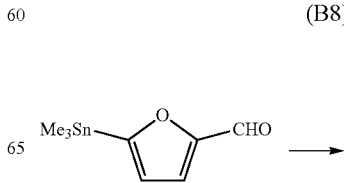

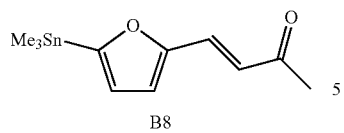

B8

To a solution of 8.69 g (33.5 mmol) of 5-trimethylstannylfuran-2-carbaldehyde (B7) in 67 mL of THF were added, under an argon atmosphere, 11.3 g (35.2 mmol) of 1-(triphenylphosphoranylidene)-2-propanone. The reaction mixture was heated to 50° C. for 96 h. The solvent was distilled off and the residue was purified by chromatography (SiO$_2$, PE/EA 3/1). Yield 9.14 g (91%) as a yellow oil. 1H NMR (400 MHz) in acetone-d6: 7.42 ppm (d, 1H), 6.85 (d, 1H), 6.80 (d, 1H), 6.54 (d, 1H), 2.28 (s, 3H), 0.34 (s, 9H).

2-[(E)-3-(5-Bromofuran-2-yl)-2-methylallylidene]malononitrile (B10)

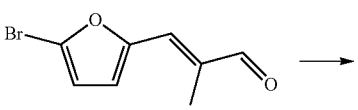

B9

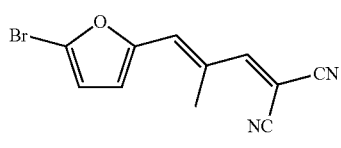

B10

B10 (as B2): yield 81%, $^1$H NMR in d6-acetone, ppm: 7.82 (s, 1H), 7.13 (s, 1H), 7.09 (d, 1H), 6.81 (d, 1H), 2.48 (s, 3H).

2-{2-[1-(5-Bromofuran-2-yl)meth-(E)-ylidene]-4,4,4-trifluoro-butylidene}malononitrile (B12)

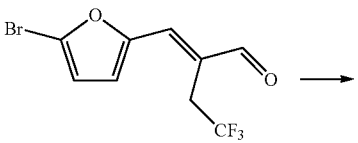

B11

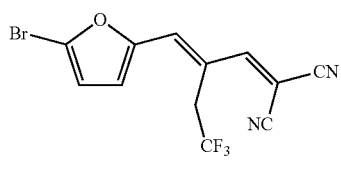

B12

The synthesis of B12 is effected in an analogous manner to B2. Yield 58%, $^1$H NMR in d6-acetone, ppm: 7.93 (s, 1H), 7.47 (s, 1H), 7.24 (d, 1H), 6.87 (d, 1H), 4.10 (qa, 2H).

3-(5-Bromofuran-2-yl)cyclohex-2-enone (B13)

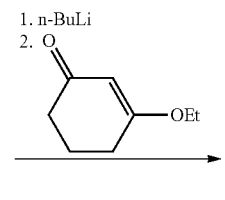

To a solution of 2.00 g of 2,5-dibromofuran (8.85 mmol) in 25 mL of diethyl ether at −65° C. under an argon atmosphere were added dropwise, while stirring, 5.53 mL of n-butyllithium (1.6M in hexane) within 15 min. After a further 15 min, 1.86 g of 3-ethoxy-2-cyclohexen-1-one (13.3 mmol) were added and the mixture was warmed to R.T. overnight. The mixture was added to 150 mL of brine and extracted with 3×100 mL of dichloromethane. The combined organic extracts were washed with 2M hydrochloric acid and dried over sodium sulfate, and the solvents were removed under reduced pressure. After purification by column chromatography (SiO$_2$, dichloromethane), B13 was obtained as a yellow crystalline solid (1.08 g, 4.48 mmol, 51%). $^1$H NMR (CDCl$_3$): 6.68 ppm (d, 1H), 6.44-6.43 (m, 2H), 2.60 (td, 2H), 2.46 (t, 2H), 2.14-2.07 (m, 2H).

2-[3-(5-Bromofuran-2-yl)cyclohex-2-enylidene]malononitrile (B14)

Under an argon atmosphere, 1.68 g of ammonium acetate (21.8 mmol) were added to a solution of 1.74 g B13 (7.14 mmol) and 1.42 g of malononitrile (21.5 mmol) in dichloroethane. The mixture was refluxed for 2 h, then 20 mg of 1,4-diazabicyclo[2.2.2]octane (0.178 mmol) were added and then the mixture was refluxed for a further 16 h. The reaction mixture was added to 100 mL of water and extracted with 3×50 mL of dichloromethane. The combined organic extracts were washed with 100 mL of water and dried over sodium sulfate, and the solvents were removed under reduced pressure. After purification by column chromatography (SiO$_2$, hexane), B14 was obtained as an orange crystalline solid (1.15 g, 3.98 mmol, 91%). $^1$H NMR (CDCl$_3$): 7.19 ppm (s, 1H), 6.79 (d, 1H), 6.49 (d, 1H), 2.80 (t, 2H), 2.64-2.61 (m, 2H), 2.00-1.94 (m, 2H).

3-(5-Bromofuran-2-yl)-2-methylcyclopent-2-enone (B15)

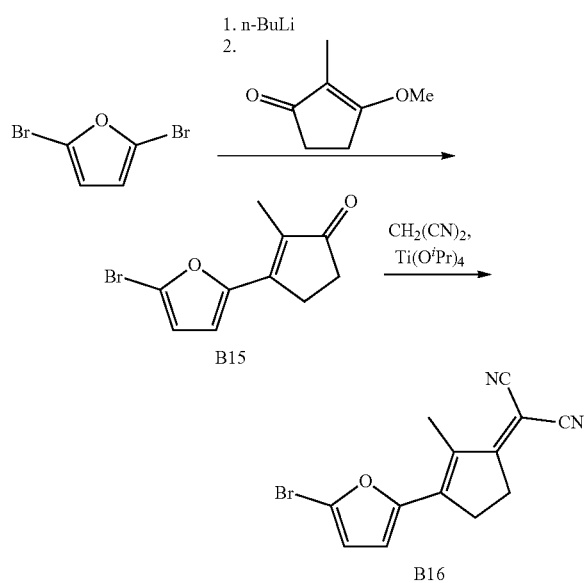

2-(5-Trimethylstannylfuran-2-ylmethylene)malononitrile (B17)

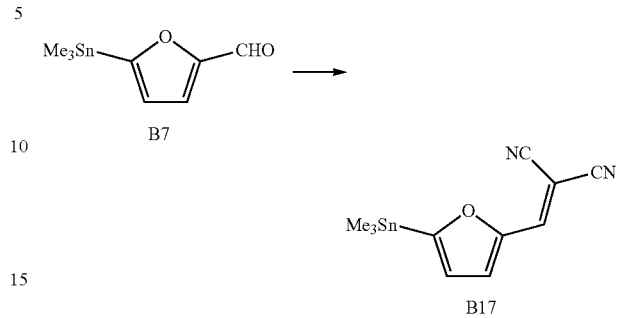

The synthesis of B17 proceeding from B7 is analogous to B4

Synthesis of Reactant C2

The reactants needed for the simple Stille coupling can, as already described, be prepared from the electron-rich stannyl compound and the electron-deficient bromide. Analogously, there are various different options known from the literature for this purpose. The preparation of reactant C1 was accomplished here using Stille coupling reactions. With N-iodosuccinimide, it was possible to convert C1 as starting point for a new Stille coupling reaction to C2.

2-[5-(2,3-Dihydrothieno[3,4-b][1,4]dioxin-5-yl)furan-2-ylmethylene]-malononitrile (C1)

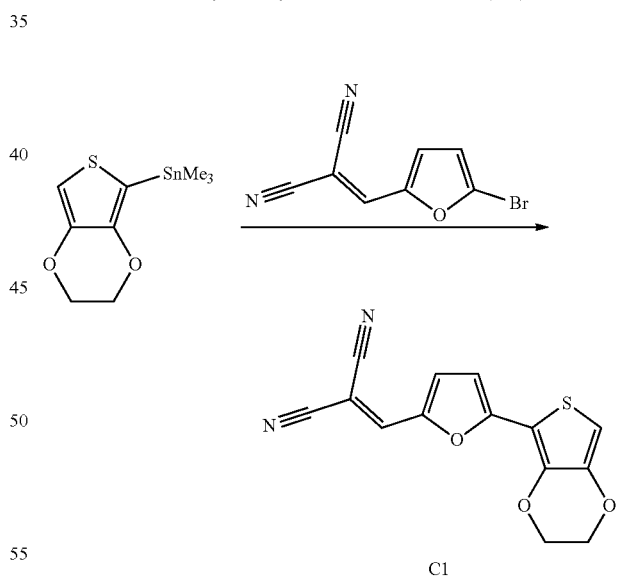

To a solution of 3.46 g of 2,5-dibromofuran (15 mmol) in 45 mL of diethyl ether at −65° C. under an argon atmosphere were added dropwise, while stirring, 6.00 mL of n-butyllithium (2.5M in hexane, 15 mmol) within 30 min. After a further 15 min, 2.94 g of 3-ethoxy-2-methyl-2-cyclopenten-1-one (21.0 mmol) dissolved in 15 mL of diethyl ether were added and the mixture was stirred at −65° C. for 1.5 h and then warmed to R.T. overnight. After the addition of 150 mL of dichloromethane, the mixture was added to 300 mL of 1M hydrochloric acid. The organic phase was removed and the aqueous phase was extracted once with 100 mL of dichloromethane. The combined organic phases were washed with 2M hydrochloric acid (150 mL) and water (100 mL) and dried over sodium sulfate, and the solvents were removed under reduced pressure. After purification by column chromatography, (SiO$_2$, dichloromethane/hexane), B15 was obtained as a yellow crystalline solid (2.10 g, 8.71 mmol, 58%). $^1$H NMR (CDCl$_3$): 6.75 ppm (d, 1H), 6.50 (d, 1H), 2.86-2.82 (m, 2H), 2.52-2.49 (m, 2H), 2.02 (t, 3H).

2-[3-(5-Bromofuran-2-yl)-2-methylcyclopent-2-enylidene]malononitrile (B16)

To a solution of 1.30 g of 3-(5-bromofuran-2-yl)-2-methylcyclopent-2-enone (B15) (5.39 mmol) and 3.60 g of malononitrile (53.9 mmol) in 1,2-dichloroethane were added, under an argon atmosphere, 3.09 g of tetraisopropyl orthotitanate (10.8 mmol) and the mixture was stirred under reflux for 3 d. The reaction mixture was poured onto hydrochloric acid (1M, 200 mL), stirred vigorously for 30 min and extracted with dichloromethane (3×100 mL). The combined organic phases were washed with water (100 mL), dried over sodium sulfate and filtered, and the solvent was removed under reduced pressure. Purification by column chromatography (silica gel, dichloromethane) gave B16 (1.37 mg, 4.75 mmol, 88%) as an orange crystalline solid. $^1$H NMR (CDCl$_3$): 6.82 ppm (d, 1H), 6.55 (d, 1H), 3.09-3.06 (m, 2H), 3.00-2.96 (m, 2H), 2.40 (t, 3H).

1.49 g (4 mmol) of (2,3-dihydrothieno[3,4-b][1,4]dioxin-5-yl)-trimethylstannane and 0.89 g (4 mmol) of C4 were dissolved in 20 mL of dry toluene and the reaction mixture was degassed. Subsequently, 140 mg (0.12 mmol) of tetrakis(triphenylphosphine)palladium(0) were added and the reaction mixture was heated to boiling overnight. The reaction mixture was brought to room temperature, and 300 mL of dichloromethane were added. The organic phase was removed, washed three times with sat. NaCl solution and dried over sodium sulfate. The solvent was removed on a rotary evaporator. The residue was chromatographed using silica gel in petroleum ether/DCM=1/3 (Rf 0.1). This gives 982 mg of C1. ¹H NMR (CDCl3) ppm: 7.18 (s, 2H), 6.81 (d, 1H), 6.47 (d, 1H), 4.30 (m, 2H), 4.21 (m, 2H).

2-[5-(7-Iodo-2,3-dihydrothieno[3,4-b][1,4]dioxin-5-yl)furan-2-ylmethylene]malononitrile (C2)

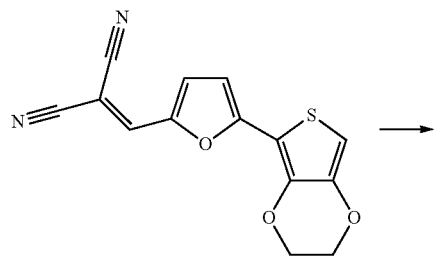

C1

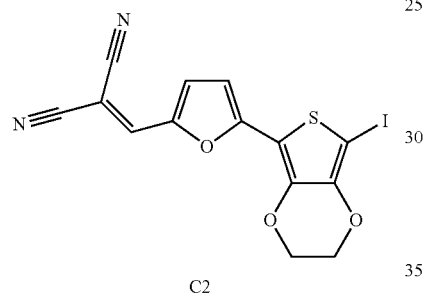

C2

301 mg (1.06 mmol) of C1 were dissolved in 6 mL of dry DMF and cooled down to 0° C. under argon. 241 mg (1.06 mmol) of N-iodosuccinimide were added in portions and then stirred at room temperature overnight. Ice-water was added to the reaction mixture, which was brought to room temperature while stirring. The aqueous mixture was extracted three times with 50 mL of dichloromethane. The organic phase was washed twice with 50 mL of sat. NaCl solution and once with 50 mL of 5% LiCl solution, and dried over sodium sulfate. The solvent was removed by rotary evaporator, and the residue was chromatographed using silica gel with dichloromethane (Rf 0.58). This gives 413 mg of C2. ¹H NMR (CDCl3) ppm: 7.35 (s, 1H), 6.55 (d, 2H), 4.32 (m, 4H).

2-(5-Bromothiophen-2-ylmethylene)malononitrile (C3)

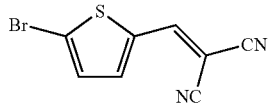

C3

2-(5-Bromofuran-2-ylmethylene)malononitrile (C4)

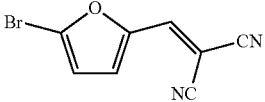

C4

Compounds C3 and C4 are prepared in accordance with the synthesis described in the literature (Qi et al., J. Mat. Chem. 2008, 18, 1131).

2-[5-(5,6-Dihydro-4H-cyclopenta[c]thiophen-1-yl)furan-2-ylmethylene]-malononitrile (C5)

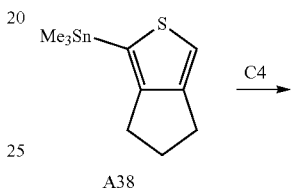

A38

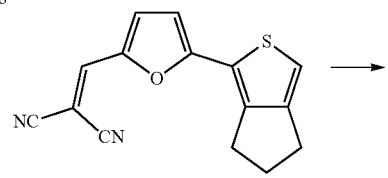

C5

2.10 g (7.32 mmol) of 2-trimethylstannyl-5,6-dihydro-4H-cyclopenta[c]thiophene (A38) and 1.63 g (7.32 mmol) of 2-[(5-bromofuran-2-yl)methylene]malononitrile (C4) were dissolved in 28 mL of 1,4-dioxane. 37 mg (73 µmol) of bis(tri-tert-butylphosphine)-palladium(0) were added and the mixture was heated to 80° C. for 16 h. After it had been cooled down to room temperature, water was added to the reaction mixture and it was extracted three times with ethyl acetate. The combined organic phases were washed with water and sat. NaCl solution. They were dried over Na2SO4 and filtered, and the solvents were removed under reduced pressure. The residue was purified by chromatography (SiO2, Rf (Hex:DCM (1:1))=0.19), and 1.50 g of product C5 (68%) were obtained red solid. 1H NMR (acetone-D6): 7.91 ppm (s, 1H), 7.54 (d, 1H), 7.19 (1s, 1H), 6.91 (d, 1H), 2.97 (t, 2H), 2.72 (t, 2H), 2.44-2.51 (m, 2H).

2-[5-(3-Bromo-5,6-dihydro-4H-cyclopenta[c]thiophen-1-yl)furan-2-ylmethylene]malononitrile (C6)

266 mg (1.00 mmol) of 2-[5-(5,6-dihydro-4H-cyclopenta[c]thiophen-1-yl)furan-2-ylmethylene]malononitrile (C5) were dissolved in 10 mL of THF at 0° C. under an argon atmosphere. 178 mg (1.00 mmol) of NBS were added in portions and the mixture was stirred at 0° C. for 15 min. The mixture was warmed to RT and stirred for a further 16 h. The reaction mixture was cooled to 0° C. and the precipitate was filtered off. The precipitate was dried under reduced pressure and 244 mg of product C6 (71%) were obtained as a red solid. 1H NMR (acetone-D6): 7.97 ppm (s, 1H), 7.54 (d, 1H), 6.91 (d, 1H), 3.05 (t, 2H), 2.65 (t, 2H), 2.47-2.55 (m, 2H).

Synthesis of C7 and C8

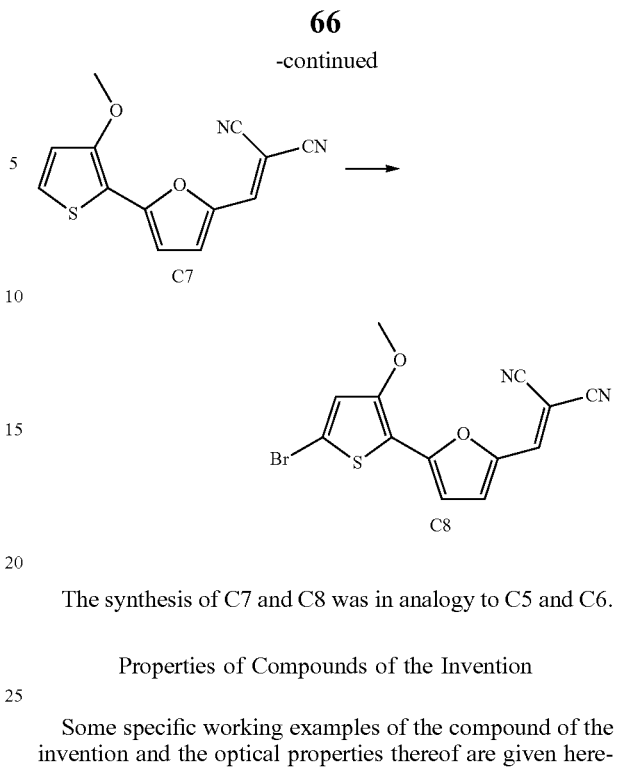

The synthesis of C7 and C8 was in analogy to C5 and C6.

Properties of Compounds of the Invention

Some specific working examples of the compound of the invention and the optical properties thereof are given hereinafter:

TABLE 5

Overview of working examples and optical properties

| No. | Structure | λmax (solv.)/ nm[b] | FWHM film*/eV[c] |
|---|---|---|---|
| 1 | 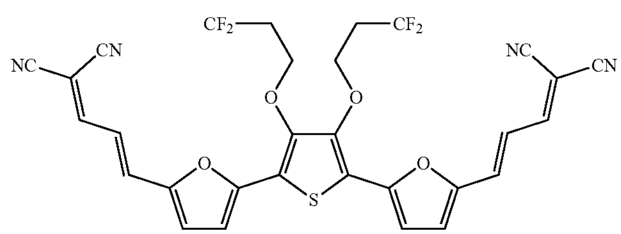 | 435 | 2.20 |
| 2 | 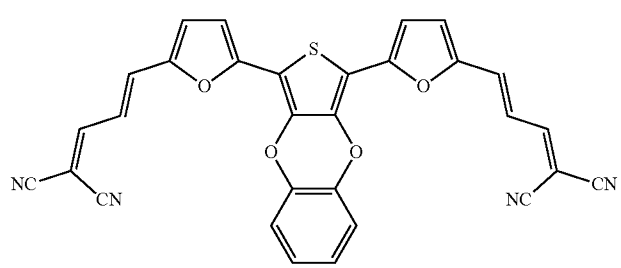 [SMILES: N#CC(C#N)=C/C=C/c1ccc(-c2sc(-c3ccc(/C=C/C=C(C#N)C#N)o3)c3c2Oc2ccccc2O3)o1] | 444 | 1.17 |
| 3 | 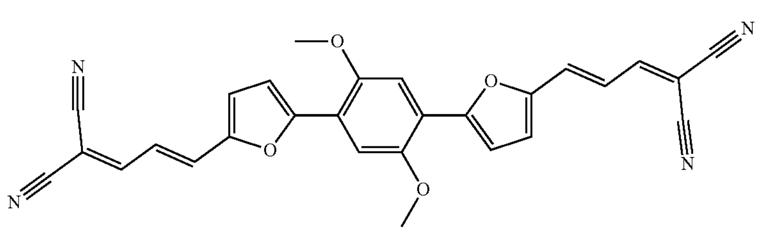 [SMILES: COc1cc(-c2ccc(/C=C/C=C(C#N)C#N)o2)c(OC)cc1-c1ccc(/C=C/C=C(C#N)C#N)o1] | 534 | 0.83 |

TABLE 5-continued

Overview of working examples and optical properties

| No. | Structure | λmax (solv.)/ nm[b] | FWHM film*/eV[c] |
|---|---|---|---|
| 4 | 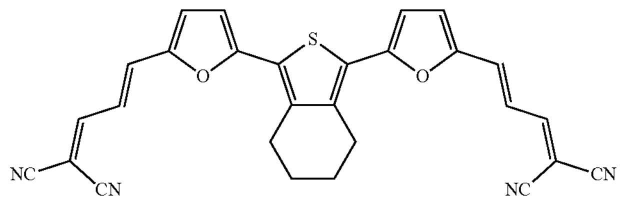 | 540 | 1.09 |
| 5 | 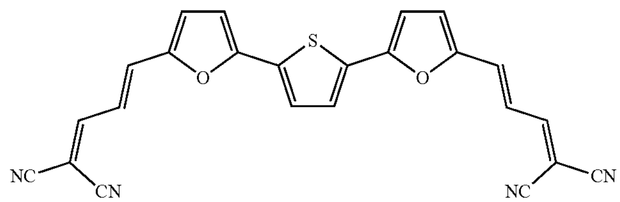 [SMILES: N#CC(C#N)=C/C=C/c1ccc(-c2ccc(-c3ccc(/C=C/C=C(C#N)C#N)o3)s2)o1] | 542 | 1.14 |
| 6 | 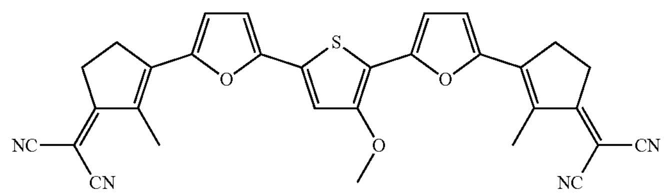 [SMILES: COc1cc(-c2ccc(C3=C(C)C(=C(C#N)C#N)CC3)o2)sc1-c1ccc(C2=C(C)C(=C(C#N)C#N)CC2)o1] | 542 | 1.30 |
| 7 | 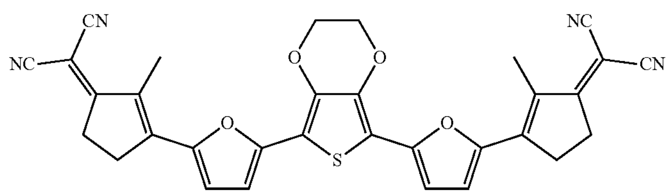 [SMILES: CC1=C(c2ccc(-c3sc(-c4ccc(C5=C(C)C(=C(C#N)C#N)CC5)o4)c4c3OCCO4)o2)CCC1=C(C#N)C#N] | 542 | 1.42 |
| 8 | 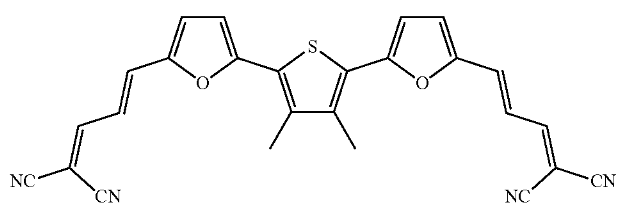 [SMILES: Cc1c(-c2ccc(/C=C/C=C(C#N)C#N)o2)sc(-c2ccc(/C=C/C=C(C#N)C#N)o2)c1C] | 548 | 1.18 |
| 9 | 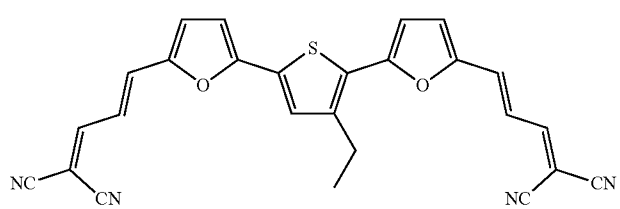 [SMILES: CCc1cc(-c2ccc(/C=C/C=C(C#N)C#N)o2)sc1-c1ccc(/C=C/C=C(C#N)C#N)o1] | 551 | 1.13 |
| 10 | 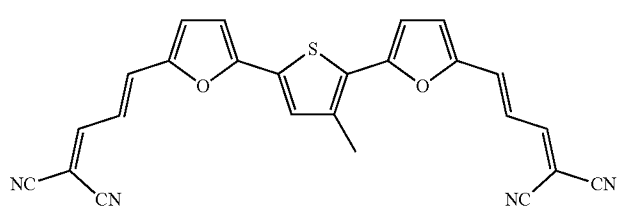 [SMILES: Cc1cc(-c2ccc(/C=C/C=C(C#N)C#N)o2)sc1-c1ccc(/C=C/C=C(C#N)C#N)o1] | 552 | 1.19 |

TABLE 5-continued

Overview of working examples and optical properties

| No. | Structure | λmax (solv.)/ nm[b] | FWHM film*/eV[c] |
|---|---|---|---|
| 11 | 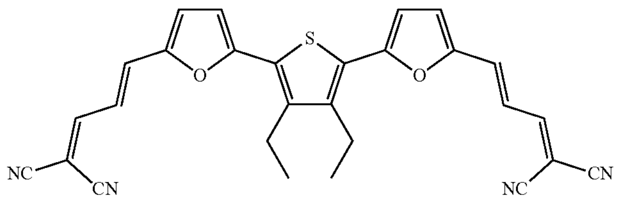 [SMILES: CCc1c(-c2ccc(/C=C/C=C(C#N)C#N)o2)sc(-c2ccc(/C=C/C=C(C#N)C#N)o2)c1CC] | 554 | 0.99 |
| 12 | 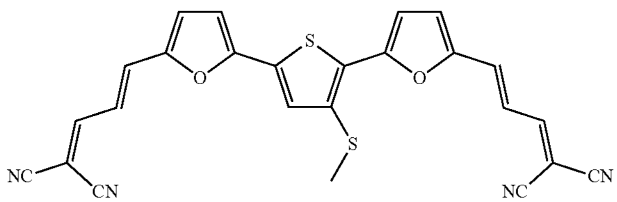 [SMILES: CSc1cc(-c2ccc(/C=C/C=C(C#N)C#N)o2)sc1-c1ccc(/C=C/C=C(C#N)C#N)o1] | 555 | 2.38 |
| 13 | 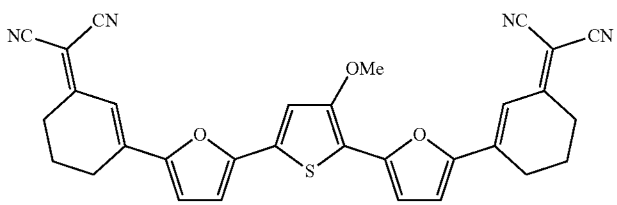 [SMILES: COc1cc(-c2ccc(C3=CC(=C(C#N)C#N)CCC3)o2)sc1-c1ccc(C2=CC(=C(C#N)C#N)CCC2)o1] | 556 | 1.24 |
| 14 | 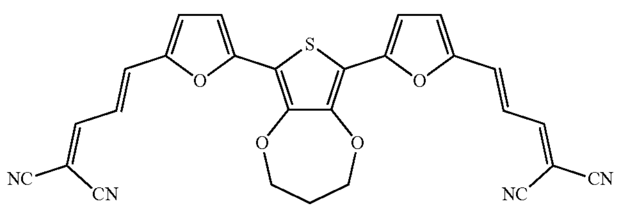 [SMILES: N#CC(C#N)=C/C=C/c1ccc(-c2sc(-c3ccc(/C=C/C=C(C#N)C#N)o3)c3c2OCCCO3)o1] | 562 (THF) | 2.41 |
| 15 | 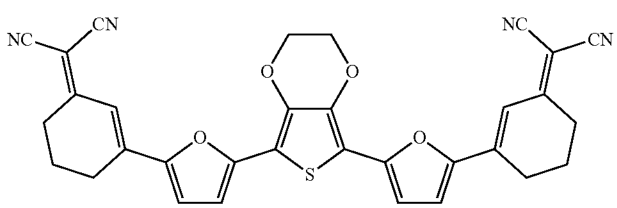 [SMILES: N#CC(C#N)=C1C=C(c2ccc(-c3sc(-c4ccc(C5=CC(=C(C#N)C#N)CCC5)o4)c4c3OCCO4)o2)CCC1] | 563 | 1.27 |
| 16 | 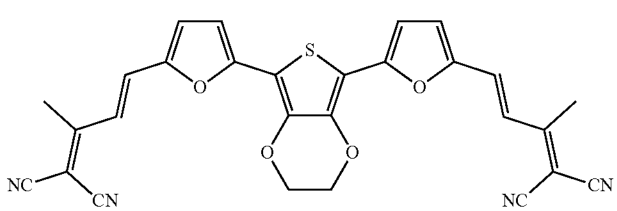 [SMILES: CC(/C=C/c1ccc(-c2sc(-c3ccc(/C=C/C(C)=C(C#N)C#N)o3)c3c2OCCO3)o1)=C(C#N)C#N] | 567 | 2.32 |
| 17 | 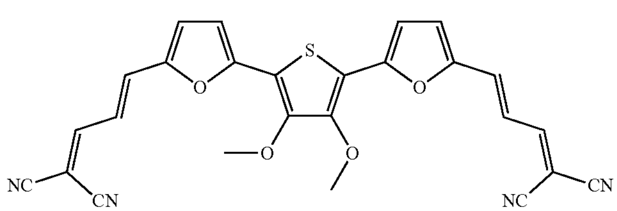 [SMILES: COc1c(-c2ccc(/C=C/C=C(C#N)C#N)o2)sc(-c2ccc(/C=C/C=C(C#N)C#N)o2)c1OC] | 568 | 1.91 |

TABLE 5-continued

Overview of working examples and optical properties

| No. | Structure | λmax (solv.)/ nm[b] | FWHM film*/eV[c] |
|---|---|---|---|
| 18 | 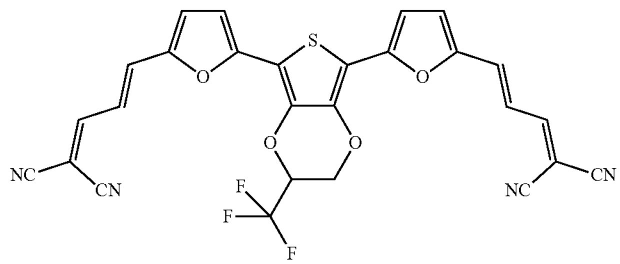 [SMILES: N#CC(C#N)=C/C=C/c1ccc(-c2sc(-c3ccc(/C=C/C=C(C#N)C#N)o3)c3c2OCC(C(F)(F)F)O3)o1] | 571 | 1.38 |
| 19 | 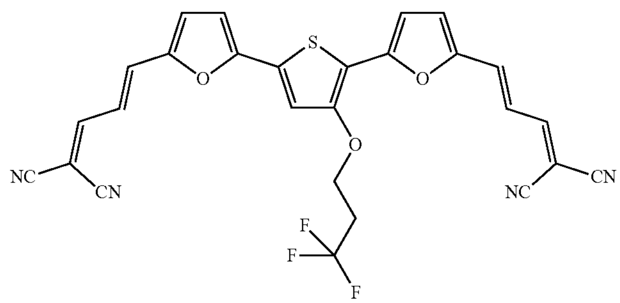 [SMILES: N#CC(C#N)=C/C=C/c1ccc(-c2cc(OCCC(F)(F)F)c(-c3ccc(/C=C/C=C(C#N)C#N)o3)s2)o1] | 574 | 1.22 |
| 20 | 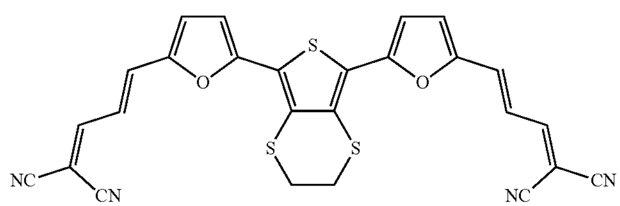 [SMILES: N#CC(C#N)=C/C=C/c1ccc(-c2sc(-c3ccc(/C=C/C=C(C#N)C#N)o3)c3c2SCCS3)o1] | 575 | 1.10 |
| 21 | 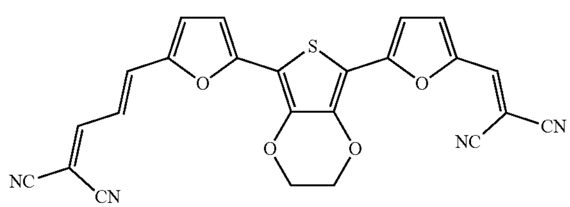 [SMILES: N#CC(C#N)=C/C=C/c1ccc(-c2sc(-c3ccc(C=C(C#N)C#N)o3)c3c2OCCO3)o1] | 577 | 1.38 |
| 22 | 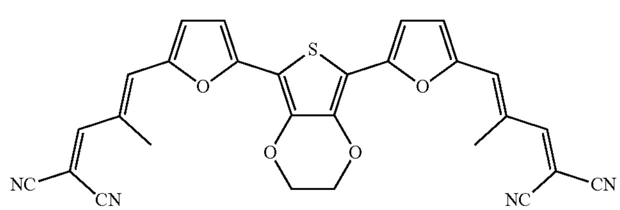 [SMILES: C/C(C=C(C#N)C#N)=C\c1ccc(-c2sc(-c3ccc(/C=C(\C)C=C(C#N)C#N)o3)c3c2OCCO3)o1] | 578 | 2.36 |
| 23 | 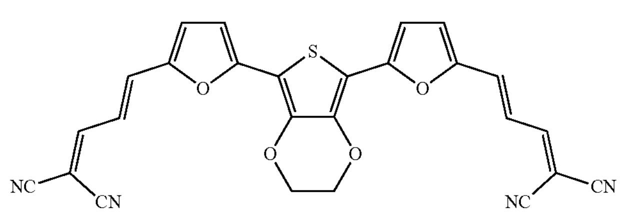 [SMILES: N#CC(C#N)=C/C=C/c1ccc(-c2sc(-c3ccc(/C=C/C=C(C#N)C#N)o3)c3c2OCCO3)o1] | 588 | 1.42 |

TABLE 5-continued

Overview of working examples and optical properties

| No. | Structure | λmax (solv.)/ nm[b] | FWHM film*/eV[c] |
|---|---|---|---|
| 24 | 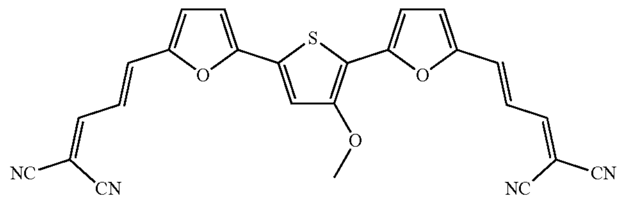 [SMILES: COc1cc(-c2ccc(/C=C/C=C(C#N)C#N)o2)sc1-c1ccc(/C=C/C=C(C#N)C#N)o1] | 591 | 1.31 |
| 25 | 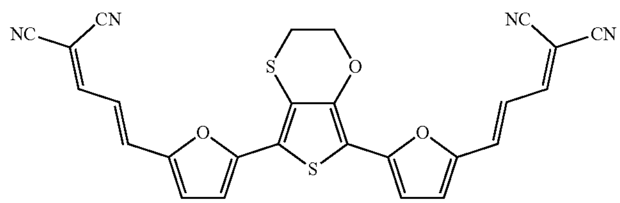 [SMILES: N#CC(C#N)=C/C=C/c1ccc(-c2sc(-c3ccc(/C=C/C=C(C#N)C#N)o3)c3c2OCCS3)o1] | 596 | 1.13 |
| 26 | 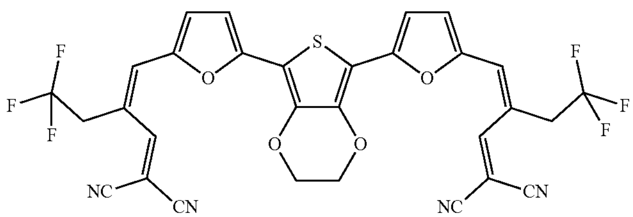 [SMILES: N#CC(C#N)=C/C(=C\c1ccc(-c2sc(-c3ccc(/C=C(\C=C(C#N)C#N)CC(F)(F)F)o3)c3c2OCCO3)o1)CC(F)(F)F] | 597 | 1.23 |
| 27 | 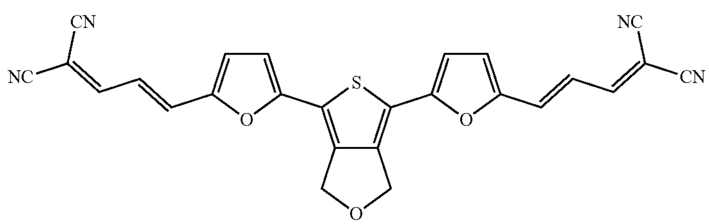 [SMILES: N#CC(C#N)=C/C=C/c1ccc(-c2sc(-c3ccc(/C=C/C=C(C#N)C#N)o3)c3c2COC3)o1] | 547 | 1.11 |
| 28 | 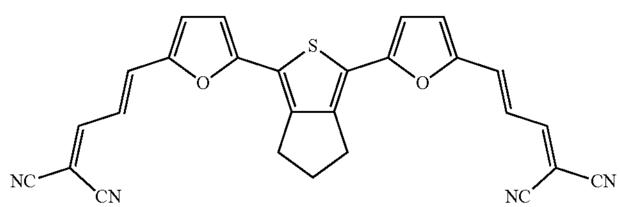 [SMILES: N#CC(C#N)=C/C=C/c1ccc(-c2sc(-c3ccc(/C=C/C=C(C#N)C#N)o3)c3c2CCC3)o1] | 572 | 1.10 |
| 29 | 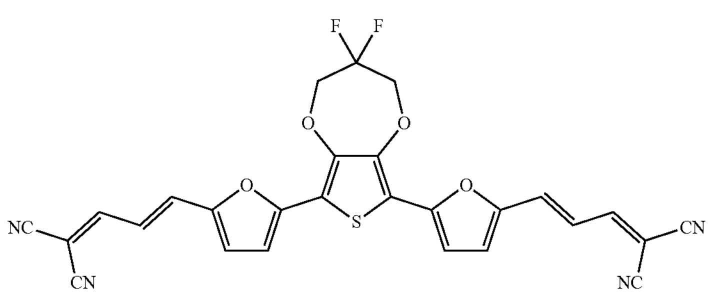 [SMILES: N#CC(C#N)=C/C=C/c1ccc(-c2sc(-c3ccc(/C=C/C=C(C#N)C#N)o3)c3c2OCC(F)(F)CO3)o1] | 550 | 2.22 |

TABLE 5-continued

Overview of working examples and optical properties

| No. | Structure | λmax (solv.)/nm[b] | FWHM film*/eV[c] |
|---|---|---|---|
| 30 | 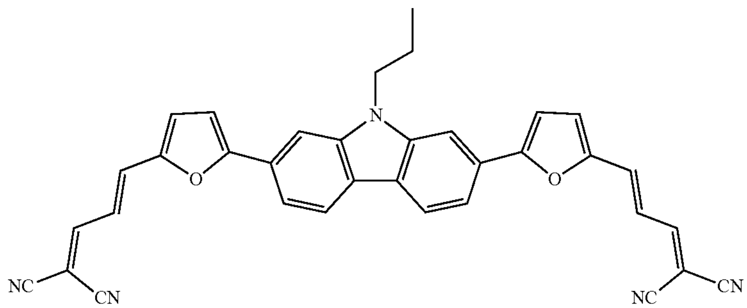 [SMILES: CCCn1c2cc(-c3ccc(/C=C/C=C(C#N)C#N)o3)ccc2c2ccc(-c3ccc(/C=C/C=C(C#N)C#N)o3)cc21] | 523 | 1.01 |
| 31 | 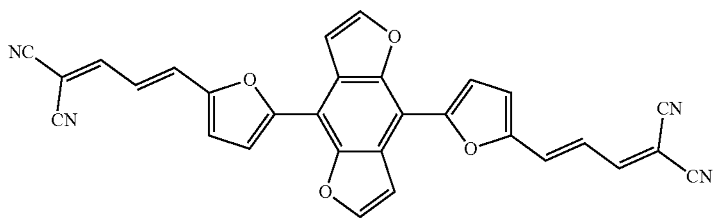 [SMILES: N#CC(C#N)=C/C=C/c1ccc(-c2c3ccoc3c(-c3ccc(/C=C/C=C(C#N)C#N)o3)c3ccoc23)o1] | 574 | 0.82 |
| 32 | 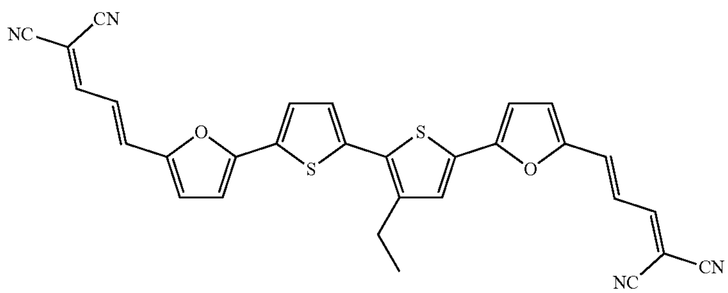 [SMILES: CCc1cc(-c2ccc(/C=C/C=C(C#N)C#N)o2)sc1-c1ccc(-c2ccc(/C=C/C=C(C#N)C#N)o2)s1] | 540 | 1.08 |
| 33 | 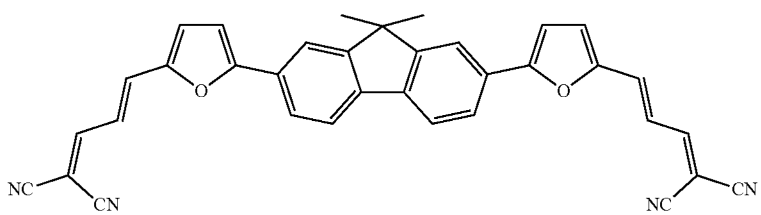 [SMILES: CC1(C)c2cc(-c3ccc(/C=C/C=C(C#N)C#N)o3)ccc2-c2ccc(-c3ccc(/C=C/C=C(C#N)C#N)o3)cc21] | 513 | 1.05 |
| 34 | 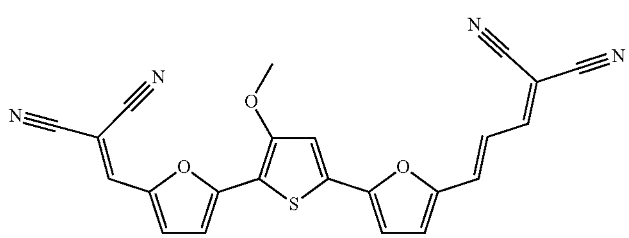 [SMILES: COc1cc(-c2ccc(/C=C/C=C(C#N)C#N)o2)sc1-c1ccc(C=C(C#N)C#N)o1] | 548 | 1.26 |
| 35 | 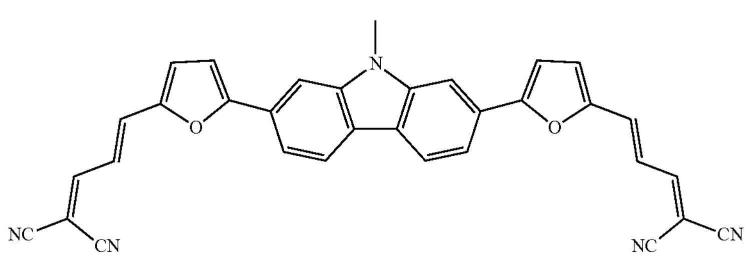 [SMILES: Cn1c2cc(-c3ccc(/C=C/C=C(C#N)C#N)o3)ccc2c2ccc(-c3ccc(/C=C/C=C(C#N)C#N)o3)cc21] | 527 | 0.99 |

TABLE 5-continued

Overview of working examples and optical properties

| No. | Structure | λmax (solv.)/ nm[b] | FWHM film*/eV[c] |
|---|---|---|---|
| 36 | 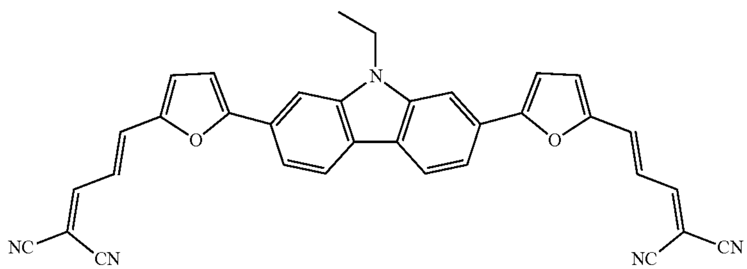 [SMILES: CCn1c2cc(-c3ccc(/C=C/C=C(C#N)C#N)o3)ccc2c2ccc(-c3ccc(/C=C/C=C(C#N)C#N)o3)cc21] | 519 | 0.97 |
| 37 | 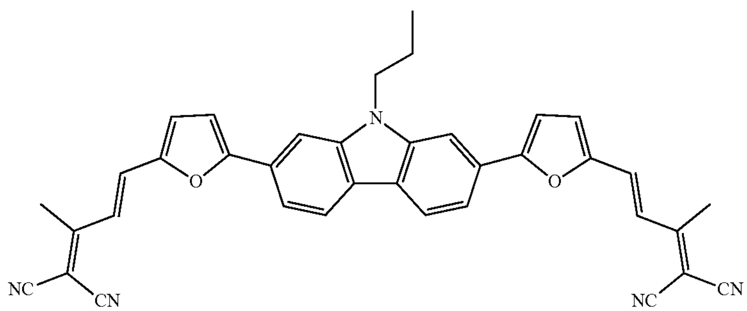 [SMILES: CCCn1c2cc(-c3ccc(/C=C/C(C)=C(C#N)C#N)o3)ccc2c2ccc(-c3ccc(/C=C/C(C)=C(C#N)C#N)o3)cc21] | 500 | 1.84 |
| 38 | 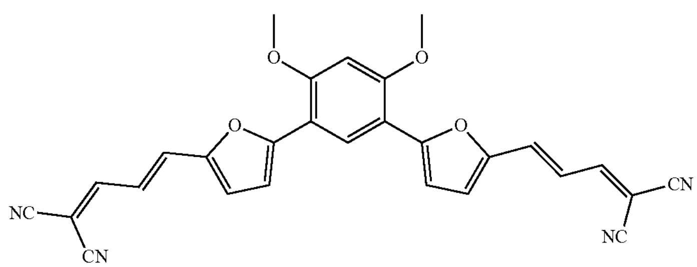 [SMILES: COc1cc(OC)c(-c2ccc(/C=C/C=C(C#N)C#N)o2)cc1-c1ccc(/C=C/C=C(C#N)C#N)o1] | 447 | 1.16 |
| 39 | 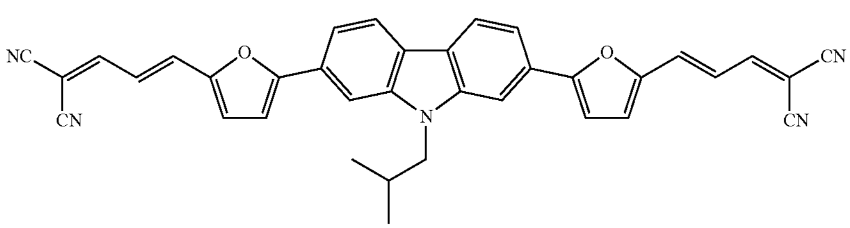 [SMILES: CC(C)Cn1c2cc(-c3ccc(/C=C/C=C(C#N)C#N)o3)ccc2c2ccc(-c3ccc(/C=C/C=C(C#N)C#N)o3)cc21] | 526 | 0.98 |
| 40 | 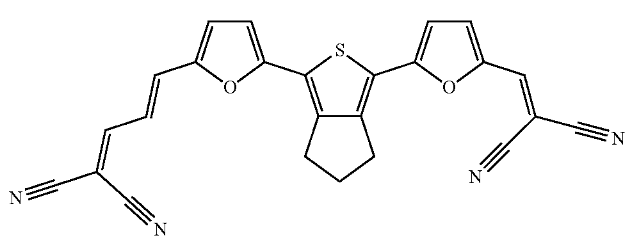 [SMILES: N#CC(C#N)=C/C=C/c1ccc(-c2sc(-c3ccc(C=C(C#N)C#N)o3)c3c2CCC3)o1] | 542 | 0.97 |

TABLE 5-continued

Overview of working examples and optical properties

| No. | Structure | λmax (solv.)/ nm[b] | FWHM film*/eV[c] |
|---|---|---|---|
| 41 | 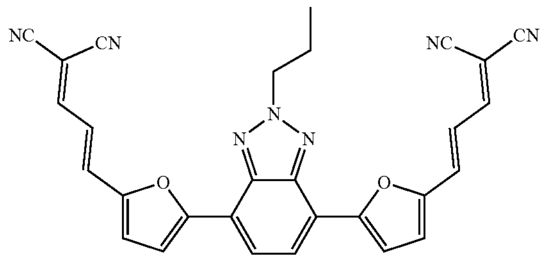 [SMILES: CCCn1nc2c(-c3ccc(/C=C/C=C(C#N)C#N)o3)ccc(-c3ccc(/C=C/C=C(C#N)C#N)o3)c2n1] | 526 | 1.30 |
| 42 | 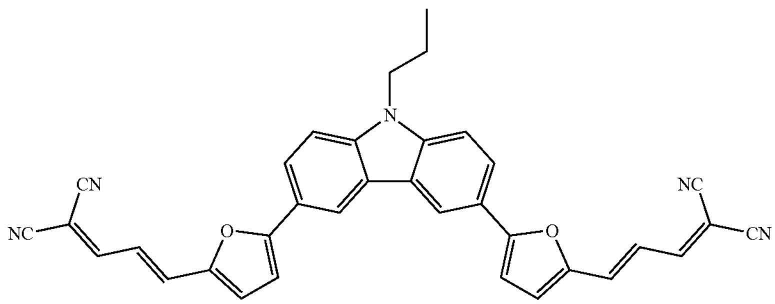 [SMILES: CCCn1c2ccc(-c3ccc(/C=C/C=C(C#N)C#N)o3)cc2c2cc(-c3ccc(/C=C/C=C(C#N)C#N)o3)ccc21] | 511 | 0.89 |
| 43 | 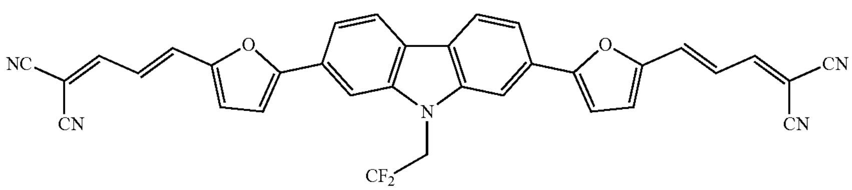 | 510 | 0.89 |
| 44 | 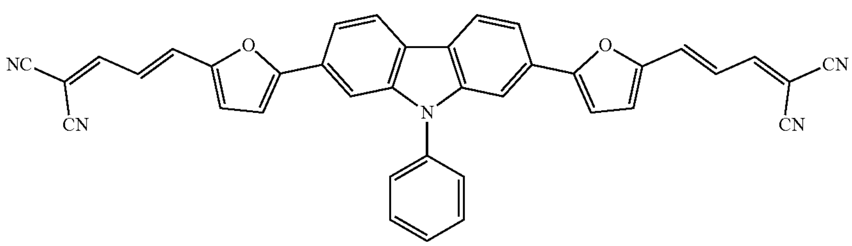 [SMILES: N#CC(C#N)=C/C=C/c1ccc(-c2ccc3c4ccc(-c5ccc(/C=C/C=C(C#N)C#N)o5)cc4n(-c4ccccc4)c3c2)o1] | 517 | 1.97 |
| 45 | 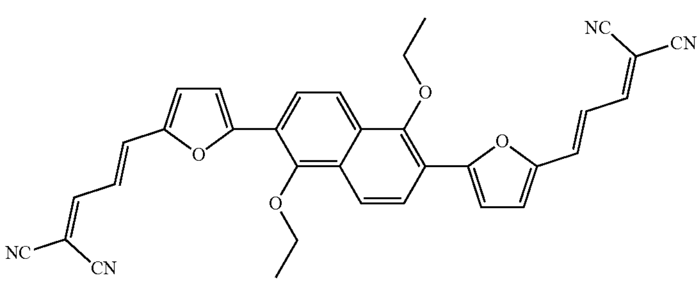 [SMILES: CCOc1c(-c2ccc(/C=C/C=C(C#N)C#N)o2)ccc2c(OCC)c(-c3ccc(/C=C/C=C(C#N)C#N)o3)ccc12] | 518 | 0.77 |

TABLE 5-continued

Overview of working examples and optical properties

| No. | Structure | λmax (solv.)/ nm[b] | FWHM film*/eV[c] |
|---|---|---|---|
| 46 | 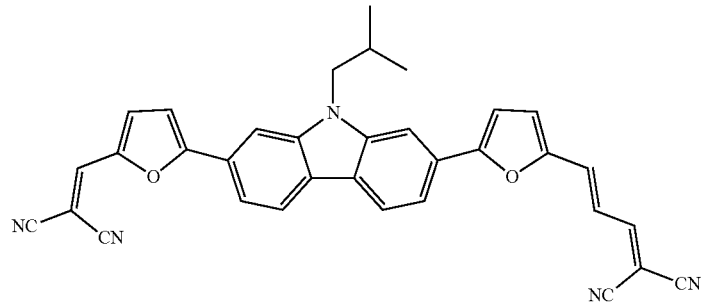 [SMILES: CC(C)Cn1c2cc(-c3ccc(C=C(C#N)C#N)o3)ccc2c2ccc(-c3ccc(/C=C/C=C(C#N)C#N)o3)cc21] | 511 | 1.04 |
| 47 | 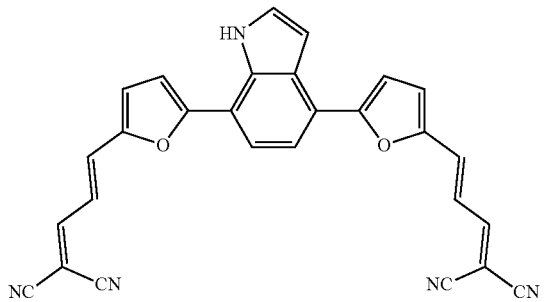 [SMILES: N#CC(C#N)=C/C=C/c1ccc(-c2ccc(-c3ccc(/C=C/C=C(C#N)C#N)o3)c3[nH]ccc23)o1] | 554 | 1.08 |
| 48 | 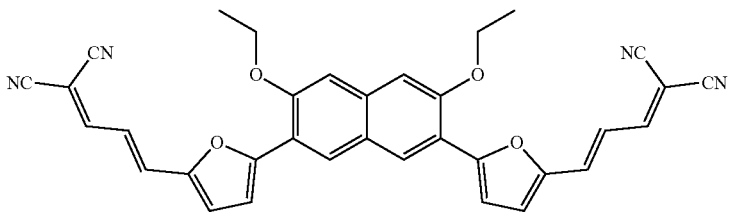 [SMILES: CCOc1cc2cc(OCC)c(-c3ccc(/C=C/C=C(C#N)C#N)o3)cc2cc1-c1ccc(/C=C/C=C(C#N)C#N)o1] | 455 | 87 |

[a]DSC onset [b] in dichloromethane unless stated otherwise
[c]30 nm in film applied by vapor deposition under reduced pressure DSC stands for differential scanning calorimetry (dynamic differential calorimetry).

The optical properties were determined experimentally in each case. The absorption maximum $\lambda_{max}$ in nm was ascertained with a dilute solution in a cuvette (in dichloromethane unless stated otherwise) with the aid of a photometer. The absorption maxima measured for all the compounds described are between 400 and 600 nm and thus overlap particularly advantageously with the energy maximum of the solar spectrum.

Further optical properties such as the full width at half maximum (FWHM) were determined directly on films of the organic compounds. For this purpose, by means of vacuum sublimation at $10^{-6}$ to $10^{-7}$ mbar, a film of thickness 30 nm of the respective compound of the invention was produced. The layer thickness was determined by means of a crystal oscillator monitor.

The compounds of the invention feature particularly high absorption in a broad spectrum of visible light, which is reflected in the high values achieved for the full width at half maximum. The compounds of the invention thus enable absorption of photons over a comparatively broad spectral range comprising a high proportion of short-wave visible sunlight and conversion thereof to electrical energy.

The invention is to be elucidated further hereinafter with reference to a series of figures.

FIG. 1 compares normalized absorption spectra in electron-volts (measured on: 30 nm film, vapor-deposited under reduced pressure, as described above). What is shown is a comparison of compound 23 with two comparative materials.

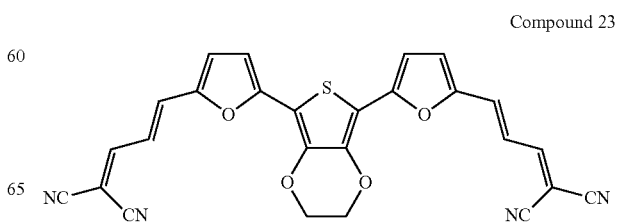

Compound 23

-continued

Comparative material 1

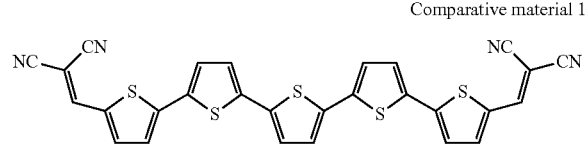

(Fitzner et al., Adv. Funct. Mat. 2011, 21, 897-910)

Comparative material 2

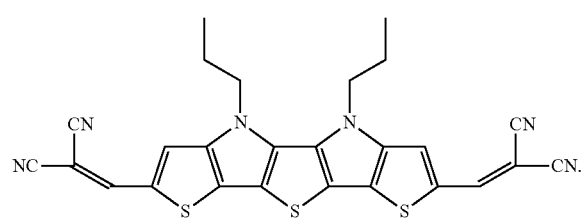

(Mishra et al., Adv. Mat. 2014, 26, 7217-7223)

The measurement compares the absorption plotted against the energy of the incident light in electron-volts. A particularly high full width at half maximum can be observed in the short-wave spectral region. Especially in the region of 2.5 eV and higher energies, i.e. for 500 nm or shorter wavelengths, compound 23 shows much higher absorption than the comparative materials. In general, the compounds of the invention, particularly in the range between 400 and 600 nm, show much better absorption properties. This makes it possible to generate photocurrents which utilize short-wave photons in a high proportion. These photons, by contrast, are frequently utilized only inadequately by conventional organic compounds.

Figure 2:
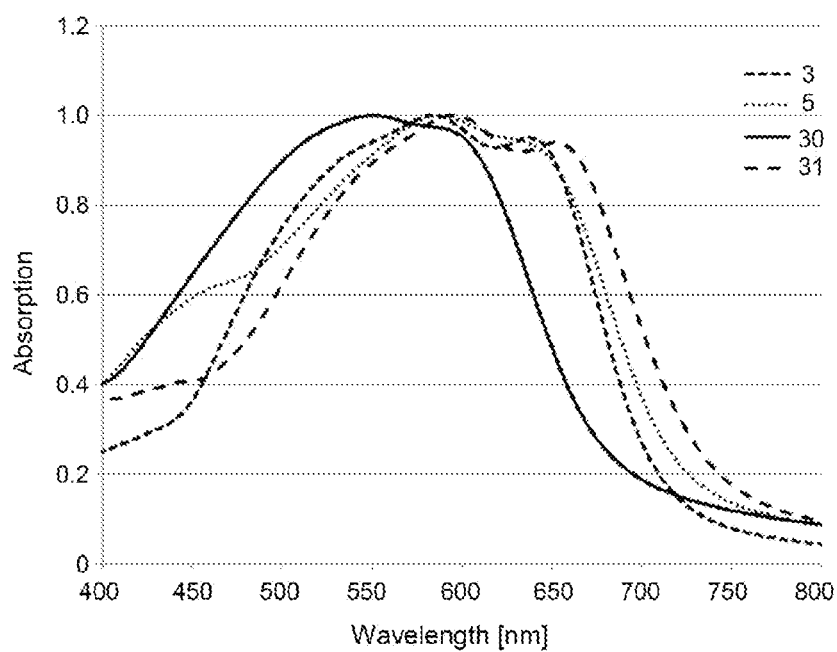
FIG. 2 shows absorption spectra of compounds 3, 5, 30, and 31.

FIG. 2 shows absorption spectra of inventive compounds 3, 5, 30, 31:

Compound 3

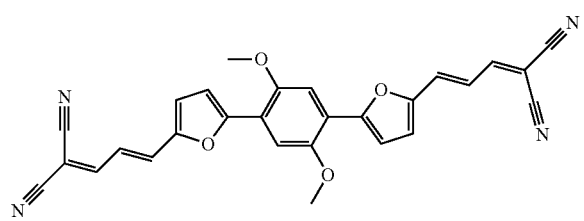

Compound 5

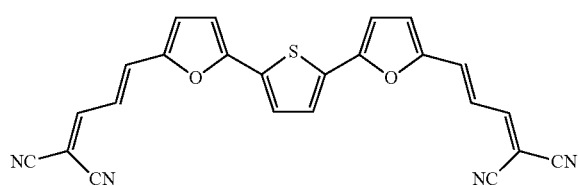

Compound 30

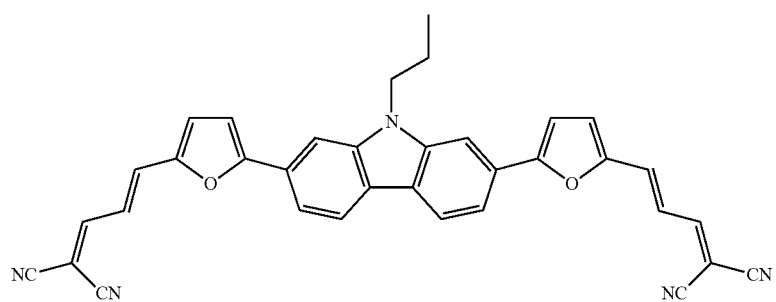

Compound 31

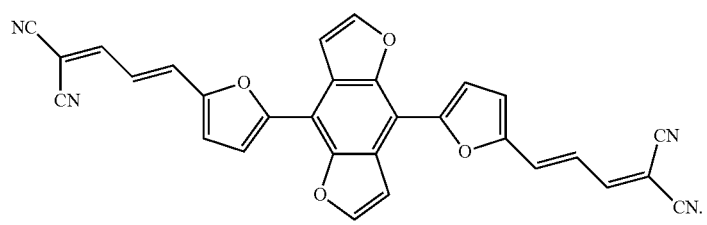

The absorption spectra were again obtained on films of the compounds having a thickness of 30 nm, which were produced and analyzed as specified above. The figure thus compares compounds of the invention which differ in the choice of structural units for the middle conjugated $D^1$-$D^3$ block. The spectrum shows the absorption plotted against the wavelength in nanometers. Astonishingly, all the specified compounds 3, 5, 30 and 31, in spite of the different kinds of middle conjugated blocks, show a very broad absorption spectrum with good absorption even in the region of short wavelengths. At the same time, through the utilization of different middle conjugated blocks, it is possible to achieve fine adjustments in the absorption spectrum.

Figure 3:
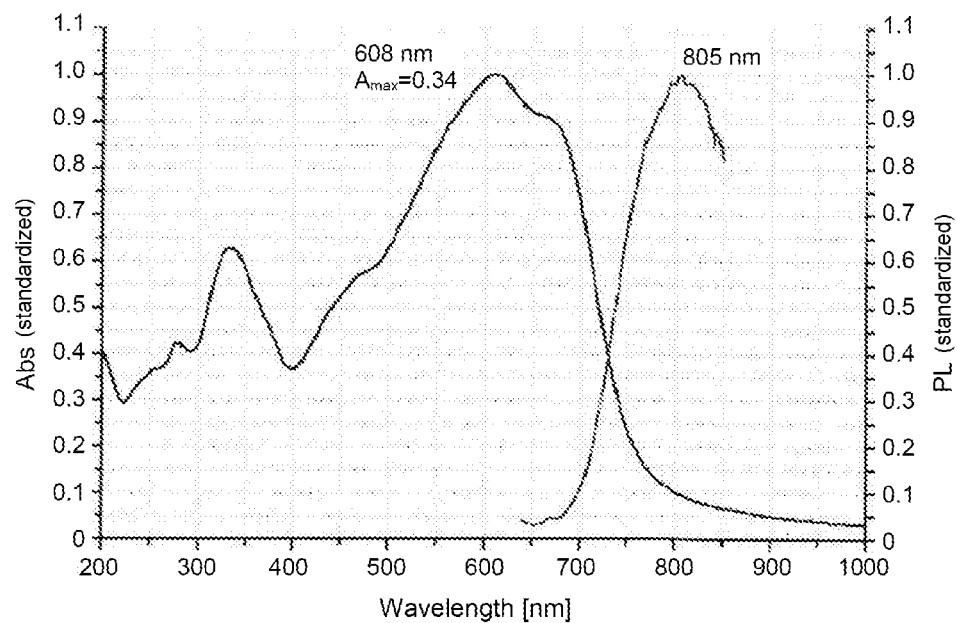
FIG. 3 shows an absorption spectrum of compound 4.

FIG. 3 shows the absorption spectrum of compound 4 (measured on 30 nm film of compound 4; PL: photoluminescence).

Figure 4:
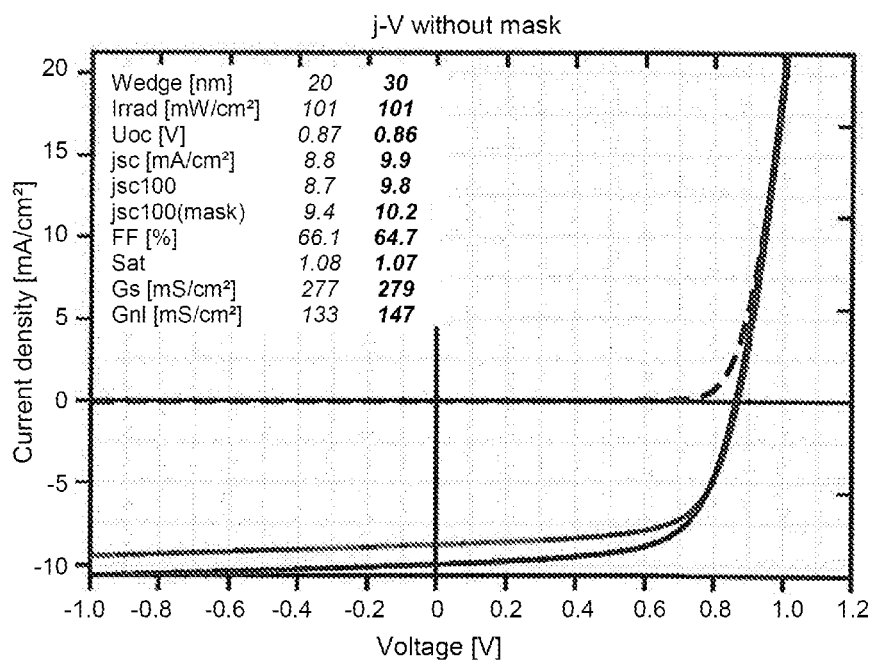
FIG. 4 shows current-voltage curves of an organic solar cell using compound 4.

FIG. 4 shows the current-voltage curves (j-V) that have been obtained using a photoactive organic electronic component in the form of an organic solar cell comprising compound 4. The measurement was conducted without a mask.

Measurements on photoactive organic electronic components were each conducted here and hereinafter (see FIGS. 6 and 8) with what is called a BHJ cell. Each cell has a glass substrate to which a transparent top contact of ITO has been applied (ITO=indium tin oxide). The cell additionally in each case has a layer comprising buckminsterfullerene (C60) and a mixed layer of the respective compounds of the invention with C60, and also a p-doped hole transport layer. The reverse contact consists of a gold layer applied by vapor deposition.

FIG. 4 shows the current-voltage curve of compound 4 in a BHJ cell as just shown above. In the specific case, the BHJ cell has, atop the ITO layer, a layer of C60 having a thickness of about 15 nm. Compound 4 has been applied to this layer together with C60 with a thickness of 30 nm. This layer is in turn followed by a layer of BPAPF having a thickness of about 10 nm. Atop said layer there is a further layer comprising BPAPF and NDP9 (commercially available p-dopant, Novaled AG) having a thickness of 30 nm. The proportion of BPAPF in this layer, based on the overall layer, is 90 percent by weight. This layer is followed by a further layer comprising NDP9 with a thickness of 1 nm, which is then followed by a gold layer with a thickness of 50 nm.

The graph shows two current-voltage curves which differ in the thickness of the mixed layer of compound 4 and C60 (20 and 30 nm). The current-voltage curve also contains the most important indices that characterize the organic solar cell of the invention. The most important indices here are the fill factor FF (quotient of maximum power of a solar cell at the point of maximum performance and the product of open-circuit voltage and short-circuit current, the open-circuit voltage Uoc and the short-circuit current jsc).

The current-voltage curves and the indices obtained demonstrate, using the example of compound 4, that the compounds of the invention are suitable for use in organic solar cells.

Figure 5:
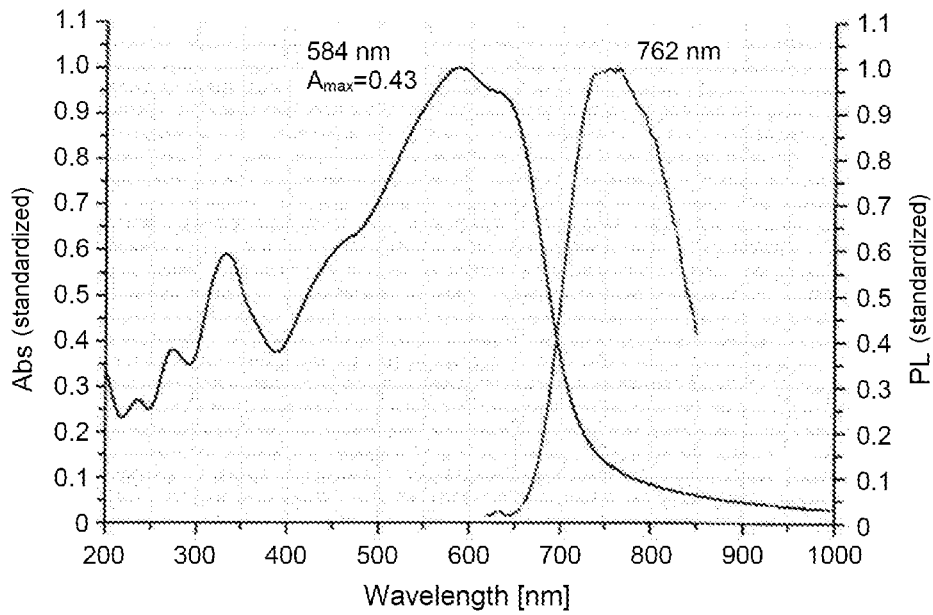
FIG. 5 shows an absorption spectrum of compound 5.

FIG. 5 shows the absorption spectrum of compound 5 (measured on 30 nm film of compound 5).

Figure 6:
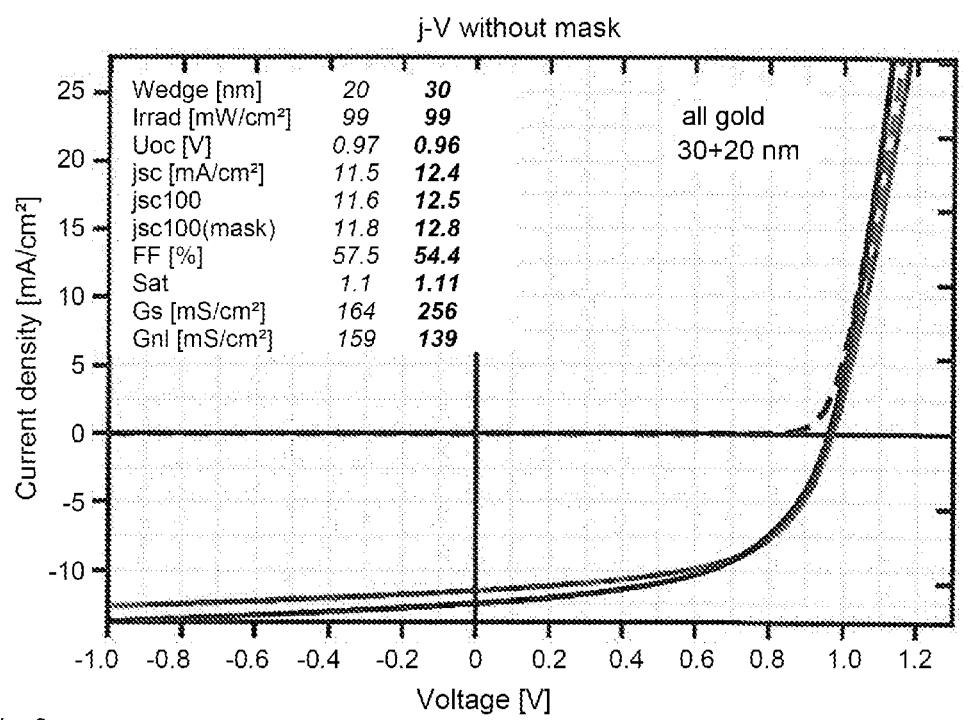
FIG. 6 shows current-voltage curves of compound 5.

FIG. 6 shows two current-voltage curves of compound 5 (layer thickness of the mixed layer with C60 20 and 30 nm, made up in a mixing ratio of 3:2 and at a substrate temperature of 50° C.), measured in a BHJ cell as already described in general terms above (in connection with FIG. 3). The specific layer sequence is as follows: ITO/C60 (15 nm)/compound 5:C60 (20/30 nm, 3:2)/BPAPF (10 nm)/BPAPF:NDP9 (30 nm, 10 wt %)/NDP (1 nm) Au (50 nm)

Figure 7:
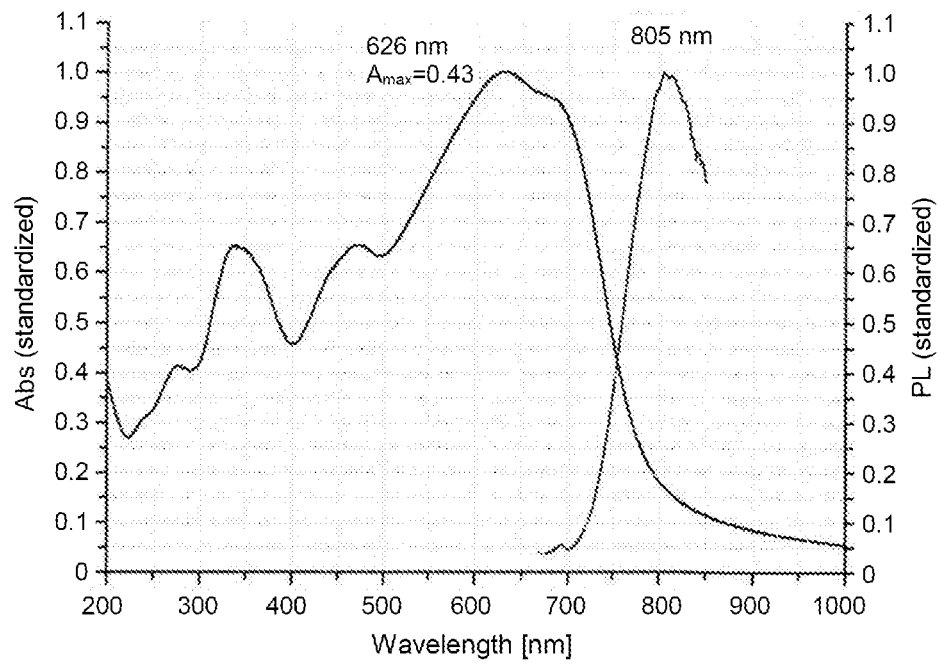
FIG. 7 shows an absorption spectrum of compound 2.

FIG. 7 shows the absorption spectrum of compound 24 (measured on 30 nm film of compound 24).

Figure 8:
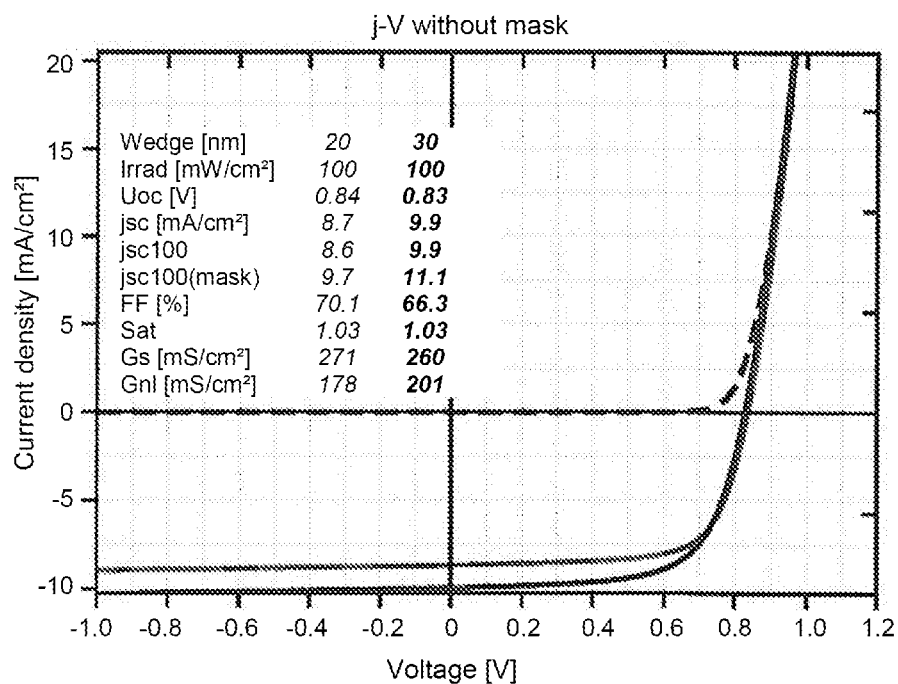
FIG. 8 shows current-voltage curves of compound 24.

FIG. 8: the current-voltage curves of compound 24 measured in a BHJ cell as already described in general terms above (in connection with FIG. 3), layer thickness of the mixed layer of compound 24 with C60 respectively 20 and 30 nm, made up in a mixing ratio of 1:1 at substrate temperature 70° C. The specific layer sequence is as follows: ITO/C60 (15 nm)/compound 24 (20/30 nm, 1:1)/BPAPF (5 nm)/BPAPF:NDP9 (45 nm, 10.1 wt %)/NDP9(1 nm) Au (50 nm).

Both the absorption properties of the compounds examined in FIGS. 1, 2, 3, 5 and 7 and the current-voltage profiles measured in the organic solar cells in FIGS. 4, 6 and 8 demonstrate that the compounds of the invention are suitable for use in organic solar cells and other photoactive organic electronic components and enable good efficiency.

Table 6 additionally summarizes some optical properties of compounds of the invention and further comparative materials. These comparative materials are comparative materials 3 to 6:

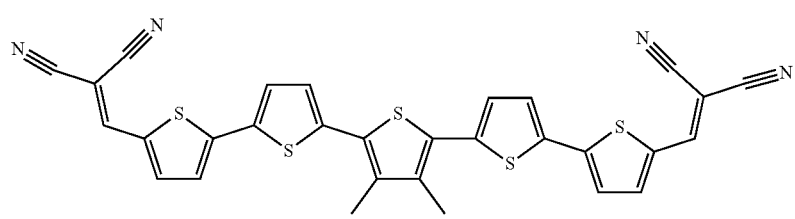

Comparative material 3

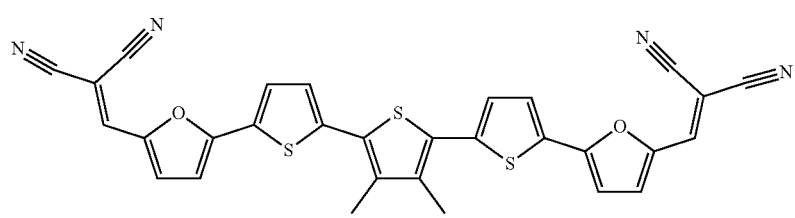

Comparative material 4

-continued

Comparative material 5

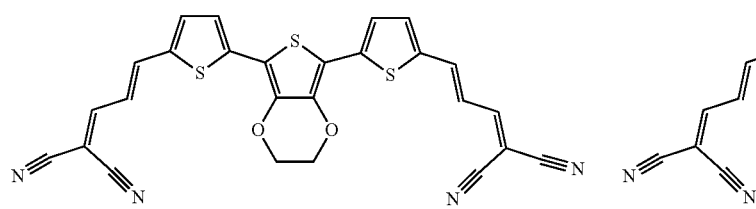

Comparative material 6

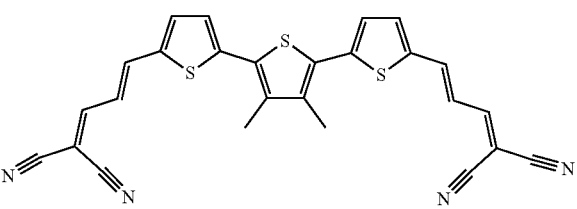

Comparative material 7

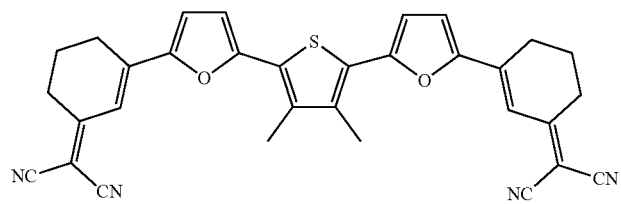

("DCC3T", Fitzner, Adv. Funct. Mat. 2015, 25, 1845)

The comparative materials are similar in terms of structure to inventive compounds 23 and 8:

Compound 23

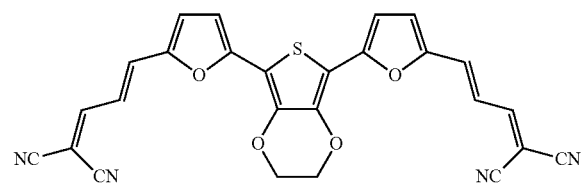

Compound 8

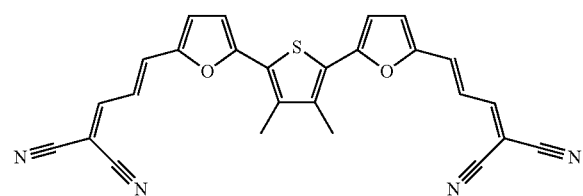

TABLE 6

Comparison of optical properties.

| Compound | $OD_{max}$ | OD integral (400-900 nm) | FWHM |
|---|---|---|---|
| Comparative material 3 | 0.45 | 101 | 209 |
| Comparative material 4 | 0.4 | 89 | 212 |
| Comparative material 5 | 0.42 | 104 | 251 |
| Comparative material 6 | 0.38 | 92 | 257 |
| Comparative material 7 | 0.45 | 84 | 192 |
| Compound 23 | 0.45 | 134 | 345 |
| Compound 8 | 0.42 | 106 | 284 |

Table 6 compares the optical density (ODmax, OD integral and the corresponding full width at half maximum FWHM) of inventive compounds (compound 23 and compound 8) with a series of comparative materials having similar structure. Optical density is a measure of absorption intensity.

Of the compounds shown, compound 23 and compound 8 have the best optical properties. More particularly, the highest full widths at half maximum under the given conditions were obtained for these compounds, as were the highest values for the OD integral. This indicates particularly good utilization of photons from the entire visible spectrum.

Compound 23 differs from comparative material 5, as does compound 8 from comparative material 6, in that the compounds of the invention each have outer five-membered rings having oxygen rather than sulfur. The better optical properties observed are thus attributable to the structural difference. Thus, for instance, a furan is more suitable as an outer five-membered ring than a thiophene ring. This fact is also apparent through the comparison of inventive compound 8 with comparative material 7 known from the literature. These materials differ both by different acceptor units and by the exchange of thiophene for furan, but only compound 8 simultaneously has a strong and broad absorption, which results in a significantly higher absorption integral, whereas, in the case of comparative material 6 containing thiophene rings only but simultaneously containing an open-chain acceptor group, the absorption integral is only slightly higher. Thus, the effect can again be attributed to the advantageous presence of furan rings.

The inventors of the present invention have additionally found that said effect additionally requires an electron-withdrawing group on said five-membered ring having at least two C=C double bonds. This is apparent, for example, from the comparison of comparative material 3 and comparative material 4. Even though the latter has furan rings as five-membered rings, it does not exhibit improved optical properties. This is attributable to the fact that, in comparative material 4, there is only one acceptor group present on the furan ring with a single C=C double bond in conjunction with the furan unit. By contrast, the improved absorption properties require the combined presence of a structural unit

with an electron-withdrawing group $A^2$ that always has at least two C=C double bonds.

The invention is not restricted by the description with reference to the working examples. Instead, the invention includes every new feature and every combination of features, especially including every combination of features in the claims, even if this feature or this combination itself is not specified explicitly in the claims or working examples.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:
1. A compound of the formula (I):

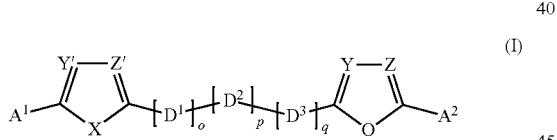

with Y, Y', Z and Z' each independently selected from: N or $CR^a$,
with X selected from: O, S, Se, $Si(R^bR^c)$, $P(R^b)$, $P(O)R^b$,
wherein the $R^a$ to $R^c$ radicals are each independently selected from the group of the following radicals: H, halogen, CN, $NR^dR^e$ where $R^d$ and $R^e$ are each independently selected from the group of the radicals: H, and cyclic or open-chain $C_1$-$C_{20}$-alkyl, where individual carbon atoms may be replaced by heteroatoms and where hydrogen atoms in the alkyl radical may be substituted,
cyclic or open-chain $C_1$-$C_{20}$-alkyl, where individual carbon atoms may be replaced by heteroatoms,
cyclic or open-chain $C_1$-$C_{20}$—O-alkyl,
cyclic or open-chain $C_1$-$C_{20}$—S-alkyl,
cyclic or open-chain $C_2$-$C_{20}$-alkenyl,
cyclic or open-chain $C_2$-$C_{20}$—O-alkenyl,
cyclic or open-chain $C_2$-$C_{20}$—S-alkenyl,
cyclic or open-chain $C_2$-$C_{20}$-alkynyl,
aryl,
heteroaryl, wherein hydrogen atoms in the alkyl, O-alkyl, S-alkyl, alkenyl, O-alkenyl, S-alkenyl, alkynyl, aryl and heteroaryl radicals may each independently be substituted; and
wherein $A^1$ is an electron-withdrawing radical having at least one C=C double bond selected from the group of the following radicals:

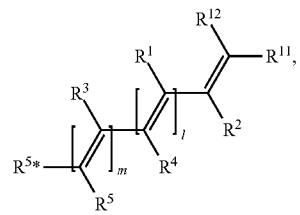

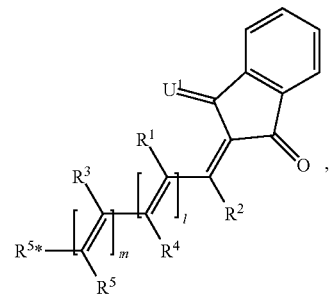

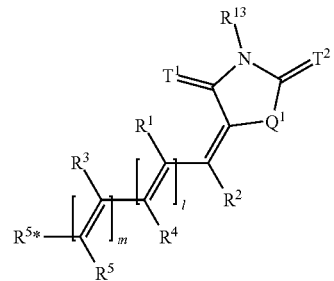

wherein, in each of these three radicals for $A^1$, either the E isomer or the Z isomer may each independently be present for each C=C double bond in each case, and
wherein $A^2$ is an electron-withdrawing radical having at least two conjugated C=C double bonds selected from the group of the following radicals:

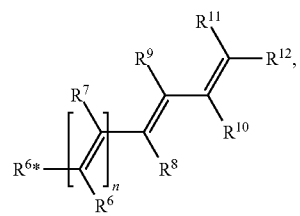

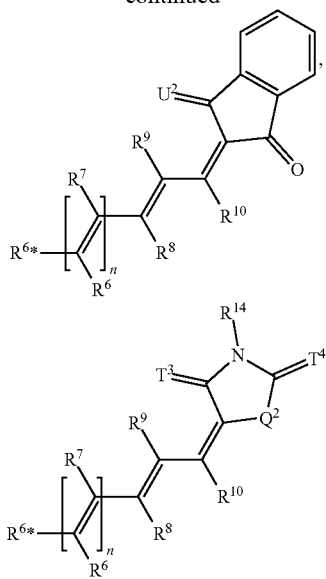

wherein, in each of these three radicals for $A^2$, either the E isomer or the Z isomer may each independently be present for each C=C double bond in each case, wherein m, l and n are each independently 0 or 1, wherein $R^1$ to $R^{10}$ and $R^{5*}$ and $R^{6*}$ for the $A^1$ and $A^2$ groups are each independently selected from the group of the following radicals: H, halogen, CN, cyclic or open-chain $C_1$-$C_{20}$-alkyl, cyclic or open-chain $C_2$-$C_{20}$-alkenyl, cyclic or open-chain $C_1$-$C_{20}$—O-alkyl, aryl, heteroaryl, where hydrogen atoms in the alkyl, alkenyl, O-alkyl, aryl and heteroaryl radicals may each independently be substituted; and wherein it is possible in each case independently for a ring to be formed by the following pairs of radicals together: $R^1$ and $R^3$, $R^2$ and $R^4$, $R^4$ and $R^5$, $R^3$ and $R^{5*}$, $R^7$ and $R^9$, $R^6$ and $R^8$, $R^8$ and $R^{10}$, $R^{6*}$ and $R^7$;

with the proviso that, for $A^1$, exactly one of the $R^{5*}$, $R^5$, $R^4$, $R^3$, $R^2$ and $R^1$ represents a linkage ⁞ by means of which $A^1$ is bonded to the structural element

in the compound of the formula (I), and with the proviso that, for $A^2$, exactly one of the $R^{6*}$, $R^6$, $R^7$, $R^8$, $R^9$ and $R^{10}$ radicals represents a linkage ⁞ by means of which $A^2$ is bonded to the structural element

of the compound of the formula (I);

wherein $R^{11}$ and $R^{12}$ for the $A^1$ and $A^2$ groups are each independently selected from the group of the radicals: H, CN, COO$R^f$ where $R^f$ is selected from the group of the radicals: H and cyclic or open-chain $C_1$-$C_{20}$-alkyl, where hydrogen atoms in the alkyl may be replaced by fluorine atoms, with the proviso that $R^{11}$ and $R^{12}$ cannot both be H, wherein the $R^{13}$ and $R^{14}$ radicals are independently selected from the same group of radicals as $R^d$ and $R^c$, and wherein $U^1$, $U^2$, and $T^1$ to $T^4$ are each independently selected from the group consisting of: O, S and $C(CN)_2$, and wherein $Q^1$ and $Q^2$ are each independently selected from the group consisting of: O and S, and wherein the conjugated $D^1$, $D^2$ and $D^3$ blocks are each independently selected from the group of the following structural units:

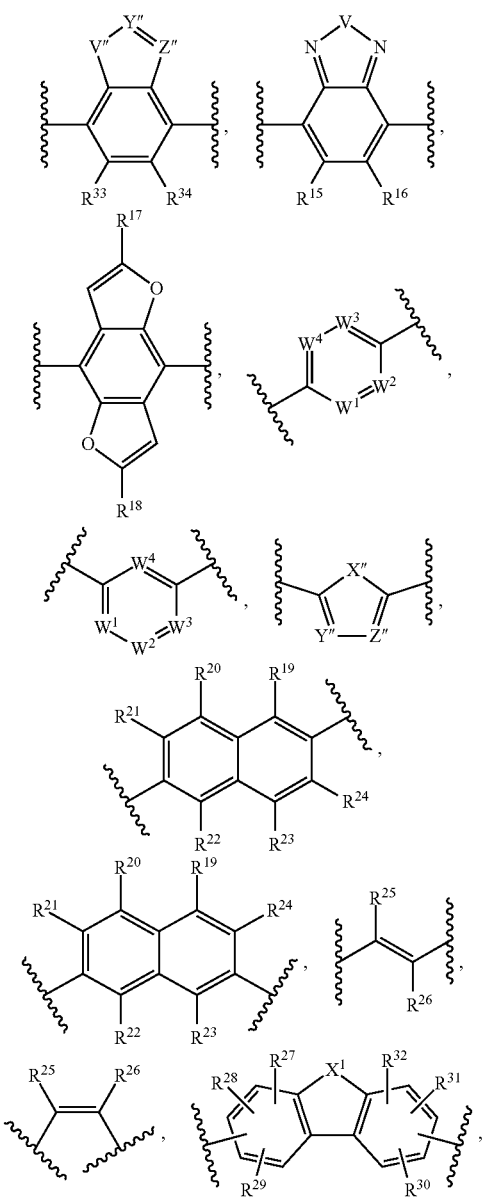

wherein the coefficients o and q each independently assume the values of 0 and 1 and the coefficient p assumes the values of 0, 1, 2, 3, 4 and 5, with the proviso that at least one of the coefficients o, p and q is not 0, Y" is selected from: N or CR$^g$;
Z" is selected from: N or CR$^h$;
X" is selected from: O, S, Se, Si(R$^i$R$^j$), P(R$^i$), P(O)R$^i$;
V is selected from: O, S, Se or NR$^k$;
V' is selected from: O, S, Se or NR$^k$; preferably NR$^k$,
X$^1$ is selected from: NR$^l$, CR$^l$R$^m$;
W$^1$ to W$^4$ are independently selected from: N, CR$^n$;
wherein the R$^g$ to R$^n$ radicals and the W$^{15}$ to R$^{34}$ radicals are each independently selected from the group of the radicals as R$^a$ to R$^c$; and
wherein the R$^g$ and R$^h$ radicals may be joined to one another in the form of a ring structure and where an aryl radical may be fused onto the ring structure, where any aryl radical fused to the ring structure may be substituted.

2. The compound as claimed in claim 1, wherein exactly one of the three coefficients o, p and q is 1, while the two other coefficients are 0.

3. The compound as claimed in claim 1, wherein, for A$^1$, the R$^{5*}$ radical represents the linkage by means of which A$^1$ is bonded to the structural element

of the compound of the formula (I), such that A$^1$ is selected from the group of the following radicals:

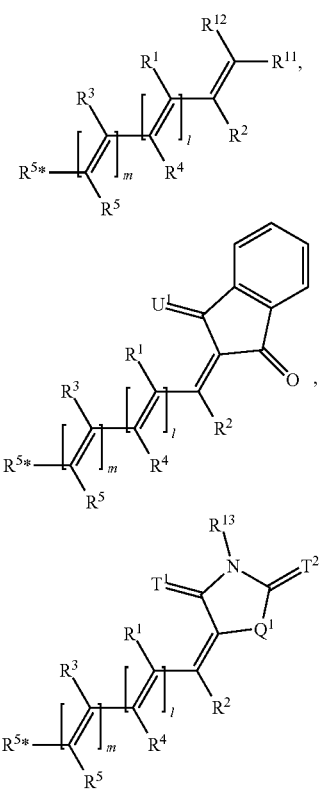

wherein, in each of these three radicals for A$^1$, either the E isomer or the Z isomer may each independently be present for each C=C double bond in each case, and wherein, for A$^2$, the R$^{6*}$ radical represents the linkage by means of which A$^2$ is bonded to the structural element

of the compound of the formula (I), such that A$^2$ is selected from the group of the following radicals:

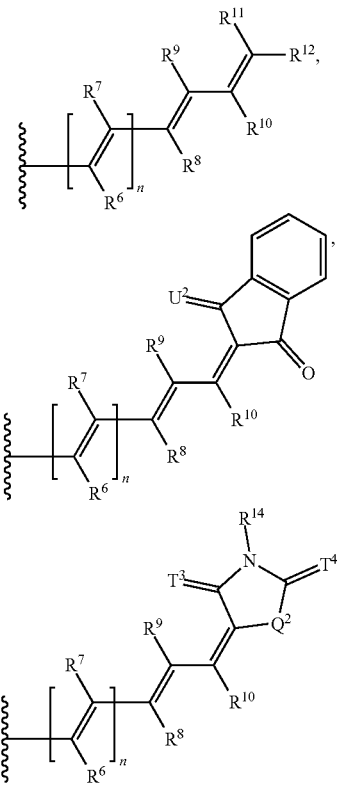

wherein, in each of these three radicals for A$^2$, either the E isomer or the Z isomer may each independently be present for each C=C double bond in each case.

4. The compound as claimed in claim 1, wherein the R$^{11}$ and R$^{12}$ radicals are each CN.

5. The compound as claimed in claim 1, wherein the R$^1$ to R$^{10}$ and R$^{5*}$ and R$^{6*}$ radicals are each independently selected from the group of the following radicals: H, F, linear or branched C$_1$-C$_5$-alkyl, and wherein hydrogens in the alkyl may each independently be replaced by fluorine atoms.

6. The compound as claimed in claim 1, wherein A$^1$ is selected from the group of the following radicals:

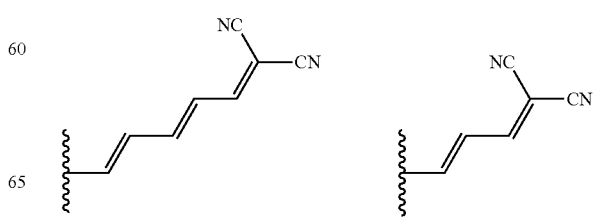

-continued

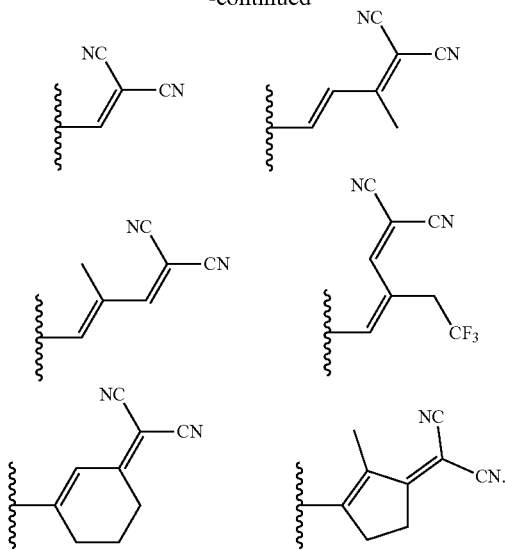

7. The compound as claimed in claim 1, wherein $A^2$ is selected from the group of the following radicals:

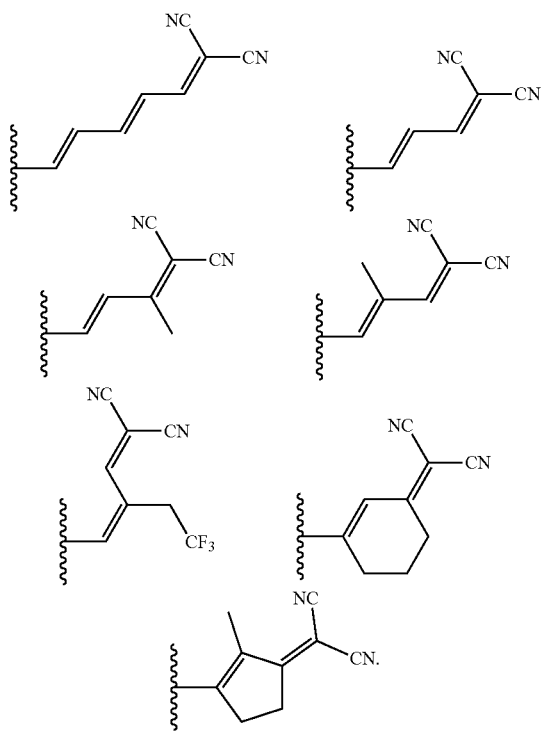

8. The compound as claimed in claim 1 with X=oxygen.
9. The compound as claimed in claim 1 with X=oxygen, with m=n=0, with o=q=0 and with p selected from: 1, 2, 3, 4 and 5, having the formula:

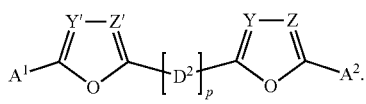

10. The compound as claimed in claim 1, wherein Y, Y', Z and Z' are each independently selected from: N or $CR^a$, and
wherein $R^a$ is selected from the group of the following radicals: H, F, $C_1$-$C_5$-alkyl, $C_1$-$C_5$-alkenyl, $C_1$-$C_5$—S-Alkyl, $C_2$-$C_5$—O-alkenyl, $C_2$-$C_5$—S-alkenyl, $C_2$-$C_5$-alkynyl, $C_2$-$C_5$-Alkynyl, phenyl, wherein hydrogen atoms in the alkyl, O-alkyl, S-alkyl, alkenyl, O-alkenyl, S-alkenyl, alkynyl and phenyl radicals may each independently be substituted.

11. The compound as claimed in claim 1, wherein Y, Y', Z, Z' are each independently selected from: N, CH, C—F, C—$CH_3$, C—$CF_3$, C—$C_2H_5$, C—$C_3H_8$, C—$OCH_3$, C—$OC_2H_5$, C—$SCH_3$, C—$SC_2H_5$.

12. The compound as claimed in claim 1, wherein Y, Y', Z, Z' are each CH.

13. The compound as claimed in claim 1, wherein at least one of the conjugated $D^1$ to $D^3$ blocks is present in the compound and has the formula

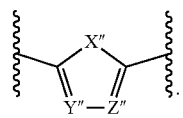

14. The compound as claimed in claim 1, wherein at least one of the conjugated $D^1$ to $D^3$ blocks is present in the compound and has the formula

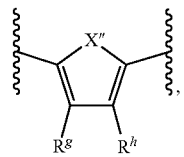

wherein the $R^g$ and $R^h$ radicals are independently selected from the group of the following radicals: H, F, $C_1$-$C_5$-alkyl, where individual carbon atoms may be replaced by heteroatoms, $C_1$-$C_5$—O-alkyl, $C_1$-$C_5$—S-alkyl, where hydrogen atoms in the alkyl, O-alkyl and S-alkyl radicals may each independently be substituted by fluorine, and
wherein the $R^g$ and $R^h$ radicals may be joined to one another in the form of a ring structure and where an aryl radical may be fused to the ring structure.

15. The compound as claimed in claim 1, wherein X"=S.
16. The compound as claimed in claim 1 having the following formula:

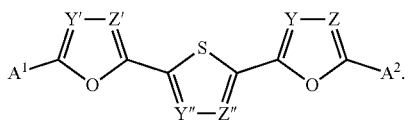

17. The compound as claimed in claim 1, wherein at least one of the conjugated $D^1$ to $D^3$ blocks is present in the compound and has the formula

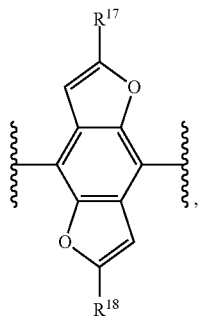

wherein $R^{17}$ and $R^{18}$ are each independently selected from the group of the following radicals: H, F, $C_1$-$C_5$-alkyl, $C_1$-$C_5$—O-alkyl, $C_1$-$C_5$—S-alkyl, where hydrogen atoms in the alkyl, O-alkyl and S-alkyl radicals may each independently be replaced by fluorine atoms.

18. The compound as claimed in claim 1, wherein at least one of the conjugated $D^1$ to $D^3$ blocks is present in the compound and has the formula

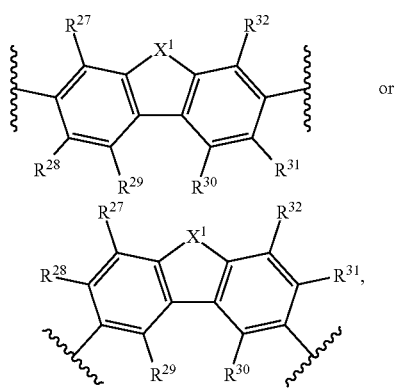

or wherein $X^1$ is selected from: $NR^1$, $CR^lR^m$,
wherein $R^l$ and $R^m$ are each independently selected from the group of the radicals: H, open-chain $C_1$-$C_5$-alkyl, $C_5$-$C_{12}$-aryl, $C_5$-$C_{12}$-heteroaryl, where hydrogen atoms in the open-chain $C_1$-$C_5$-alkyl may at least partly be replaced by fluorine atoms and where hydrogen atoms in the $C_5$-$C_{12}$-aryl and the $C_5$-$C_{12}$-heteroaryl may at least partly be substituted, and
wherein $R^{27}$ to $R^{32}$ are each independently selected from the group of the following radicals: H, F, $C_1$-$C_5$-alkyl, $C_1$-$C_5$—O-alkyl, $C_1$-$C_5$—S-alkyl, where hydrogen atoms in the alkyl, O-alkyl and S-alkyl radicals may each independently be replaced by fluorine atoms.

19. The compound as claimed in claim 1, wherein at least one of the conjugated $D^1$ to $D^3$ blocks is present in the compound and has the formula

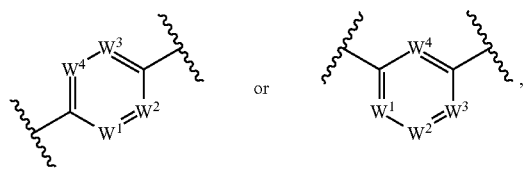

wherein $W^1$ to $W^4$ are independently selected from: N and $CR^n$, and
wherein $R^n$ is selected from the group of the following radicals: H, F, $C_1$-$C_5$-alkyl, $C_1$-$C_5$—O-alkyl, $C_1$-$C_5$—S-alkyl, wherein hydrogen atoms in the alkyl, O-alkyl and S-alkyl radicals may each independently be replaced by fluorine atoms.

20. The compound as claimed in claim 1, wherein at least one of the conjugated $D^1$ to $D^3$ blocks is present in the compound and has the formula

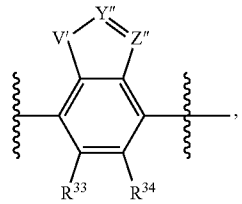

wherein $R^{33}$ to $R^{34}$ are each independently selected from the group of the following radicals: H, F, $C_1$-$C_5$-alkyl, $C_1$-$C_5$—O-alkyl, $C_1$-$C_5$—S-alkyl, where hydrogen atoms in the alkyl, O-alkyl and S-alkyl radicals may each independently be replaced by fluorine atoms and with $Y''$ selected from: N or;
with $Z''$ selected from: N or $CR^h$;
with $V'$ selected from: O, S, Se or $NR^k$;
wherein $R^g$ and $R^h$ selected as one of the $R^a$ to $R^c$ radicals, and
wherein $R^k$ is selected from the group of radicals: H, open-chain $C_1$-$C_5$-alkyl, $C_5$-$C_{12}$-aryl, $C_5$-$C_{12}$-heteroaryl, where hydrogen atoms in the open-chain $C_1$-$C_5$-alkyl may at least partly be replaced by fluorine atoms and where hydrogen atoms in the $C_5$-$C_{12}$-aryl and the $C_5$-$C_{12}$-heteroaryl may at least partly be substituted.

21. The compound as claimed in claim 1, wherein the conjugated $D^1$ to $D^3$ blocks are independently selected from the group of the following structural units:

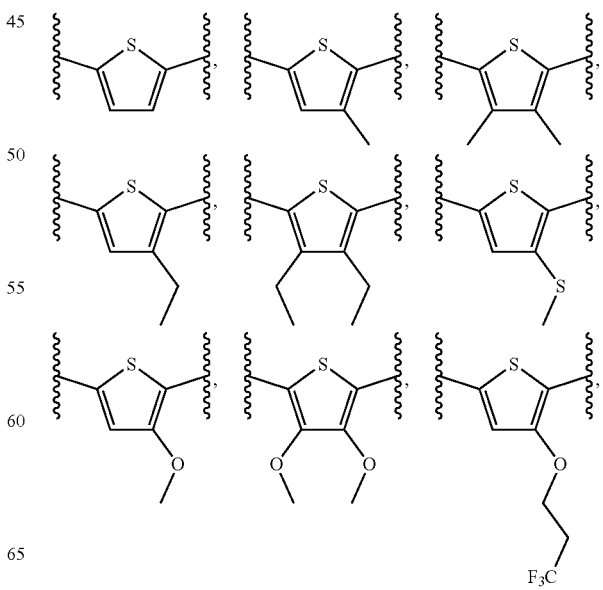

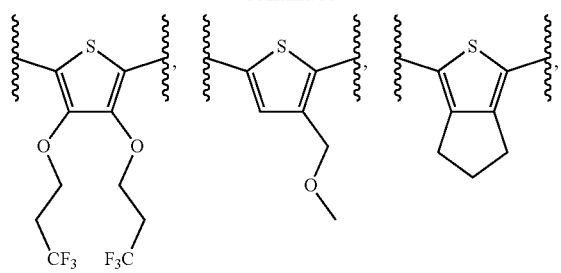
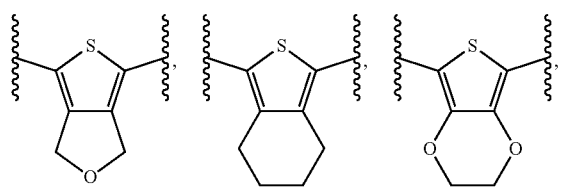
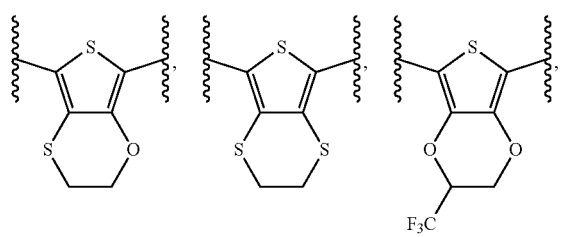
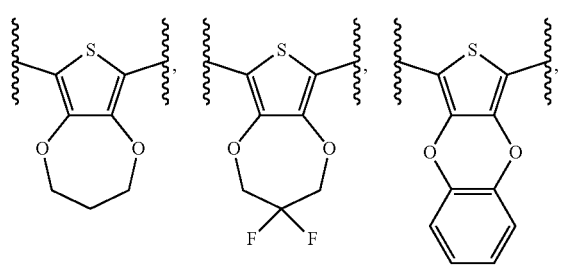
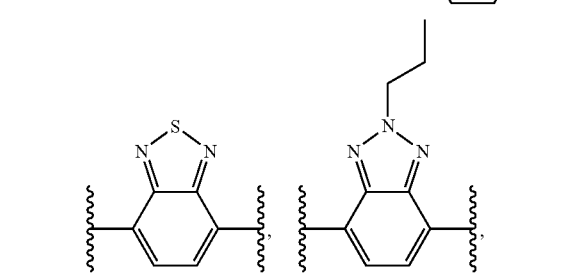
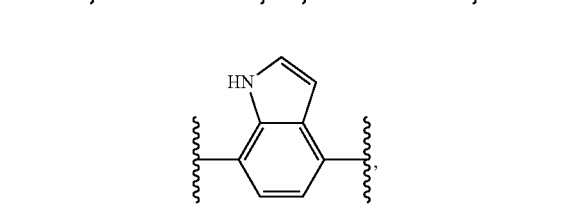
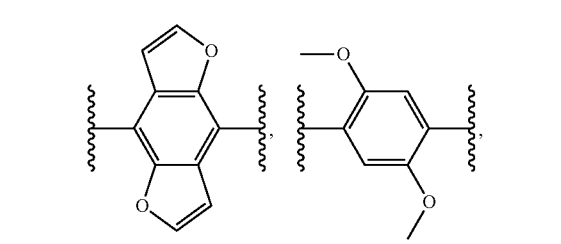
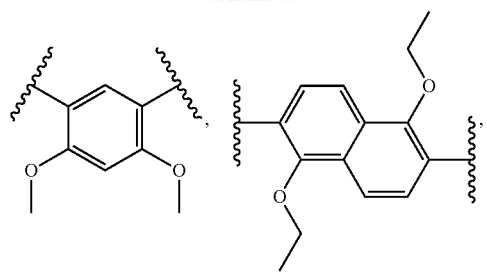
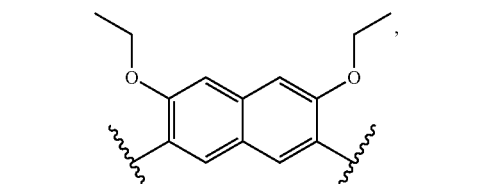
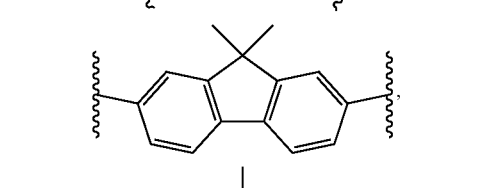
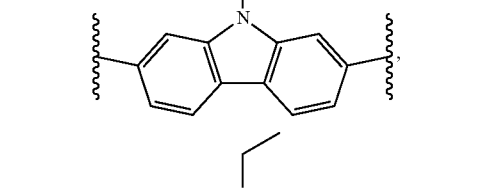
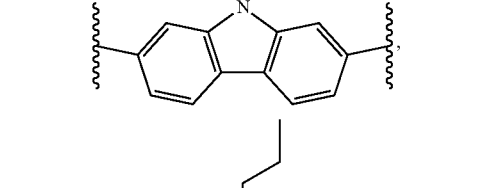
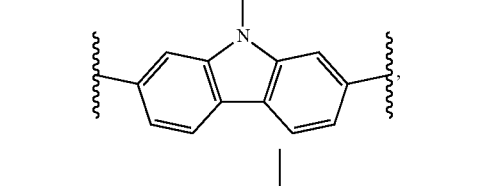
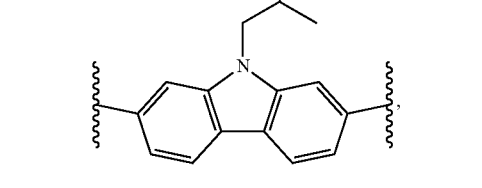
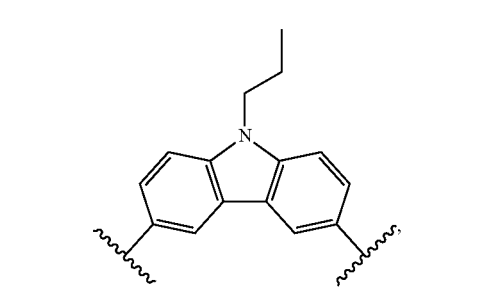

-continued

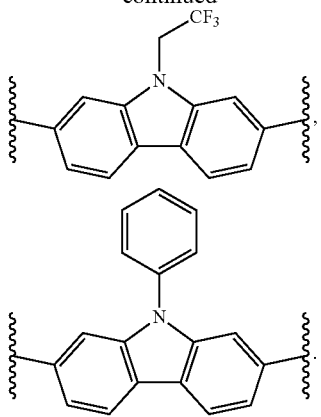

22. A method of using one or more of the compound as claimed in claim 1 in a photoactive organic electronic component.

23. The method of use as claimed in claim 22, wherein the component is an organic solar cell.

24. A photoactive organic electronic component comprising the compound as claimed in claim 1.

25. The compound as claimed in claim 1 prepared from a compound having the following formula

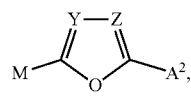

wherein Y, Z and $A^2$ are as defined in claim 1 and where M is selected from one of the following functional groups:

—SnR*$_3$,—B(OR*)$_2$,—Zn-Hal*,—Mg-Hal*, wherein R* is a $C_1$-$C_{10}$-alkyl and where the Hal* group is a halogen.

26. A process for preparing the compound as claimed in claim 1, comprising, as a process step, a coupling reaction, wherein either the compound reacts with a further compound of the following formula

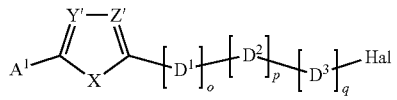

wherein $A^1$, Y', Z', X, $D^1$ to $D^3$ and o, p and q are defined as defined in claim 1, and where the Hal group is a halogen, or two equivalents of the compound are reacted with a second further compound of the following formula

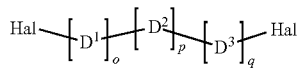

wherein $D^1$ to $D^3$, o, p and q are as defined in claim 1, and wherein the Hal group is a halogen.

* * * * *